US010441589B2

(12) United States Patent
Hartman et al.

(10) Patent No.: US 10,441,589 B2
(45) Date of Patent: Oct. 15, 2019

(54) COMBINATIONS AND METHODS COMPRISING A CAPSID ASSEMBLY INHIBITOR

(71) Applicants: Novira Therapeutics, Inc., Doylestown, PA (US); Janssen Sciences Ireland Unlimited Company, Co Cork (IE)

(72) Inventors: George Hartman, Lansdale, PA (US); Osvaldo Flores, North Wales, PA (US); Klaus Klumpp, West Chester, PA (US); Man Iu Lam, Fort Lee, NJ (US); Jan Martin Berke, Beerse (BE)

(73) Assignees: NOVIRA THERAPEUTICS, INC., Doylestown, PA (US); Janssen Sciences Ireland Unlimited Company, Ringaskiddy, Co Cork (IE)

( * ) Notice: Subject to any disclaimer, the term of this patent is extended or adjusted under 35 U.S.C. 154(b) by 1 day.

(21) Appl. No.: 15/488,368

(22) Filed: Apr. 14, 2017

(65) Prior Publication Data
US 2017/0340642 A1    Nov. 30, 2017

Related U.S. Application Data

(60) Provisional application No. 62/323,251, filed on Apr. 15, 2016, provisional application No. 62/421,035, filed on Nov. 11, 2016.

(51) Int. Cl.
| | | |
|---|---|---|
| A01N 43/04 | (2006.01) |
| A61K 31/70 | (2006.01) |
| A61K 31/52 | (2006.01) |
| A61K 31/40 | (2006.01) |
| A61K 31/445 | (2006.01) |
| A61K 31/522 | (2006.01) |
| A61K 31/675 | (2006.01) |
| A61K 31/7072 | (2006.01) |
| A61K 31/03 | (2006.01) |
| A61K 31/095 | (2006.01) |
| A61K 31/18 | (2006.01) |
| A61K 31/706 | (2006.01) |
| C12N 7/06 | (2006.01) |

(52) U.S. Cl.
CPC .............. *A61K 31/52* (2013.01); *A61K 31/03* (2013.01); *A61K 31/095* (2013.01); *A61K 31/18* (2013.01); *A61K 31/40* (2013.01); *A61K 31/445* (2013.01); *A61K 31/522* (2013.01); *A61K 31/675* (2013.01); *A61K 31/7072* (2013.01); *A61K 31/706* (2013.01); *C12N 7/06* (2013.01)

(58) Field of Classification Search
None
See application file for complete search history.

(56) References Cited

U.S. PATENT DOCUMENTS

| | | |
|---|---|---|
| 3,843,662 A | 10/1974 | Holland |
| 4,569,940 A | 2/1986 | Watts |
| 4,962,101 A | 10/1990 | Dininno et al. |
| 5,272,167 A | 12/1993 | Girijavallabhan et al. |
| 5,308,826 A | 5/1994 | Chin et al. |
| 5,314,880 A | 5/1994 | Whittaker et al. |
| 5,585,327 A | 12/1996 | Chin et al. |
| 5,607,929 A | 3/1997 | Nicol |
| 5,708,034 A | 1/1998 | Kleemann et al. |
| 5,723,411 A | 3/1998 | Stevenson |
| 5,795,907 A | 8/1998 | Kalindjian et al. |
| 5,912,260 A | 6/1999 | Kalindjian et al. |
| 5,919,970 A | 7/1999 | Song et al. |
| 5,939,423 A | 8/1999 | Karlin |
| 6,025,367 A | 2/2000 | Forbes et al. |
| 6,265,408 B1 | 7/2001 | Forbes et al. |
| 6,476,025 B1 | 11/2002 | Flockerzi et al. |
| 6,650,463 B2 | 11/2003 | Obikawa et al. |
| 6,668,527 B2 | 12/2003 | Chupak et al. |
| 6,780,389 B2 | 8/2004 | Karl et al. |
| 7,115,595 B2 | 10/2006 | Sunagawa et al. |
| 7,186,735 B2 | 3/2007 | Strobel et al. |
| 7,338,956 B2 | 3/2008 | Strobel et al. |
| 7,368,457 B2 | 5/2008 | Josien et al. |
| 7,384,967 B2 | 6/2008 | Polisetti et al. |
| 7,576,688 B2 | 1/2009 | Suzuki et al. |
| 7,541,373 B2 | 6/2009 | Polisetti et al. |
| 7,544,700 B2 | 6/2009 | Halazy et al. |
| 7,595,322 B2 | 9/2009 | Morgan et al. |
| 7,608,723 B2 | 10/2009 | Boyce et al. |
| 7,750,158 B2 | 7/2010 | Shankar et al. |
| 7,786,104 B2 | 8/2010 | Dubois et al. |
| 7,790,726 B2 | 9/2010 | Zhang et al. |
| 7,838,525 B2 | 11/2010 | Jones et al. |
| 7,888,373 B2 | 2/2011 | Morgan et al. |

(Continued)

FOREIGN PATENT DOCUMENTS

| | | |
|---|---|---|
| CA | 2950807 A1 | 12/2015 |
| CN | 102093320 A | 6/2011 |

(Continued)

OTHER PUBLICATIONS

[Online] CAS (STN), 148:183450, RN 296790-26-6.

(Continued)

*Primary Examiner* — Patrick T Lewis

(74) *Attorney, Agent, or Firm* — Lathrop Gage LLP; Brian C. Trinque; Benjamin A. Vaughan

(57) ABSTRACT

The present disclosure is directed to capsid assembly inhibitor compositions and methods for use in the treatment of hepatitis B virus infection.

4 Claims, 16 Drawing Sheets

Specification includes a Sequence Listing.

(56) References Cited

U.S. PATENT DOCUMENTS

| | | |
|---|---|---|
| 7,994,168 B2 | 8/2011 | Lennig et al. |
| 8,071,779 B2 | 12/2011 | Richards et al. |
| 8,084,457 B2 | 12/2011 | Choidas et al. |
| 8,097,728 B2 | 1/2012 | Gu et al. |
| 8,101,620 B2 | 1/2012 | Morgan et al. |
| 8,153,650 B2 | 4/2012 | Dubois et al. |
| 8,153,803 B2 | 4/2012 | Kazantsev et al. |
| 8,207,195 B2 | 6/2012 | Navratil et al. |
| 8,227,489 B2 | 7/2012 | Dubois et al. |
| 8,273,754 B2 | 9/2012 | Hill et al. |
| 8,299,096 B2 | 10/2012 | Navratil et al. |
| 8,299,114 B2 | 10/2012 | Dubois et al. |
| 8,354,425 B2 | 1/2013 | Dubois et al. |
| 8,394,820 B2 | 3/2013 | Dubois et al. |
| 8,399,491 B2 | 3/2013 | Dubois et al. |
| 8,404,747 B2 | 3/2013 | Kazantsev et al. |
| 8,410,147 B2 | 4/2013 | Peterson et al. |
| 8,536,168 B2 | 9/2013 | Dai et al. |
| 8,609,668 B2 | 12/2013 | Cuconati et al. |
| 8,629,274 B2 | 1/2014 | Hartman et al. |
| 8,808,702 B2 | 8/2014 | Reddy et al. |
| 8,889,716 B2 | 11/2014 | Prime et al. |
| 8,993,771 B2 | 3/2015 | Hartman et al. |
| 9,051,296 B2 | 6/2015 | Yamagishi et al. |
| 9,061,008 B2 * | 6/2015 | Hartman ............... C07C 311/46 |
| 9,066,932 B2 | 6/2015 | Hartman et al. |
| 9,115,101 B2 | 8/2015 | Bodil Van Niel et al. |
| RE45,670 E | 9/2015 | Polisetti et al. |
| 9,676,747 B2 | 6/2017 | Hartman et al. |
| 9,884,818 B2 | 2/2018 | Vandyck et al. |
| 2002/0049236 A1 | 4/2002 | Chupak et al. |
| 2004/0039009 A1 | 2/2004 | Jagtap et al. |
| 2005/0009871 A1 | 1/2005 | Ramesh et al. |
| 2005/0054850 A1 | 3/2005 | Wu et al. |
| 2005/0129833 A1 | 6/2005 | Kincaid et al. |
| 2005/0148632 A1 | 7/2005 | Tokumasu et al. |
| 2005/0239833 A1 | 10/2005 | Kazantsev et al. |
| 2006/0040984 A1 | 2/2006 | Luckhurst et al. |
| 2006/0100228 A1 | 5/2006 | Shankar et al. |
| 2006/0100257 A1 | 5/2006 | Muto et al. |
| 2006/0122236 A1 | 6/2006 | Wood et al. |
| 2007/0142440 A1 | 6/2007 | Burgdorf et al. |
| 2007/0161578 A1 | 7/2007 | Hwa et al. |
| 2009/0018118 A1 | 1/2009 | Urleb et al. |
| 2009/0036420 A1 | 2/2009 | Galley et al. |
| 2009/0105218 A1 | 4/2009 | Ulven et al. |
| 2009/0163545 A1 | 6/2009 | Goldfarb |
| 2009/0259044 A1 | 10/2009 | Kazantsev |
| 2009/0325959 A1 | 12/2009 | Vittitow et al. |
| 2009/0325960 A1 | 12/2009 | Fulcher et al. |
| 2010/0008968 A1 | 1/2010 | Lampe et al. |
| 2010/0016310 A1 | 1/2010 | Ingraham |
| 2010/0022517 A1 | 1/2010 | Richards et al. |
| 2010/0204210 A1 | 8/2010 | Sorensen et al. |
| 2011/0009622 A1 | 1/2011 | Jitsuoka et al. |
| 2011/0064695 A1 | 3/2011 | Qiu et al. |
| 2011/0064696 A1 | 3/2011 | Or et al. |
| 2011/0184019 A1 | 6/2011 | Zitzmann et al. |
| 2011/0189771 A1 | 8/2011 | Block et al. |
| 2011/0275630 A1 | 11/2011 | Matulenko et al. |
| 2011/0301158 A1 | 12/2011 | Polisetti et al. |
| 2013/0005756 A1 | 1/2013 | Vittitow et al. |
| 2013/0131059 A1 | 5/2013 | Lampe et al. |
| 2013/0131106 A1 | 5/2013 | Lampe et al. |
| 2013/0142827 A1 | 6/2013 | Block et al. |
| 2013/0203733 A1 | 9/2013 | Kazantsev et al. |
| 2013/0251673 A1 | 9/2013 | Hartman et al. |
| 2013/0267517 A1 | 10/2013 | Guo et al. |
| 2013/0303552 A1 | 11/2013 | Xu et al. |
| 2014/0178337 A1 | 6/2014 | Hartman et al. |
| 2014/0179665 A1 | 6/2014 | Hartman et al. |
| 2014/0275167 A1 | 9/2014 | Hartman |
| 2015/0152073 A1 | 6/2015 | Hartman et al. |
| 2015/0174115 A1 | 6/2015 | Hartman et al. |
| 2015/0175602 A1 | 6/2015 | Brown et al. |
| 2015/0197493 A1 | 7/2015 | Hartman |
| 2015/0197533 A1 | 7/2015 | Hartman et al. |
| 2015/0216938 A1 | 8/2015 | Hartman |
| 2015/0225355 A1 | 8/2015 | Hartman |
| 2015/0259324 A1 | 9/2015 | Hartman et al. |
| 2015/0274652 A1 | 10/2015 | Hartman |
| 2015/0274653 A1 | 10/2015 | Vandyck et al. |
| 2016/0000812 A1 | 1/2016 | Hartman et al. |
| 2016/0002155 A1 | 1/2016 | Vandyck et al. |
| 2016/0051512 A1 | 2/2016 | Vandyck et al. |
| 2016/0115125 A1 | 4/2016 | Vandyck et al. |
| 2016/0158214 A1 | 6/2016 | Hartman |
| 2016/0272599 A1 | 9/2016 | Hartman et al. |
| 2017/0015629 A1 | 1/2017 | Hartman |
| 2017/0114018 A1 | 4/2017 | Hartman |
| 2017/0182021 A1 | 6/2017 | Hartman |
| 2018/0141905 A1 | 5/2018 | Vandyck et al. |

FOREIGN PATENT DOCUMENTS

| | | |
|---|---|---|
| EP | 0 232 067 A2 | 8/1987 |
| EP | 0 742 200 B1 | 7/1999 |
| EP | 2 280 001 A1 | 2/2011 |
| JP | S62-142164 A | 6/1987 |
| JP | 2008-525406 A | 7/2008 |
| JP | 2008-179621 A | 8/2008 |
| JP | 2010-535172 A | 11/2010 |
| WO | 1984/003281 A1 | 8/1984 |
| WO | 1992/007835 A1 | 5/1992 |
| WO | 1998/023285 A1 | 6/1998 |
| WO | 1999/009022 A1 | 2/1999 |
| WO | 1999/038845 A1 | 8/1999 |
| WO | 1999/048492 A1 | 9/1999 |
| WO | 1999/065906 A1 | 12/1999 |
| WO | 2001/005390 A2 | 1/2001 |
| WO | 2001/019788 A2 | 3/2001 |
| WO | 2001/051487 A1 | 7/2001 |
| WO | 2001/055121 A1 | 8/2001 |
| WO | 2001/085694 A2 | 11/2001 |
| WO | 2002/051410 A2 | 7/2002 |
| WO | 2002/064618 A2 | 8/2002 |
| WO | 2003/007955 A2 | 1/2003 |
| WO | 2003/044016 A1 | 5/2003 |
| WO | 2003/101961 A1 | 12/2003 |
| WO | 2004/010943 A2 | 2/2004 |
| WO | 2004/011427 A2 | 2/2004 |
| WO | 2004/022060 A2 | 3/2004 |
| WO | 2004/058709 A1 | 7/2004 |
| WO | 2004/086865 A1 | 11/2004 |
| WO | 2004/099192 A2 | 11/2004 |
| WO | 2004/100947 A2 | 11/2004 |
| WO | 2005/016922 A2 | 2/2005 |
| WO | 2005/044797 A1 | 5/2005 |
| WO | 2005/087217 A1 | 9/2005 |
| WO | 2005/105785 A2 | 11/2005 |
| WO | 2005/115374 A1 | 12/2005 |
| WO | 2006/002133 A1 | 1/2006 |
| WO | 2006/024834 A1 | 3/2006 |
| WO | 2006/053109 A1 | 5/2006 |
| WO | 2006/067445 A2 | 6/2006 |
| WO | 2006/067446 A1 | 6/2006 |
| WO | 2006/123257 A2 | 11/2006 |
| WO | 2006/128129 A2 | 11/2006 |
| WO | 2006/128172 A2 | 11/2006 |
| WO | 2007/031791 A1 | 3/2007 |
| WO | 2007070556 A2 | 6/2007 |
| WO | 2008/011476 A2 | 1/2008 |
| WO | 2008/022171 A1 | 2/2008 |
| WO | 2008/093614 A1 | 8/2008 |
| WO | 2008/137794 A1 | 11/2008 |
| WO | 2008/154819 A1 | 12/2008 |
| WO | 2009/016088 A1 | 2/2009 |
| WO | 2009/062402 A1 | 5/2009 |
| WO | 2009/086303 A2 | 7/2009 |
| WO | 2009/131065 A1 | 10/2009 |
| WO | 2009/146013 A1 | 12/2009 |
| WO | 2010/018113 A2 | 2/2010 |
| WO | 2010/043592 A1 | 4/2010 |
| WO | 2010/088000 A2 | 8/2010 |

(56) References Cited

FOREIGN PATENT DOCUMENTS

| WO | 2010/123139 A1 | 10/2010 | | |
|---|---|---|---|---|
| WO | 2011/002635 A1 | 1/2011 | | |
| WO | 2011/035143 A2 | 3/2011 | | |
| WO | 2011/088015 A1 | 7/2011 | | |
| WO | 2011/088561 A1 | 7/2011 | | |
| WO | 2011/109237 A2 | 9/2011 | | |
| WO | 2011/112191 A1 | 9/2011 | | |
| WO | 2011/123609 A1 | 10/2011 | | |
| WO | 2011/140324 A1 | 11/2011 | | |
| WO | 2011/155898 A1 | 12/2011 | | |
| WO | 2012/016133 A2 | 2/2012 | | |
| WO | 2012/018635 A2 | 2/2012 | | |
| WO | 2012/033956 A1 | 3/2012 | | |
| WO | 2012/049277 A1 | 4/2012 | | |
| WO | 2012/075235 A1 | 6/2012 | | |
| WO | 2012/080050 A1 | 6/2012 | | |
| WO | 2012/117216 A1 | 9/2012 | | |
| WO | 2012/136834 A1 | 10/2012 | | |
| WO | 2013/006394 A1 | 1/2013 | | |
| WO | 2013/096744 A1 | 6/2013 | | |
| WO | 2013/102655 A1 | 7/2013 | | |
| WO | 2013/130703 A2 | 9/2013 | | |
| WO | 2013/181584 A2 | 12/2013 | | |
| WO | 2013/184757 A1 | 12/2013 | | |
| WO | 2014/033167 A1 | 3/2014 | | |
| WO | 2014/033170 A1 | 3/2014 | | |
| WO | 2014/033176 A1 | 3/2014 | | |
| WO | 2014/037480 A1 | 3/2014 | | |
| WO | 2014/106019 A2 | 7/2014 | | |
| WO | 2014/131847 A1 | 9/2014 | | |
| WO | 2014/151958 A1 | 9/2014 | | |
| WO | 2014/161888 A1 | 10/2014 | | |
| WO | 2014/184350 A1 | 11/2014 | | |
| WO | 2014/184365 A1 | 11/2014 | | |
| WO | WO 2014/184350 A1 * | 11/2014 | .......... | C07D 207/40 |
| WO | 2014/191301 A1 | 12/2014 | | |
| WO | 2014/191726 A1 | 12/2014 | | |
| WO | 2014/198880 A1 | 12/2014 | | |
| WO | 2015/011281 A1 | 1/2015 | | |
| WO | 2015/055764 A1 | 4/2015 | | |
| WO | 2015/057945 A1 | 4/2015 | | |
| WO | 2015/059212 A1 | 4/2015 | | |
| WO | 2015/073774 A1 | 5/2015 | | |
| WO | 2015/109130 A1 | 7/2015 | | |
| WO | 2015/116923 A1 | 8/2015 | | |
| WO | 2015118057 A1 | 8/2015 | | |
| WO | 2015/138895 A1 | 9/2015 | | |
| WO | 2015/144093 A1 | 10/2015 | | |
| WO | 2015/180631 A1 | 12/2015 | | |
| WO | 2016/089990 A1 | 6/2016 | | |
| WO | 2016/109663 A2 | 7/2016 | | |
| WO | 2016/109684 A2 | 7/2016 | | |
| WO | 2016/109689 A2 | 7/2016 | | |
| WO | 2016/113273 A1 | 7/2016 | | |
| WO | 2016/149581 A1 | 9/2016 | | |
| WO | 2016/161268 A1 | 10/2016 | | |
| WO | 2016/168619 A1 | 10/2016 | | |
| WO | 2016/183266 A1 | 11/2016 | | |

OTHER PUBLICATIONS

[Online] Registry via STN, May 6, 2011, RN 1291044-81-9.
[Online] Registry via STN, Oct. 7, 2008, RN 1057788-44-9.
[Online] Registry via STN, Oct. 7, 2008, RN 1057871-39-2.
[Online] Registry via STN, Aug. 15, 2011, RN 1317923-24-2.
[Online] Registry via STN, Aug. 15, 2011, RN 1318022-74-0.
[Online] Registry via STN, May 18, 2011, RN 1296380-95-4.
[Online] Registry via STN, Oct. 18, 2000, RN 296894-70-7.
[Online] Registry via STN, Sep. 20, 2013, RN 1452780-00-5.
Bennes et al. (2001) "Recognition-induced control and acceleration of a pyrrole Diels-Alder reaction," Tetrahedron Letters. 42(12):2377-2380.
Berke et al. (Oct. 2016) "Caspid assembly modulator JNJ-56136379 prevents de novo infection of primary human hepatocytes with hepatitis B virus," In; The Abstracts of the Liver Meeting 2016 (AASLD). Boston, MA. p. 124A. Abstract 234.
Cai et al. (Aug. 2012) "Identification of Disubstituted Sulfonamide Compounds as specific Inhibitors of Hepatitis B Virus Covalently Closed Circular DNA Formation," Antimicrobial Agents and Chemotherapy. 56(8):4277-4288.
Campagna et al. (Apr. 10, 2013) "Sulfonamoylbenzamides Derivatives Inhibit the Assembly of Hepatitis B virus in Nucleocapsids," J. Virol. 87(12):6931-6942.
Duan et al. (2009) "2-Phenylquinazolin-4(3H)-one, a class of potent PDE5 inhibitors with high selectivity versus PDE6," Bioorganic and Medicinal Chemistry. 19(10):2777-2779.
El-Sayed (1998) "A Comparative Study of the Reactions of Thiophene-2-Carboxanilides and Related Compounds," Chemistry of Heterocyclic Compounds. 34(7):796-801.
El-Sharief et al. (1987) "Synthesis of different types of chlorinated sulfonamides with expected insecticidal and bactericidal activities," Proceedings of the Indian National Science Academy, Part A: Physical Sciences. 53 (1):179-188.
Ermann et al. (2008) "Arylsulfonamide CB2 receptor agonists: SAR and optimization of CB2 selectivity," Bioorganic & Medicinal Chemistry Letters. 18(5):1725-1729.
Extended European Search Report corresponding to European Patent Application No. 12182076, dated Apr. 19, 2013.
Extended European Search Report corresponding to European Patent Application No. 13157232, dated Apr. 5, 2013.
Extended European Search Report corresponding to European Patent Application No. 13162131, dated Sep. 11, 2013.
Extended European Search Report corresponding to European Patent Application No. 13168291, dated Jun. 20, 2013.
Extended European Search Report corresponding to European Patent Application No. 13168295, dated Oct. 7, 2013.
Extended European Search Report corresponding to European Patent Application No. 13169574, dated Aug. 19, 2013.
Geies (1991) "Synthesis of Some Thiazolo-[3, 2=A]Pyrimidines," Phosphorous, Sulfur and Silicon and the Related Elements. 56(1-4):87-93.
Hogan (2009) "Aqueous Process Chemistry: The Preparation of Aryl Sulfonyl Chlorides," Organic Process Research and Development 13(5):875-879.
International Search Report with Written Opinion corresponding to International Patent Application No. PCT/EP2013/067821, dated Nov. 28, 2013.
International Search Report with Written Opinion corresponding to International Patent Application No. PCT/EP2013/067829, dated Jan. 10, 2014.
International Search Report with Written Opinion corresponding to International Patent Application No. PCT/EP2014/053858, dated May 28, 2014.
International Search Report with Written Opinion corresponding to International Patent Application No. PCT/EP2014/056601, dated Jun. 13, 2014.
International Search Report with Written Opinion corresponding to International Patent Application No. PCT/EP2014/060102, dated Jul. 7, 2014.
International Search Report with Written Opinion corresponding to International Patent Application No. PCT/EP2014/060132, dated Jun. 16, 2014.
International Search Report with Written Opinion corresponding to International Patent Application No. PCT/US2012/071195, dated Apr. 26, 2013.
International Search Report with Written Opinion corresponding to International Patent Application No. PCT/US2014/024509, dated Oct. 22, 2014.
International Search Report with Written Opinion corresponding to International Patent Application No. PCT/US2015/011663, dated Apr. 29, 2015.
International Search Report with Written Opinion corresponding to International Patent Application No. PCT/US2015/014663, dated Apr. 29, 2015.
International Search Report with Written Opinion corresponding to International Patent Application No. PCT/US2016/023066, dated May 11, 2016.

(56) References Cited

OTHER PUBLICATIONS

International Search Report with Written Opinion corresponding to International Patent Application No. PCT/US2016/054424, dated Nov. 21, 2016.

Kim et al. (Apr. 9, 2011) "Discovery of novel HCV polymerase inhibitors using pharmacophore-based virtual screening," Bioorganic and Medicinal Chemistry. 21(11):3329-3334.

Lambeng et al. (2007) "Arylsulfonamides as a new class of cannabinoid CB1 receptor ligands: Identification of a lead and initial SAR studies," Bioorganic & Medicinal Chemistry Letters. 17(1):272-277.

Lau et al. (2005) "Peginterferon Alfa-2a, Lamivudine, and the Combination for HBeAg-Positive Chronic Hepatitis B," The New England Journal of Medicine. 352(26):2682-2695.

Liaw et al. (2009) "Hepatitis B virus infection," Lancet. 373:582-592.

Mabrouck (2012) "Discovering Best Candidates for Hepatocellular Carcinoma (FICC) by in-Silica Techniques and Tools," International Journal of Bioinformatics Research and Applications. 8(1-2):141-152.

Marcellin et al. (2004) "Peginterferon Alfa-2a Alone, Lamivudine Alone, and the Two in Combination in Patients with HBeAg-Negative Chronic Hepatitis B," New Engl. J. Med. 351(12):1206-1217.

Mohamed et al. (1986) "Synthesis of different types of chlorinated sulfonamides with expected insecticidal and antimicrobial activities," Acta Pharmaceutica Jugoslavica. 36(3):301-310.

Patani et al. (1996) "Bioisosterism: A Rational Approach in Drug Design," Chem. Rev. 96:3147-3176.

Patel et al. (2005) "Synthesis N-ethylpiperazinyl Sulfonyl Group Incorporated Benzamides" Indian Journal of Heterocyclic Chemistry. 15:201-202.

Search Report with Written Opinion corresponding to Singapore Patent Application No. 11201402660Y, completed May 22, 2015.

Supplementary European Search Report corresponding to European Patent Application No. 12859684, dated May 27, 2015.

Taylor et al. (Mar. 3, 2011) "A Brain-Permeable Small Molecule Reduces Neuronal Cholesterol by Inhibiting Activity of Sirtuin 2 Deacetylase," ACS Chemical Biology. 6:540-546.

The Merck Index (2013) "Infliximab," An Encyclopedia of Chemicals, Drugs and Biologicals. 14th Ed. p. 924.

The Merck Index (2013) "Zidovudine," An Encyclopedia of Chemicals, Drugs and Biologicals. 14th Ed. p. 1885.

Thompson et al. (2007) "Toll-like receptors, RIG-I-like RNA helicases and the antiviral innate immune response," Immunology and Cell Biology. 85:435-445.

Weber et al. (2002) "Inhibition of human hepatitis B virus (HBV) by a novel non-nucleosidic compound in a transgenic mouse model," Antiviral Res. 54:69-78.

West (1984) Solid State Chemistry and its Applications. John Wiley & Sons. pp. 33-36.

Yarmolchuk (2011) "Synthesis of β-fluoro-β-proline," Tetrahedron Letters. 51(12):1300-1302.

Zhang et al. (2005) "A Potent Small Molecule Inhibits Polyglutamine Aggregation in Huntington's Disease Neurons and Suppresses Neurodegeneration in vivo," Proc. Natl. Acad. Sci. USA. 102(3):892-897.

[Online] Registry via SciFinfer, Feb. 13, 2017, RN 1208400-27-4.

Brahmania (Jan. 13, 2016) "New therapeutic agents for chronic hepatitis B," Lancet Infect. Dis. 16(2):e10-e21.

Brezillon et al. (2011) "Antiviral activity of Bay 41-4109 on hepatitis B virus in humanized Alb-uPA/SCID mice," PLoS One. 6:e25096. pp. 1-6.

Chang et al. (2007) "NMR-spectroscopy-based metabonomic approach to the analysis of Bay41-4109, a novel anti-HBV compound, induced hepatotoxicity in rats," Tox. Letters. 173:161-167.

Cho et al. (Dec. 25, 2013) "2-amino-N-(2,6-dichloropyridin-3-yl)acetamide derivatives as a novel class of HBV capsid assembly inhibitor," Viral Hep. 21:843-852.

Cowie et al. (Jun. 11, 2013) "Mortality due to viral hepatitis in the Global Burden of Disease Study 2010: new evidence of an urgent global public health priority demanding action," Antivir. Ther. 18:953-954.

Delaney et al. (2002) "Phenylpropenamide derivatives AT-61 and AT-130 inhibit replication of wild-type and lamivudine-resistant strains of hepatitis B virus in vitro," Antimicrob. Agents Chemother. 46:3057-3060.

Deres et al. (2003) "Inhibition of hepatitis B virus replication by drug-induced depletion of nucleocapsids," Science. 299:893-896.

Gane (2014) "Phase 1a Saftey and Pharmacokinetics of NVR 3-778, a Potential First-in-Class HBV Core Inhibitor," In; The Abstracts of the Liver Meeting 2014 (AASLD). Boston, MA. Abstract LB-19.

Guo (2011) "HBc binds to the CpG islands of HBV cccDNA and promotes an epigenetic permissive state," Epigenetics. 6:720-726.

Huang et al. (Oct. 2016) "Blockage of HBV Virus Replication and Inhibition of cccDNA Establishment by Core Protein Allosteric Modifiers (CpAMs)," In; The Abstracts of the Liver Meeting 2016 (AASLD). Boston, MA. pp. 937A-938A. Abstract 1897.

Katen et al. (Jul. 18, 2013) "Assembly-directed antivirals differentially bind quasiequivalent pockets to modify hepatitis B virus capsid tertiary and quaternary structure," Structure. 21(8):1406-1416.

Klumpp et al. (2015) "O115: High antiviral activity of the HBV core inhibitor NVR 3-778 in the humanized uPA/SCID mouse model," J. Hepatol. 62:S250.

Klumpp et al. (Nov. 23, 2015) "High-resolution crystal structure of a hepatitis B virus replication inhibitor bound to the viral core protein," Proc. Natl. Acad. Sci. 112:15196-15201.

Lam et al. (Oct. 2015) "Inhibition of Hepatitis B Virus Replication by the HBV Core Inhibitor NVR 3-778," In; The Abstracts of the Liver Meeting 2015 (AASLD). San Francisco, CA. p. 223A. Abstract 33.

Lam et al. (Oct. 2016) "HBV Core Assembly Modulators Block Antigen Production when Present during Infection, but not during Persistent Infection," In; The Abstracts of the Liver Meeting 2016 (AASLD). Boston, MA. p. 913A. Abstract 1850.

Lam et al. (Sep. 2016) "Serum HBV RNA as a Pharmacodynamic (PD) Marker of HBV Treatment Response to Core Assembly Modulator NVR 3-778 and Pegylated-Interferon Alpha," Poster Presented In; The AASLD/EASL HBV Treatment Endpoints Workshop. Alexandria, VA. Sep. 8-9, 2016. Poster No. 3774.

Lucifora et al. (Feb. 20, 2014) "Specific and nonhepatotoxic degradation of nuclear hepatitis B virus cccDNA," Science. 343:1221-1228.

Manzoor et al. (Nov. 28, 2015) "Hepatitis B virus therapy: What's the future holding for us?" World J Gastro. 21:12558-12575.

Qiu et al. (Aug. 10, 2016) "Design and Synthesis of Orally Bioavailable 4-Methyl Heteroaryldihydropyrimidine Based Hepatitis B Virus (HBV) Capsid Inhibitors," J. Med. Chem. 59:7651-7666.

Stray et al. (2005) "A heteroaryldihydropyrimidine activates and can misdirect hepatitis B virus capsid assembly," Proc. Natl. Acad. Sci. USA. 102:8138-8143.

Stray et al. (2006) "BAY 41/4109 has multiple effects on Hepatitis B virus capsid assembly," J. Mol. Recognit. 19:542-548.

Tan et al. (Jan. 2, 2013) "Genetically altering the thermodynamics and kinetics of hepatitis B virus capsid assembly has profound effects on virus replication in cell culture," J. Vir. 87:3208-3216.

Wang et al. (Jun. 6, 2012) "In vitro inhibition of HBV replication by a novel compound, GLS4, and its efficacy against adefovir-dipivoxil-resistant HBV mutations," Antiviral therapy 17:793-803.

Wang et al. (May 28, 2016) "Serum hepatitis B virus RNA is encapsidated pregenome RNA that may be associated with persistence of viral infection and rebound," J. Hepatol. 65:700-710.

Wu et al. (Aug. 19, 2013) "Preclinical characterization of GLS4, an inhibitor of hepatitis B virus core particle assembly," Antimicrob. Agents Chemother. 57:5344-5354.

Yang et al. (2016) "Effect of a hepatitis B virus inhibitor, NZ-4, on capsid formation," Antiviral Res. 125:25-33.

Yang et al. (Feb. 3, 2014) "Isothiafludine, a novel non-nucleoside compound, inhibits hepatitis B virus replication through blocking pregenomic RNA encapsidation," Acta Pharmacol. Sin. 35:410-418.

(56) References Cited

OTHER PUBLICATIONS

Yogaratnam et al. (Oct. 2016) "Safety, Tolerability and Pharmacokinetics of JNJ-56136379, a Novel HBV Caspid Assembly Modulator, in Healthy Subjects," In; The Abstracts of the Liver Meeting 2016 (AASLD). Boston, MA. pp. 930A-931A. Abstract 1881.

Yuen et al. (Apr. 2016) "NVR 3-778, a first-in-class HBV CORE inhibitor, alone and incombination with Peg-interferon (PEGIFN), in treatment naive HBeAg-Positive patients: early reductions in HBV DNA and HBeAg," In; The Abstracts of the International Liver Congress (EASL). pp. S210-S211. Abstract LB-06.

Yuen et al. (Oct. 2015) "Phase 1b Efficacy and Safety of NVR 3-778, a First-In-Class HBV Core Inhibitor, in HBeAg-Positive Patients with Chronic HBV Infection," In; The Abstracts of the Liver Meeting 2015 (AASLD). San Francisco, CA. pp. 1385A-1386A. Abstract LB-10.

Zlotnick et al. (Jun. 27, 2015) "Core protein: A pleiotropic keystone in the HBV lifecycle," Antiviral Research. 121:82-93.

Zoulim et al. (Jun. 15, 2016) "Current treatments for chronic hepatitis B virus infections," Curr. Opin. Virol. 18:109-116.

International Search Report and Written Opinion for International Application No. PCT/EP2015/052389, dated Mar. 31, 2015.

International Search Report and Written Opinion for International Application No. PCT/US2017/027802, dated Dec. 15, 2017.

Horig et al. (2004) "From bench to clinic and back: Perspective on the 1st IQPC Translational Research conference," Journal of Translational Medicine, 2(44):1-8.

Mohebbi et al. (2018) "An overview of hepatitis B Virus surface antigen secretion inhibitors," Frontiers in Microbiology, 9(662)1-9.

Nathans et al. (2008) "Small molecule inhibition of HIV-1 vif," Nature Biotechnology 26(10):1187-1192.

Schafer et al. (2008) "Failure is an option: learning from unsuccessful proof-of-concept trials," Drug Discovery Today, 13(21/22):913-916.

U.S. Appl. No. 13/723,869 / 2013/0251673 / U.S. Pat. No. 8,629,274, filed Dec. 21, 2012 / Sep. 26, 2013 / Jan. 14, 2014, George D. Hartman.

U.S. Appl. No. 14/100,219 / 2013/0251673 / U.S. Pat. No. 8,629,274, filed Dec. 9, 2012 / Jun. 26, 2014 / Jun. 23, 2015, George D. Hartman.

U.S. Appl. No. 14/134,113 / 2014/0179665 / U.S. Pat. No. 9,061,008, filed Dec. 19, 2013 / Jun. 26, 2014 / Jun. 30, 2015, George D. Hartman.

U.S. Appl. No. 14/517,606 / 2015/0152073, filed Oct. 17, 2014 / Jun. 4, 2015, George D. Hartman.

U.S. Appl. No. 14/728,126 / 2015/0259324 / U.S. Pat. No. 9,676,747, filed Jun. 2, 2015 / Sep. 17, 2015 / Jun. 13, 2017, George D. Hartman.

U.S. Appl. No. 14/206,496 / 2014/0275167 / U.S. Pat. No. 8,993,771, filed Mar. 12, 2014 / Sep. 18, 2014 / Mar. 31, 2015, George D. Hartman.

U.S. Appl. No. 14/642,393 / 2015/0174115 / U.S. Pat. No. 9,205,079, filed Mar. 9, 2015 / Jun. 25, 2015 / Dec. 8, 2015, George D. Hartman.

U.S. Appl. No. 14/931,173 / 2016/0158214 / U.S. Pat. No. 9,579,313, filed Nov. 3, 2015 / Jun. 9, 2016 / Feb. 28, 2017, George D. Hartman.

U.S. Appl. No. 14/511,964 / 2015/0197493 / U.S. Pat. No. 9,169,212, filed Oct. 10, 2014 / Jul. 16, 2016 / Oct. 27, 2015, George D. Hartman.

U.S. Appl. No. 14/694,147 / 2015/0225355 / U.S. Pat. No. 9,505,722, filed Apr. 23, 2015 / Aug. 13, 2015 / Nov. 29, 2016, George D. Hartman.

U.S. Appl. No. 14/597,814 / 2015/0197533 / U.S. Pat. No. 9,181,288, filed Jan. 15, 2015 / Jul. 16, 2015 / Nov. 10, 2015, George D. Hartman.

U.S. Appl. No. 14/856,761 / 2016/0000812 / U.S. Pat. No. 9,339,510, filed Sep. 17, 2015 / Jan. 7, 2016 / May 17, 2016, George D. Hartman.

U.S. Appl. No. 15/277,421 / 2017/0015629, filed Sep. 27, 2016 / Jan. 19, 2017, George D. Hartman.

U.S. Appl. No. 14/670,001 / 2015/0274652 / U.S. Pat. No. 9,400,280, filed Mar. 26, 2015 / Oct. 1, 2015 / Jul. 26, 2016, George D. Hartman.

U.S. Appl. No. 14/615,292 / 2015/0216938, filed Feb. 5, 2015 / Aug. 6, 2015, George D. Hartman.

U.S. Appl. No. 15/284,807 / 2017/0182021, filed Oct. 4, 2016 / Jun. 29, 2017, George D. Hartman.

U.S. Appl. No. 15/073,965 / 2016/0272599, filed Mar. 18, 2016 / Sep. 22, 2016, George D. Hartman.

U.S. Appl. No. 15/280,321 / 2017/0114018, filed Sep. 29, 2016 / Apr. 27, 2017, George D. Hartman.

U.S. Appl. No. 15/488,368, filed Apr. 14, 2017, George D. Hartman.

\* cited by examiner

SEQUENCE LISTING

```
<160> NUMBER OF SEQ ID NOS: 3

<210> SEQ ID NO 1
<211> LENGTH: 3215
<212> TYPE: DNA
<213> ORGANISM: Artificial Sequence
<220> FEATURE:
<223> OTHER INFORMATION: Synthetic DNA Sequence

<400> SEQUENCE: 1
aactccacca ctttccacca aactcttcaa gatcccagag tcagggccct gtactttcct      60
gctggtggct ccagttcagg aacagtgagc cctgctcaaa atactgtctc tgccatatcg     120
tcaatcttat cgaaaactgg ggaccctgta ccgaacatgg agaacatcgc atcaggactc     180
ctaggacccc tgctcgtgtt acaggcgggg tttttcttgt tgacaaaaat cctcacaata     240
ccacagagtc tagactcgtg gtggacttct ctcaattttc taggggggaac acccgtgtgt     300 cttggccaaa attcgcagtc ccaaatctcc agtcactcac caacctgttg tcctccaatt     360
tgtcctggtt atcgctggat gtatctgcgg cgttttatca tattcctctg catcctgctg     420
ctatgcctca tcttcttgtt ggttcttctg gactatcaag gtatgttgcc cgtttgtcct     480
```

-continued

```
ctaattccag gatcatcaac aaccagcacc ggaccatgca aaacctgcac gactcctgct       540
caaggaacct ctatgtttcc ctcatgttgc tgtacaaaac ctacgacgg aaactgcacc        600 tgtattccca tcccatcatc ttgggctttc gcaaaattcc tatgggagtg ggcctcagtc      660
cgtttctctt ggctcagttt actagtgcca tttgttcagt ggttcgtagg gctttccccc     720
actgtctggc tttcagttat atggatgatt tggttttggg ggccaagtct gtacaacatc      780
ttgagtccct ttatgccgct gttaccaatt ttcttttgtc tttgggtata catttaaacc     840
ctcacaaaac aaaaagatgg ggatattccc ttaactttat gggatatgta attgggagtt    900
ggggcacatt gccacaggaa catattgtac aaaaaatcaa aatatgtttt aggaaacttc   960
ctgtaaacag gcctattgat tggaaagtct gtcaacgaat tgtgggtctt ttgggggtttg  1020 ccgccccttt cacgcaatgt ggatatcctg ctttaatgcc tttatatgca tgtatacaag   1080
caaaacaggc ttttattttc tcgccaactt acaaggcctt tctgagtaaa cagtatttga    1140
acctttaccc cgttgctcgg caacggcctg gtctgtgcca agtgtttgct gacgcaaccc   1200
ccactggttg gggcttggcc ataggccatc agcgcatgcg tggcaccttt gtgtctcctc    1260
tgccgatcca tactgcggaa ctcctagccg cttgttttgc tcgcagcagg tctggggcaa    1320
aactcatcgg gactgacaat tctgtcgtgc tctcccgcaa gtatacatca tttccatggc    1380
tgctaggctg tgctgccaac tggatcctgc gcgggacgtc ctttgtttac gtcccgtcgg   1440 ccgctgaatcc cgcggacgac ccctcccggg gccgcttggg gctctaccgc ccgcttctcc   1500
gcctgttgta ccgaccgacc acggggcgca cctctctta cgcggactcc ccgtctgtgc    1560
cttctcatct gccggaccgt gtgcacttcg cttcacctct gcacgtcgca tggaaaccac  1620
cgtgaacgcc cacaggaacc tgcccaaggt cttgcataag aggactcttg gactttcagc    1680
aatgtcaacg accgaccttg aggcatactt caaagactgt gtgtttactg agtggggaga    1740
gttgggggag gaggttaggt taatgatctt tgtactagga ggctgtaggc ataaattggt   1800
gtgttcacca gcaccatgca acttttttcac ctctgcctaa tcatctcatg ttcatgtcct   1860
actgttcaag cctccaagct gtgccttggg tggctttggg gcatggacat tgacccgtat  1920
aaagaatttg gagcttctgt ggagttactc tctttttttgc cttctgactt ctttccttct  1980
attcgagatc tcctcgacac cgcctctgct ctgtatcggg aggccttaga gtctccggaa   2040
cattgttcac ctcaccatac ggcactcagg caagctattc tgtgttgggg tgagttaatg    2100
aatctagcca cctgggtggg aagtaatttg gaagatccag catccaggga attagtagtc   2160
agctatgtca acgttaatat gggcctaaaa atcagacaac tattgtggtt tcacatttcc    2220
tgtcttactt ttgggagaga aactgttctt gaatatttgg tgtcttttgg agtgtggatt   2280
cgcactcctc ccgcatatag accgccaaat gcccctatct tatcaacact tccggaaact   2340
actgttgtta gacgaagagg caggtcccct agaagaagaa ctccctcgcc tcgcagacga   2400
aggtctcaat cgccgcgtcg cagaagatct caatctcggg aatctcaatg ttagtattcc    2460
ttggacacac aaggtgggaa actttacggg gctttattct tctacggtac cttgctttaa    2520
tcctaaatgg caaactcctt cttttcctga cattcatttg caggaggaca ttgttgatag   2580
atgtaagcaa tttgtgggc cccttacagt aaatgaaaac aggagactta aattaattat     2640
gcctgctagg ttttatccca atgttactaa atatttgccc ttagataaag ggatcaaacc    2700
gtattatcca gagtatgtag ttaatcatta cttccagacg cgacattatt tacacactct    2760
ttggaaggcg gggatcttat ataaaagaga gtccacacgt agcgcctcat tttgcgggtc     2820
accatattct tgggaacaag atctacagca tgggaggttg gtcttccaaa cctcgaaaag    2880
```

| | |
|---|---|
| gcatggggac aaatctttct gtccccaatc ccctgggatt cttccccgat catcagttgg | 2940 |
| accctgcatt caaagccaac tcagaaaatc cagattggga cctcaacccg cacaaggaca | 3000 |
| actggccgga cgccaacaag gtgggagtgg gagcattcgg gccagggttc accctcccc | 3060 |
| atggggact gttgggtgg agccctcagg ctcaggcct actcacaact gtgccagcag | 3120 |
| ctcctcctcc tgcctccacc aatcggcagt taggaaggca gcctactccc ttatctccac | 3180 |
| ctctaaggga cactcatcct caggccatgc agtgg | 3215 |

<210> SEQ ID NO 2
<211> LENGTH: 3215
<212> TYPE: DNA
<213> ORGANISM: Artificial Sequence
<220> FEATURE:
<223> OTHER INFORMATION: Synthetic DNA Sequence

<400> SEQUENCE: 2

| | |
|---|---|
| aactccacca ctttccacca aactcttcaa gatcccagag tcagggccct gtactttcct | 60 |
| gctggtggct ccagttcagg aacagtgagc cctgctcaga atactgtctc tgccatatcg | 120 |
| tcaatcttat cgaagactgg ggaccctgta ccgaacatgg agaacatcgc atcaggactc | 180 |
| ctaggacccc tgctcgtgtt accggcgggg ttttccttgt tgacaaaaat cctcacaata | 240 |
| ccacagagtc tagactcgtg gtggacttct ctcagttttc taggggaac accgtgtgt | 300 |
| cgtggccaaa attcgcagtc ccaaatctcc agtcactcac caacctgttg tcctccaatt | 360 |
| tgtcctggtt atcgctggat gtgtctgcgg cgttttatca tattcctctg catcctgctg | 420 |
| ctatgcctca tcttcttgtt ggttcttctg gactatcaag gtatgttgcc cgtttgtcct | 480 |
| ctaattccag gatcatcaac aaccagcacc ggaccatgca aaacctgcac gactcctgct | 540 |
| caaggaacct ctatgtttcc ctcatgttgc tgtacaaaac ctacggacgg aaactgcacc | 600 |
| tgtattccca tcccatcatc ttgggctttc gcaaaattcc tatgggagtg ggcctcagtc | 660 |
| cgtttctcat ggctcagttt actagtgcca tttgttcagt ggttcgtagg gctttccccc | 720 |
| actgtctggc tttcagttat gtggatgatt tggttttggg ggccaagtct gtacaacatc | 780 |
| ttgagtccct ttatgccgct gttaccaatt tctttttgtc tttgggtata catttaaacc | 840 |
| ctcacaaaac aaaaagatgg ggatattccc ttaacttcat gggatatgta attgggagtt | 900 |
| ggggcacatt gccacaggaa catattgtac aaaaaatcaa aatgtgtttt aggaaacttc | 960 |
| ctgtaaacag gcctattgat tggaaagtct gtcaacgaat tgtgggtctt ttggggtttg | 1020 |
| ccgccccttt cacgcaatgt ggatatcctg ctttaatgcc tttatatgca tgtatacaag | 1080 |
| caaaacaggc tttatttttc tcgccaactt acaaggcctt tctgagtaaa cagtatctga | 1140 |
| acctttaccc cgttgctcgg caacggcctg gtctgtgcca agtgtttgct gacgcaaccc | 1200 |
| ccactggttg ggcttggcc ataggccatc agcgcatgcg tggaaccttt gtgtctcctc | 1260 |
| tgccgatcca tactgcggaa ctcctagccg cttgttttgc tcgcagcagg tctggggcaa | 1320 |
| aactcatcgg gactgacaat tctgtcgtgc tctcccgcaa gtatacatca tttccatggc | 1380 |
| tgctaggctg tgctgccaac tggatcctgc gcgggacgtc ctttgtttac gtcccgtcgg | 1440 |
| cgctgaatcc cgcggacgac ccctcccggg gccgcttggg gctctaccgc ccgcttctcc | 1500 |
| gcctgttgta ccgaccgacc acggggcgca cctctcttta cgcggactcc ccgtctgtgc | 1560 |
| cttctcatct gccggaccgt gtgcacttcg cttcacctct gcacgtcgca tggaaaccac | 1620 |
| cgtgaacgcc cactggaacc tgcccaaggt cttgcataag aggactcttg gactttcagc | 1680 |

```
aatgtcaacg accgaccttg aggcatactt caaagactgt gtgttcaatg agtgggagga    1740
gttgggggag gagtttaagt taatgatctt tgtactagga ggctgtaggc ataaattggt    1800
gtgttcacca gcaccatgca acttttt cac ctctgcctaa tcatctcttg ttcatgtcct   1860
actgttcaag cctccaagct gtgccttggg tggctttagg gcatggacat tgacacgtat    1920
aaagaatttg gagcttctgt ggaattactc tcttttttgc cttctgactt ctttccttct    1980
attcgagatc tcctcgacac cgccactgct ctgtatcggg aggccttaga gtctccggaa    2040
cattgttcac ctcaccatac ggcactcagg caagctattc tgtgttgggg tgagttaatg    2100
aatctagcca cctgggtggg aagtaatttg gaagatcaag catccaggga tttagtagtc    2160
ggctatgtca acgttaatat gggcctaaaa ctcagacaac tattgtggtt tcacatttcc    2220
tgtcttactt ttggaagaga aactgttctt gaatatttgg tgtcttttgg agtgtggatt    2280
cgcactcctc ccgcatatag accgccaaat gccctatct tatcaacact tccggaaact     2340
actgttgtta gacgaagagg caggtcccct agaagaagaa ctccctcgcc tcgcagacga    2400
aggtctcaat cgccgcgtcg cagaagatct aaatctcggg aatctcaatg ttagtattcc    2460
ttggacacac aaggtgggaa actttacggg gctttattct tctacggtac cttgctttaa    2520
tcctaaatgg caaactcctt cttttcctga cattcatttg caggaggaca ttgttgatag    2580
atgtaagcaa tttgtggggc cccttacagt aaatgaaaat aggagactta aattaattat    2640
gcctgctagg ttttatccca atgttactaa atatttgccc ttagataaag ggatcaaacc    2700
gtattatcca gagtatgtag ttgatcatta cttccagacg cgacattatt tacacactct    2760
ttggaaggcg gggatcttat ataaaagaga gtccacacgt agcgcctcat tttgcgggtc    2820
accatattct tgggaacaag atctacagca tgggaggttg gtcttccaaa cctcgaaaag    2880
gcatggggac aaatctttct gtccccaatc ccctgggatt cttccccgat catcagttgg    2940
accctgcatt caaagccaac tcagaaaatc cagattggga cctcaacccg tacaaggaca    3000 actgccgga cgccaacaag gtgggagtgg gagcattcgg gccagggttc acccctcccc     3060
atgggggact gttgggttgg agccctcagg ctcagggtct actcacaact gtgccagcag    3120
ctcctcctcc tgcctccacc aatcggcagt taggaaggca gcctactccc ttatctccac    3180
ctctaaggga cactcatcct caggccatac agtgg                               3215
```

<210> SEQ ID NO 3
<211> LENGTH: 3215
<212> TYPE: DNA
<213> ORGANISM: Artificial Sequence
<220> FEATURE:
<223> OTHER INFORMATION: Synthetic DNA Sequence

<400> SEQUENCE: 3

```
aactccacca ctttccacca aactcttcaa gatcccagag tcagggccct gtactttcct      60
gctggtggct ccagttcagg aacagtgagc cctgctcaga atactgtctc tgccatatcg     120
tcaatcttat cgaagactgg ggaccctgta ccgaacatgg agaacatcgc atcaggactc     180
ctaggacccc tgctcgtgtt accggcgggg ttttccttgt tgacaaaaat cctcacaata     240
ccacagagtc tagactcgtg gtggacttct ctcagttttc taggggaac acccgtgtgt     300 cgtggccaaa attcgcagtc ccaaatctcc agtcactcac caacctgttg tcctccaatt    360
tgtcctggtt atcgctggat gtgtctgcgg cgttttatca tattcctctg catcctgctg    420
ctatgcctca tcttcttgtt ggttcttctg gactatcaag gtatgttgcc cgtttgtcct    480
ctaattccag gatcatcaac aaccagcacc ggaccatgca aaacctgcac gactcctgct    540
```

```
caaggaacct ctatgtttcc ctcatgttgc tgtacaaaac ctacggacgg aaactgcacc    600
tgtattccca tcccatcatc ttgggctttc gcaaaattcc tatgggagtg ggcctcagtc    660
cgtttctcat ggctcagttt actagtgcca tttgttcagt ggttcgtagg gctttccccc    720
actgtctggc tttcagttat gtggatgatt tggttttggg ggccaagtct gtacaacatc    780
ttgagtccct ttatgccgct gttaccaatt ttcttttgtc tttgggtata catttaaacc    840
ctcacaaaac aaaagatggg ggatattccc ttaacttcat gggatatgta attgggagtt    900
ggggcacatt gccacaggaa catattgtac aaaaaatcaa aatgtgtttt aggaaacttc    960
ctgtaaacag gcctattgat tggaaagtct gtcaacgaat tgtgggtctt ttggggtttg   1020
ccgccccttt cacgcaatgt ggatatcctg ctttaatgcc tttatatgca tgtatacaag   1080
caaaacaggc ttttattttc tcgccaactt acaaggcctt tctgagtaaa cagtatctga   1140
acctttaccc cgttgctcgg caacggcctg gtctgtgcca agtgtttgct gacgcaaccc   1200
ccactggttg gggcttggcc ataggccatc agcgcatgcg tggaaccttt gtgtctcctc   1260
tgccgatcca tactgcggaa ctcctagccg cttgttttgc tcgcagcagg tctggggcaa   1320
aactcatcgg gactgacaat tctgtcgtgc tctcccgcaa gtatacatca tttccatggc   1380
tgctaggctg tgctgccaac tggatcctgc gcgggacgtc ctttgtttac gtcccgtcgg   1440
cgctgaatcc cgcggacgac ccctcccggg gccgcttggg gctctaccgc ccgcttctcc   1500
gcctgttgta ccgaccgacc acggggcgca cctctcttta cgcggactcc ccgtctgtgc   1560
cttctcatct gccggaccgt gtgcacttcg cttcacctct gcacgtcgca tggaaaccac   1620
cgtgaacgcc cactggaacc tgcccaaggt cttgcataag aggactcttg gactttcagc   1680
aatgtcaacg accgaccttg aggcatactt caaagactgt gtgttcaatg agtgggagga   1740
gttgggggag gagtttaagt taatgatctt tgtactagga ggctgtaggc ataaattggt   1800
gtgttcacca gcaccatgca acttttttcac ctctgcctaa tcatctcttg ttcatgtcct   1860
actgttcaag cctccaagct gtgccttggg tggctttagg gcatggacat tgacacgtat   1920
aaagaatttg gagcttctgt ggaattactc tcttttttgc cttctgactt ctttccttct   1980
attcgagatc tcctcgacac cgccactgct ctgtatcggg aggccttaga gtctccggaa   2040
cattgttcac ctcaccatac ggcactcagg caagctattc tgtgttgggg tgagttaatg   2100
aatctagcca cctgggtggg aagtaatttg gaagatcaag catccaggga tttagtagtc   2160
ggctatgtca acgttaatat gggcctaaaa ctcagacaac tattgtggtt tcacatttcc   2220
tgtcttactt ttggaagaga aactgttctt gaatatttgg tgtcttttgg agtgtggatt   2280
cgcactcctc ccgcatatag accgccaaat gcccctatct tatcaacact tccggaaact   2340
actgttgtta gacgaagagg caggtcccct agaagaagaa ctccctcgcc tcgcagacga   2400
aggtctcaat cgccgcgtcg cagaagatct aaatctcggg aatctcaatg ttagtattcc   2460
ttggacacac aaggtgggaa actttacggg gctttattct tctacggtac cttgctttaa   2520
tcctaaatgg caaactcctt ctttttcctga cattcatttg caggaggaca ttgttgatag   2580
atgtaagcaa tttgtggggc cccttacagt aaatgaaaat aggagactta aattaattat   2640
gcctgctagg ttttatccca atgttactaa atatttgccc ttagataaag ggatcaaacc   2700
gtattatcca gagtatgtag ttgatcatta cttccagacg cgacattatt tacacactct   2760
ttggaaggcg gggatcttat ataaaagaga gtccacacgt agcgcctcat tttgcgggtc   2820
accatattct tgggaacaag atctacagca tgggaggttg gtcttccaaa cctcgaaaag   2880
```

```
gcatggggac aaatctttct gtccccaatc ccctgggatt cttccccgat catcagttgg    2940
accctgcatt caaagccaac tcagaaaatc cagattggga cctcaacccg tacaaggaca    3000
actggccgga cgccaacaag gtgggagtgg gagcattcgg gccagggttc acccctcccc    3060
atgggggact gttgggttgg agccctcagg ctcagggtct actcacaact gtgccagcag    3120
ctcctcctcc tgcctccacc aatcggcagt taggaaggca gcctactccc ttatctccac    3180
ctctaaggga cactcatcct caggccatac agtgg                               3215
```

COMBINATIONS AND METHODS COMPRISING A CAPSID ASSEMBLY INHIBITOR

CROSS REFERENCE TO RELATED APPLICATIONS

This application claims the benefit of U.S. Provisional Application No. 62/323,251, filed Apr. 15, 2016, and U.S. Provisional Application No. 62/421,035, filed Nov. 11, 2016. The contents of each of these applications are incorporated herein by reference in their entireties.

SEQUENCE LISTING

This application contains a Sequence Listing in computer readable format. The Sequence Listing is provided as a file entitled 590283_NTT-029_Sequence_Listing.txt, created Jul. 27, 2017, which is 13260 bytes in size. The information in the computer readable format of the Sequence Listing is incorporated herein by reference in its entirety.

TECHNICAL FIELD

The present disclosure relates to methods of using a capsid assembly inhibitor for the treatment of hepatitis B virus infection.

BACKGROUND

Chronic hepatitis B virus (HBV) infection is a persistent, potentially progressive necroinflammatory liver disease associated with chronic HBV infection. Worldwide about 240-400 million persons are chronically infected with HBV, and chronic HBV infection is a major global cause of severe liver morbidity and liver-related mortality (Hepatitis B Factsheet, World Health Organization, 2013; Hoofnagle J H, et al., Management of Hepatitis B: Summary of a Clinical Research Workshop, Hepatology, 2007, 45(4):1056-1075; EASL Clinical Practice Guidelines: Management of chronic hepatitis B virus infection, J. Hepatology, 2012, 57:167-185 (EASL 2012); Lesmana L A, et al. Hepatitis B: overview of the burden of disease in the Asia-Pacific region, Liver International, 2006, 26:3-10; Lok A S F and McMahon B J, Chronic Hepatitis B: Update , Hepatology, September 2009: 1-36 (Lok 2009)).

The chronic state of HBV infection in individual subjects was traditionally established by confirmation of persistent detectability of hepatitis B surface antigen (HBsAg) in subject serum for 6 months or more. The U.S. Center for Disease Control (CDC) considers a serologic profile consistent with chronic HBV infection to be: HBsAg-positive and HBsAb-negative, with detectable IgG antibody to heptatits B core antigen (IgG HBcAb) and non-detectable IgM antibody to heptatits B core antigen (IgM HBcAb). In such individuals, serum hepatitis B e antigen (HBeAg) can be detectable or non-detectable and is more likely to be detectable at later stages of chronic HBV infection.

Current regulatory-approved therapies for chronic HBV infection include parenterally-administered alpha-interferons (non-pegylated or pegylated) and various orally-administered nucleoside/nucleotide (nucleos(t)ide) inhibitors of the HBV polymerase/reverse transcriptase (HBV Pol-RT)). Each of these agents have suppressed HBV replication and induced HBeAg loss/seroconversion in only about 20-35% of HBeAg-positive patients after a year of treatment (EASL 2012; Lok 2009; Sorrell M F et al., National Institutes of Health Consensus Development Conference Statement: Management of Hepatitis B, Ann Intern Med, 2009, 150(2): 104-110; Woo G et al., Tenofovir and Entecavir Are the Most Effective Antiviral Agents for Chronic Hepatitis B: A Systematic Review and Bayesian Meta-Analyses, Gastroenterology, 2010:1-17). Although patients with chronic HBV infection who are HBeAg-positive experience up to 30-35% loss of HBeAg under current 48-week treatment regimens with pegylated interferons (PegIFNs), within 2-5 years after treatment 20-50% of patients have regressed to their original HBeAg levels (Perillo R, Benefits and Risks of Interferon Therapy for Hepatitis B, Hepatology, 2009, 49:S103-S111). Thus, current HBV therapies can provide prolonged suppression of HBV replication, but most patients fail to achieve responses that are durable post-treatment.

In contrast, suppression of HBV replication to low or non-detectable levels can be maintained for longer periods in most patients continuously treated with potent HBV nucleos(t)ides, with or without HBeAg loss or seroconversion, but such prolonged periods of nucleos(t)ide treatment are associated with risk of tolerance, viral resistance, and patient compliance difficulties (Chotiyaputta W et al., Persistence and adherence to nucleos(t)ide analogue treatment for chronic hepatitis B, J. Hepatology, 2011, 54:12-18; Lee M and Keeffe E B, Study of adherence comes to the treatment of chronic hepatitis B, J. Hepatology, January 2011, 54(1):12-18; Scaglione S J and Lok A S F, Effectiveness of Hepatitis B Treatment in Clinical Practice, Gastroenterology, 2012, 142:1360-1368).

With the continued worldwide prevalence of HBV-associated mortality and severe morbidity, there remains a need for improved HBV antiviral therapies that can achieve sustained viral response during and after treatment.

SUMMARY OF THE INVENTION

In an aspect, provided herein is a method of treating an HBV infection in a patient in need thereof, comprising administering to the patient a therapeutically effective amount of a core protein allosteric modulator (CpAM) and a reverse transcriptase inhibitor. In an embodiment, the CpAM is a core protein allosteric modulator that causes aberrant, defective or incomplete assembly of HBV capsids. In another embodiment, the CpAM is a core protein allosteric modulator that causes assembly of capsids that are essentially empty with respect to their viral contents.

In another aspect, provided herein is a method of treating an HBV infection in a patient in need thereof, comprising administering to the patient a therapeutically effective amount of a compound of Formula I

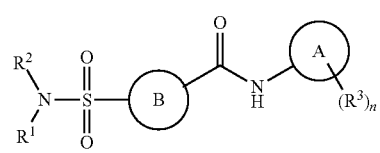

or a pharmaceutically acceptable salt thereof, hydrate thereof, solvate thereof, or a crystalline form thereof, and a reverse transcriptase inhibitor, or a pharmaceutically acceptable salt or prodrug thereof.

In yet another embodiment of this method, the compound of Formula I is a compound of Formula IA

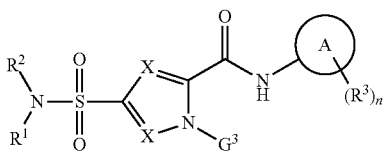

IA or a pharmaceutically acceptable salt thereof, hydrate thereof, solvate thereof, or crystalline form thereof.

In yet another embodiment of this method, the compound of Formula I is a compound of Formula IB

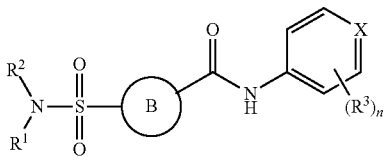

IB or a pharmaceutically acceptable salt thereof, hydrate thereof, solvate thereof, or crystalline form thereof.

In an embodiment of this method, the compound of Formula I or Formula IB is a compound of Formula II

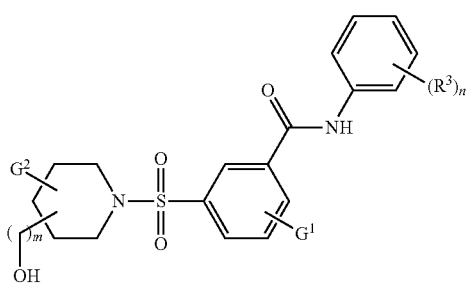

II or a pharmaceutically acceptable salt thereof, hydrate thereof, solvate thereof, or crystalline form thereof.

In another embodiment of this method, the compound of Formula I or Formula IB is a compound of Formula IIIA

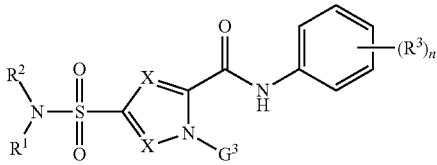

or a pharmaceutically acceptable salt thereof, hydrate thereof, solvate thereof, or crystalline form thereof.

In yet another embodiment of this method, the compound of Formula I or Formula IB is a compound of Formula IIIB

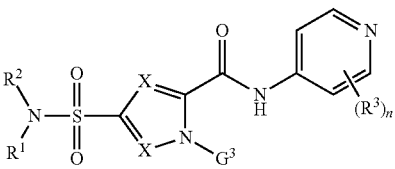

IIIB or a pharmaceutically acceptable salt thereof, hydrate thereof, solvate thereof, or crystalline form thereof.

In an aspect, provided herein is a method of treating an HBV infection in a patient in need thereof comprising administering to the patient a therapeutically effective amount of Compound 1:

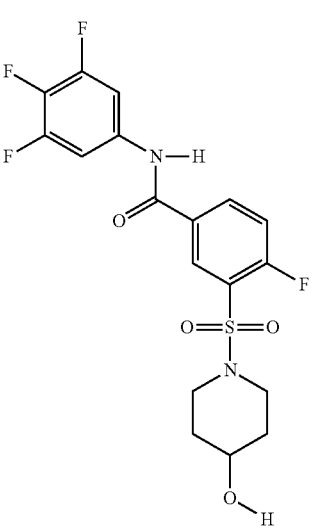 [SMILES: O=C(Nc1cc(F)c(F)c(F)c1)c1ccc(F)c(S(=O)(=O)N2CCC(O)CC2)c1]

4-fluoro-3-((4-hydroxypiperidin-1-yl)sulfonyl)-N-(3,4,5,-trifluorophenyl)benzamide or a pharmaceutically acceptable salt thereof, a hydrate thereof, solvate thereof, or a crystalline form thereof and a reverse transcriptase inhibitor, or a pharmaceutically acceptable salt, or a prodrug thereof.

In another aspect, provided herein is a method of treating an HBV infection in a patient in need thereof comprising administering to the patient a therapeutically effective amount of Compound 2:

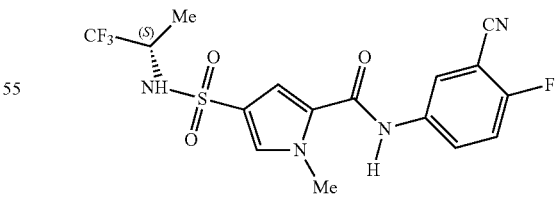

(S)—N-(3-cyano-4-fluorophenyl)-1-methyl-4-(N-(1,1,1-trifluoropropan-2-yl) sulfamoyl)-1H-pyrrole-2-carboxamide or a pharmaceutically acceptable salt thereof, a hydrate thereof, a solvate thereof, or a crystalline form thereof, and a reverse transcriptase inhibitor, or a pharmaceutically acceptable salt or a prodrug thereof.

In yet another aspect, provided herein is a method of treating an HBV infection in a patient in need thereof comprising administering to the patient a therapeutically effective amount of Compound 3:

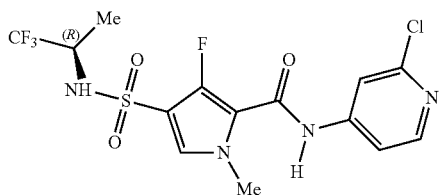

(R)—N-(2-chloropyridin-4-yl)-1-methyl-4-(N-(1,1,1-trifluoropropan-2-yl) sulfamoyl)-1H-pyrrole-2-carboxamide or a pharmaceutically acceptable salt thereof, a hydrate thereof, a solvate thereof, or a crystalline form thereof, and a reverse transcriptase inhibitor, or a pharmaceutically acceptable salt or a prodrug thereof.

In an embodiment, the reverse transcriptase inhibitor is a purine-based reverse transcriptase inhibitor such as entecavir or tenofovir.

In another embodiment, the reverse transcriptase inhibitor is selected from the group consisting of entecavir, tenofovir, lamivudine, telbivudine, adefovir, clevudine, CMX157, AGX-1009, zidovudine, didanosine, zalcitabine, stavudine, emtricitabine, abacavir, D-D4FC, alovudine, amdoxovir, elvucitabine, delavirdine, efavirenz, nevirapine, capravirine, calanolide A, TMC278, BMS-561390, and DPC-083, or prodrugs thereof and pharmaceutically acceptable salts thereof. Pharmaceutically acceptable prodrugs of tenofovir, for example, include tenofovir disoproxil fumarate and tenofovir alafenamide fumarate.

In another embodiment, the reverse transcriptase inhibitor is selected from the group consisting of entecavir, tenofovir, and lamivudine, or pharmaceutically acceptable salts, or prodrugs thereof.

In an embodiment, the CpAM and the reverse transcriptase inhibitor are in the same formulation. In another embodiment, the CpAM and the reverse transcriptase inhibitor are in separate formulations.

In another embodiment, Compound 1, Compound 2, or Compound 3 and the reverse transcriptase inhibitor are in the same formulation. In another embodiment, Compound 1, Compound 2, or Compound 3 and the reverse transcriptase inhibitor are in separate formulations.

In an embodiment, the patient is resistant or refractory to treatment with a reverse transcriptase inhibitor. In another embodiment, the patient is resistant or refractory to treatment with a nucleoside agent. In yet another embodiment, the patient is a treatment-naïve patient.

In an embodiment, Compound 1 is administered in an amount of from 50 mg per day to 3000 mg per day. In an embodiment, Compound 1 is administered in an amount of about 2000 mg per day. In a further embodiment, the Compound 1 is administered in an amount of about 1000 mg twice per day. In an embodiment, Compound 1 is administered in an amount of 1200 mg per day. In an embodiment, Compound 1 is administered in an amount of 600 mg twice per day. In an embodiment, Compound 1 is administered in an amount of 600 mg per day. In an embodiment, Compound is administered in an amount of 400 mg per day. In an embodiment, Compound 1 is administered in an amount of 200 mg per day. In an embodiment, Compound 15 is administered in an amount of 100 mg per day.

In an embodiment, Compound 2 or Compound 3 are administered in an amount of from 5 mg per day to 600 mg per day. In another embodiment, Compound 2 or Compound 3 are administered in an amount of from 10 mg per day to 50 mg per day. In a particular embodiment, Compound 2 or Compound 3 is administered in an amount of about 258 mg per day. In another embodiment, Compound 2 or Compound 3 is administered in an amount of about 25 mg four times per day. In yet another embodiment, Compound 2 or Compound 3 is administered in an amount of about 100 mg the first day and 25 mg four times per day thereafter. In a further embodiment, Compound 2 or Compound 3 is administered in an amount of 10 mg once per day to 200 mg once per day.

In an embodiment, Compound 1 is in a crystalline form. In a further embodiment, the crystalline form is characterized by an X-ray powder diffraction pattern having peaks expressed in degrees-2-theta at angles (±0.2°) of 17.1, 20.8, 22.2, 24.9, and 26.6 (Form XVI).

In another embodiment, the administration of the disclosed compounds and the reverse transcriptase inhibitor occurs over a period of time shorter than 48 weeks.

In an embodiment, the patient is a chronically HBV-infected patient.

In an aspect, provided herein is a combination product comprising a CpAM and a reverse transcriptase inhibitor. In an embodiment of the combination product, the CpAM is a core protein allosteric modulator that causes aberrant, defective or incomplete assembly of HBV capsids. In another embodiment of the combination product, the CpAM is a core protein allosteric modulator that causes assembly of capsids that are essentially empty with respect to their viral contents.

In an aspect, provided herein is a combination product comprising a CpAM, a compound of Formula I, Formula IA, Formula IB, Formula IIA, Formula IIIA or Formula IIIB or pharmaceutically acceptable salts thereof, hydrates thereof, solvates thereof, or crystalline forms thereof, and a reverse transcriptase inhibitor, or a pharmaceutically acceptable salt, or a prodrug thereof.

In an aspect, provided herein is a combination product comprising Compound 1, Compound 2, or Compound 3, or pharmaceutically acceptable salts thereof, hydrates thereof, solvates thereof, or crystalline forms thereof, and a reverse transcriptase inhibitor, or a pharmaceutically acceptable salt, or a prodrug thereof. In an embodiment of the combination product, the reverse transcriptase inhibitor is selected from the group consisting of entecavir, tenofovir and lamivudine, or a pharmaceutically acceptable salt or prodrug thereof.

In another aspect, provided herein is a combination product comprising a compound of Formula IB, or pharmaceutically acceptable salts thereof, hydrates thereof, solvates thereof, or crystalline forms thereof, and a reverse transcriptase inhibitor, or a pharmaceutically acceptable salt, or a prodrug thereof. In an embodiment of the combination product, the reverse transcriptase inhibitor is selected from the group consisting of entecavir, tenofovir and lamivudine, or a pharmaceutically acceptable salt or prodrug thereof.

In an embodiment of the combination product, the reverse transcriptase inhibitor is a purine-based reverse transcriptase inhibitor. In another embodiment of the combination product, the reverse transcriptase inhibitor is selected from the group consisting of entecavir, tenofovir, lamivudine, telbivudine, adefovir, clevudine, CMX157, AGX-1009, zidovudine, didanosine, zalcitabine, stavudine, emtricitabine, abacavir, D-D4FC, alovudine, amdoxovir, elvucitabine, delavirdine, efavirenz, nevirapine, capravirine, calanolide A, TMC278, BMS-561390, and DPC-083, or prodrugs thereof and pharmaceutically acceptable salts thereof. Pharmaceutically acceptable prodrugs of tenofovir, for example, include tenofovir disoproxil fumarate and tenofovir alafenamide fumarate.

In an embodiment of the combination product, the compound of Formula I, Formula IA, Formula IB, Formula IIA, Formula IIIA or Formula IIIB and the reverse transcriptase inhibitor are in the same formulation. In another embodiment of the combination product, the compound of Formula I, Formula IA, Formula IB, Formula IIA, Formula IIIA or Formula IIIB and the reverse transcriptase inhibitor are in separate formulations. In a further embodiment of this embodiment, the formulations are for simultaneous or sequential administration.

In an embodiment of the combination product, Compound 1, Compound 2, or Compound 3 and the reverse transcriptase inhibitor are in the same formulation. In another embodiment of the combination product, Compound 1, Compound 2, or Compound 3 and the reverse transcriptase inhibitor are in separate formulations. In a further embodiment of this embodiment, the formulations are for simultaneous or sequential administration.

In an embodiment of the combination product, the compound of Formula IB and the reverse transcriptase inhibitor are in the same formulation. In another embodiment of the combination product, the compound of Formula IB and the reverse transcriptase inhibitor are in separate formulations. In a further embodiment of this embodiment, the formulations are for simultaneous or sequential administration.

In an embodiment, the combination product is for use in the treatment of HBV infection in a patient.

In an embodiment, the combination product is for use in the treatment of HBV infection in a patient, wherein the patient is resistant to treatment with a reverse transcriptase inhibitor. In another embodiment, the combination product is for use in the treatment of HBV infection in a patient, wherein the patient is resistant to treatment with a nucleoside agent.

In an embodiment, the combination product is for use in the treatment of HBV infection in a patient, wherein the patient is treatment naïve. In an embodiment of the combination product, Compound 1 is in an amount from 600 mg to 3000 mg. In another embodiment of the combination product, Compound 1 is in an amount of about 2000 mg. In yet another embodiment of the combination product, Compound 1 is in an amount of about 1000 mg.

In an embodiment of the combination product, Compound 2 or Compound 3 is in an amount from 5 mg to 600 mg. In another embodiment of the combination product, Compound 2 or Compound 3 is in an amount from 10 mg to 50 mg. In another embodiment of the combination product, Compound 2 or Compound 3 is in an amount of about 25 mg. In yet another embodiment of the combination product, Compound 2 or Compound 3 is in an amount of about 10 mg to 200 mg. In an embodiment of the combination product, Compound 1 is in a crystalline form. In a further embodiment, the crystalline form is characterized by X-ray powder diffraction pattern having peaks expressed in degrees-2-theta at angles (±0.2°) of 17.1, 20.8, 22.2, 24.9, and 26.6 (Form XVI).

In an embodiment, the combination product is for use in the treatment of HBV infection in a patient, wherein the patient is chronically infected with HBV.

In another aspect, provided herein is a pharmaceutical composition comprising a core protein allosteric modulator (CpAM) and a reverse transcriptase inhibitor. In an embodiment of the pharmaceutical composition, the CpAM is a core protein allosteric modulator that causes aberrant, defective or incomplete assembly of HBV capsids. In another embodiment of the pharmaceutical composition, the CpAM is a core protein allosteric modulator that causes assembly of capsids that are essentially empty with respect to their viral contents.

In another aspect, provided herein is a pharmaceutical composition comprising a compound of Formula I, Formula IA, Formula IB, Formula IIA, Formula IIIA or Formula IIIB, or pharmaceutically acceptable salts thereof, hydrates thereof, solvates thereof, or crystalline forms thereof, and a reverse transcriptase inhibitor, or a pharmaceutically acceptable salt or prodrug thereof.

In another aspect, provided herein is a pharmaceutical composition comprising a compound of Formula IB, or pharmaceutically acceptable salts thereof, hydrates thereof, solvates thereof, or crystalline forms thereof, and a reverse transcriptase inhibitor, or a pharmaceutically acceptable salt or prodrug thereof.

In an embodiment of the pharmaceutical composition, the reverse transcriptase inhibitor is selected from the group consisting of entecavir, tenofovir, and lamivudine, or pharmaceutically acceptable salts or prodrugs thereof. In another embodiment, the reverse transcriptase inhibitor is a purine-based reverse transcriptase inhibitor.

In another embodiment, the pharmaceutical composition further comprises one or more pharmaceutically acceptable carriers.

In another aspect, provided herein is a pharmaceutical composition comprising Compound 1, Compound 2, or Compound 3, or pharmaceutically acceptable salts thereof, hydrates thereof, solvates thereof, or crystalline forms thereof, and a reverse transcriptase inhibitor, or a pharmaceutically acceptable salt or prodrug thereof.

In an embodiment of the pharmaceutical composition, the reverse transcriptase inhibitor is selected from the group consisting of entecavir, tenofovir, and lamivudine, or pharmaceutically acceptable salts or prodrugs thereof. In embodiments of the pharmaceutical composition, the reverse transcriptase inhibitor is a purine-based reverse transcriptase inhibitor.

In an embodiment of the pharmaceutical composition, the reverse transcriptase inhibitor is selected from the group consisting of entecavir, tenofovir, lamivudine, telbivudine, adefovir, clevudine, CMX157, AGX-1009, zidovudine, didanosine, zalcitabine, stavudine, emtricitabine, abacavir, D-D4FC, alovudine, amdoxovir, elvucitabine, delavirdine, efavirenz, nevirapine, capravirine, calanolide A, TMC278, BMS-561390, and DPC-083, or prodrugs thereof and pharmaceutically acceptable salts thereof. Pharmaceutically acceptable prodrugs of tenofovir, for example, include tenofovir disoproxil fumarate and tenofovir alafenamide fumarate.

In another embodiment, the pharmaceutical composition further comprises one or more pharmaceutically acceptable carriers.

In an aspect, provided herein is a method of treating an HBV infection in a patient in need thereof comprising administering to the patient a therapeutically effective amount of a compound of Formula I, Formula IA, Formula IB, Formula IIA, Formula IIIA or Formula IIIB, or pharmaceutically acceptable salts thereof, hydrates thereof, solvates thereof, or crystalline forms thereof, wherein the patient is resistant or refractory to treatment with a reverse transcriptase inhibitor.

In yet another aspect, provided herein is a method of treating an HBV infection in a patient in need thereof comprising administering to the patient a therapeutically effective amount of a compound of Formula I, Formula IA, Formula IB, Formula IIA, Formula IIIA or Formula IIIB, or pharmaceutically acceptable salts thereof, hydrates thereof, solvates thereof, or crystalline forms thereof, wherein the patient is resistant or refractory to treatment with a nucleoside agent.

In an aspect, provided herein is a method of treating an HBV infection in a patient in need thereof comprising administering to the patient a therapeutically effective amount of Compound 1, Compound 2, or Compound 3, or pharmaceutically acceptable salts thereof, hydrates thereof, solvates thereof, or crystalline forms thereof, wherein the patient is resistant or refractory to treatment with a reverse transcriptase inhibitor.

In yet another aspect, provided herein is a method of treating an HBV infection in a patient in need thereof comprising administering to the patient a therapeutically effective amount of Compound 1, Compound 2, or Compound 3, or pharmaceutically acceptable salts thereof, hydrates thereof, solvates thereof, or crystalline forms thereof, wherein the patient is resistant or refractory to treatment with a nucleoside agent.

In an embodiment for treating an HBV infection, Compound 1 is administered in an amount from 600 mg per day to 3000 mg per day. In a further embodiment, Compound 1 is administered in an amount of about 2000 mg per day. In an embodiment of this embodiment, Compound 1 is administered in an amount of about 1000 mg twice per day.

In an embodiment for treating an HBV infection, Compound 2 or Compound 3 is administered in an amount from 5 mg per day to 600 mg per day. In another embodiment, Compound 2 or Compound 3 is administered in an amount from 10 mg per day to 50 mg per day. In a particular embodiment, Compound 2 or Compound 3 is administered in an amount of about 25 mg per day. In a further embodiment, Compound 2 or Compound 3 is administered in an amount of about 10 mg once per day to 200 mg once per day.

In another embodiment of these methods, the administration of the compound of Formula I, Formula IA, Formula IB, Formula IIA, Formula IIIA or Formula IIIB, Compound 1, Compound 2, or Compound 3 and the reverse transcriptase inhibitor occurs over a period of time shorter than 48 weeks.

In another embodiment, the patient is a chronically HBV-infected patient.

In an aspect, provided herein is a method of inhibiting replication of a nucleoside resistant HBV variant comprising contacting said variant with an effective amount of a compound of Formula I, Formula IA, Formula IB, Formula IIA, Formula IIIA or Formula IIIB, Compound 1, Compound 2, or Compound 3, or pharmaceutically acceptable salts thereof, hydrates thereof, solvates thereof, or crystalline forms thereof.

In another aspect, provided herein is a method of treating an HBV infection in a patient in need thereof comprising administering to the patient a therapeutically effective amount of a compound of Formula I, Formula IA, Formula IB, Formula IIA, Formula IIIA or Formula IIIB, Compound 1, Compound 2, or Compound 3, or pharmaceutically acceptable salts thereof, hydrates thereof, solvates thereof, or crystalline forms thereof, and Compound A

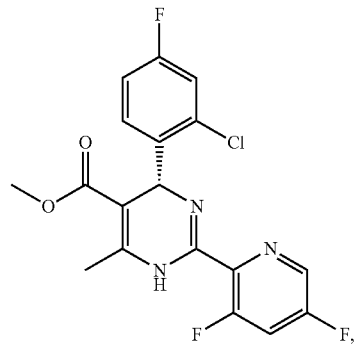

or a pharmaceutically acceptable salt thereof.

BRIEF DESCRIPTION OF THE DRAWINGS

(FIG. 2A) 300 μM LMV, (FIG. 2B) 30 μM ETV, or (FIG. 2C) 30 μM TFV. Primary human hepatocytes from donor HuM4038 were treated for 6 days with test compounds. Data points shown are mean values and error bars are standard deviations from three replicates.

(FIG. 3A) 300 μM LMV, (FIG. 3B) 30 μM ETV, or (FIG. 3C) 30 μM TFV. Primary human hepatocytes from donor HuM4055A were treated for 6 days with test compounds. Data points shown are mean values and error bars are standard deviations from three replicates.

(FIG. 4A) 300 μM LMV, (FIG. 4B) 30 μM ETV, or (FIG. 4C) 30 μM TFV. Primary human hepatocytes from donor HUM4059 were treated for 6 days with test compounds. Data points shown are mean values and error bars are standard deviations from three replicates.

µg/week pegylated interferon (PEG-IFN), and a combination of Compound 1 and PEG-IFN at these doses.

Figure 7A:
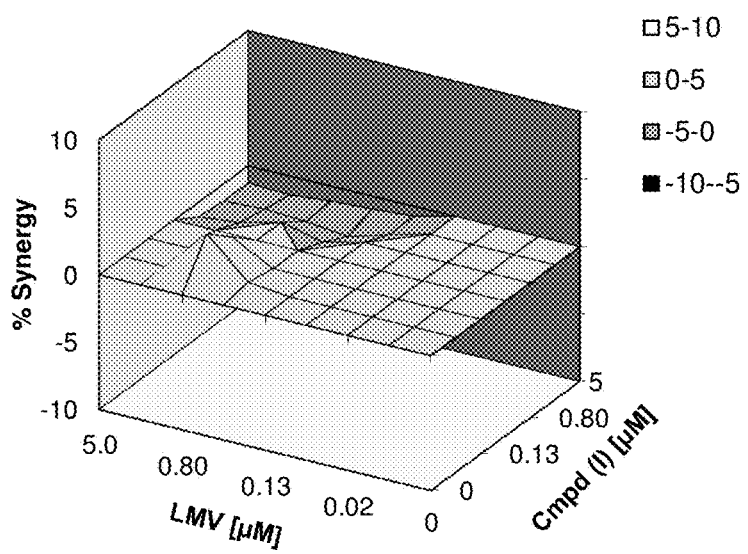
Figure 7B:
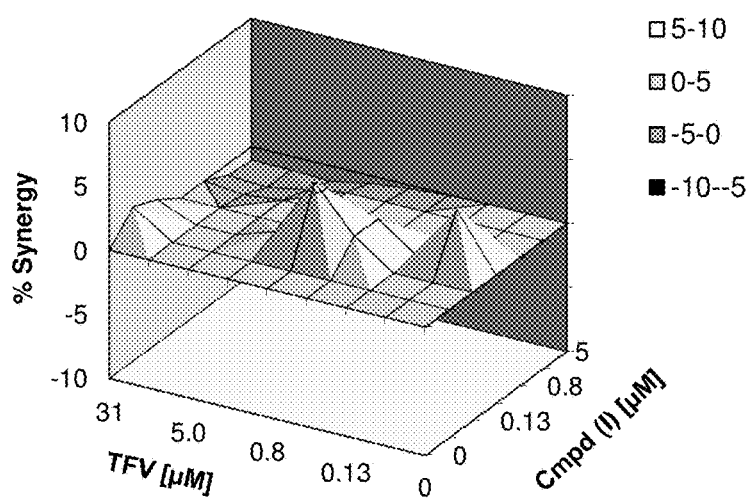
Figure 7C:
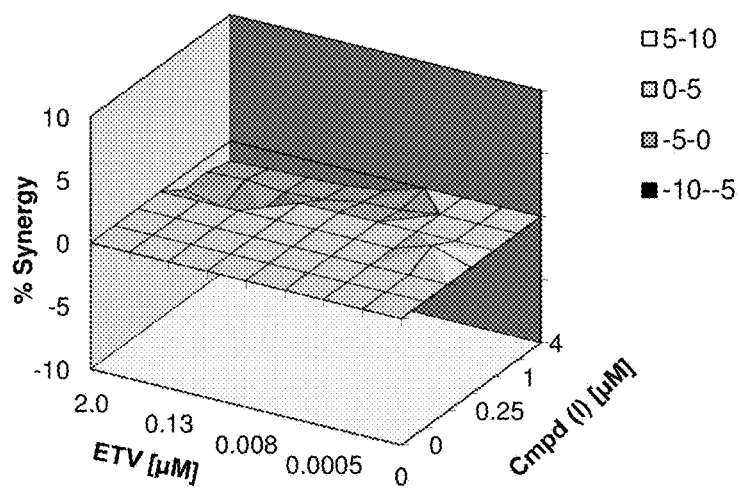

FIG. 7A, FIG. 7B, and FIG. 7C show the effect of a Compound 1 in combination with nucleoside analogs. Compound 1 was used in combination with LMV (FIG. 7A), TFV (FIG. 7B), and ETV (FIG. 7C).

FIG. shows the effect of Compound 1 in combination Bay 41-4109, another core modulator. Synergy plots at 95% confidence from MacSynergy of HepG2.2.15 cells treated with Compound 1 in combination with Bay 41-4109.

Figure 9:
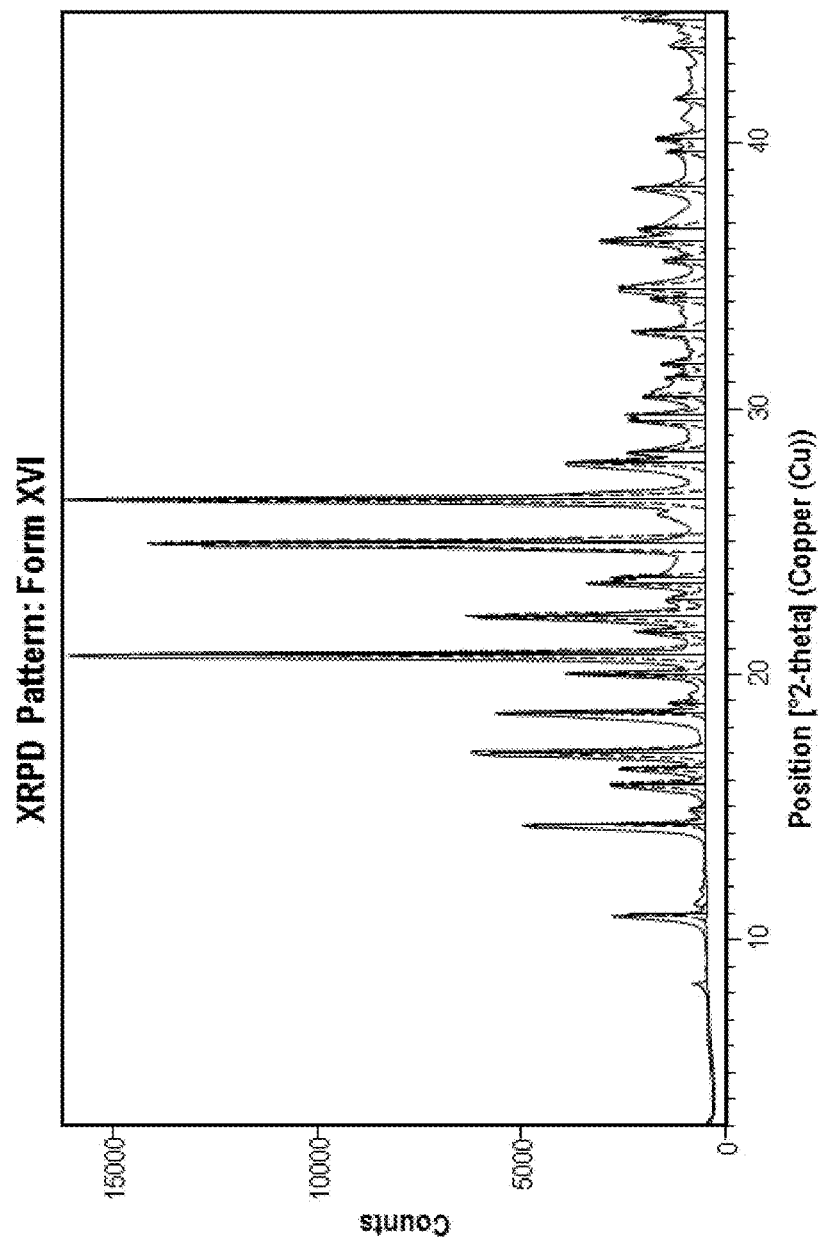

FIG. 9 shows the X-ray powder diffraction pattern of Form XVI of Compound 1.

Figure 10:
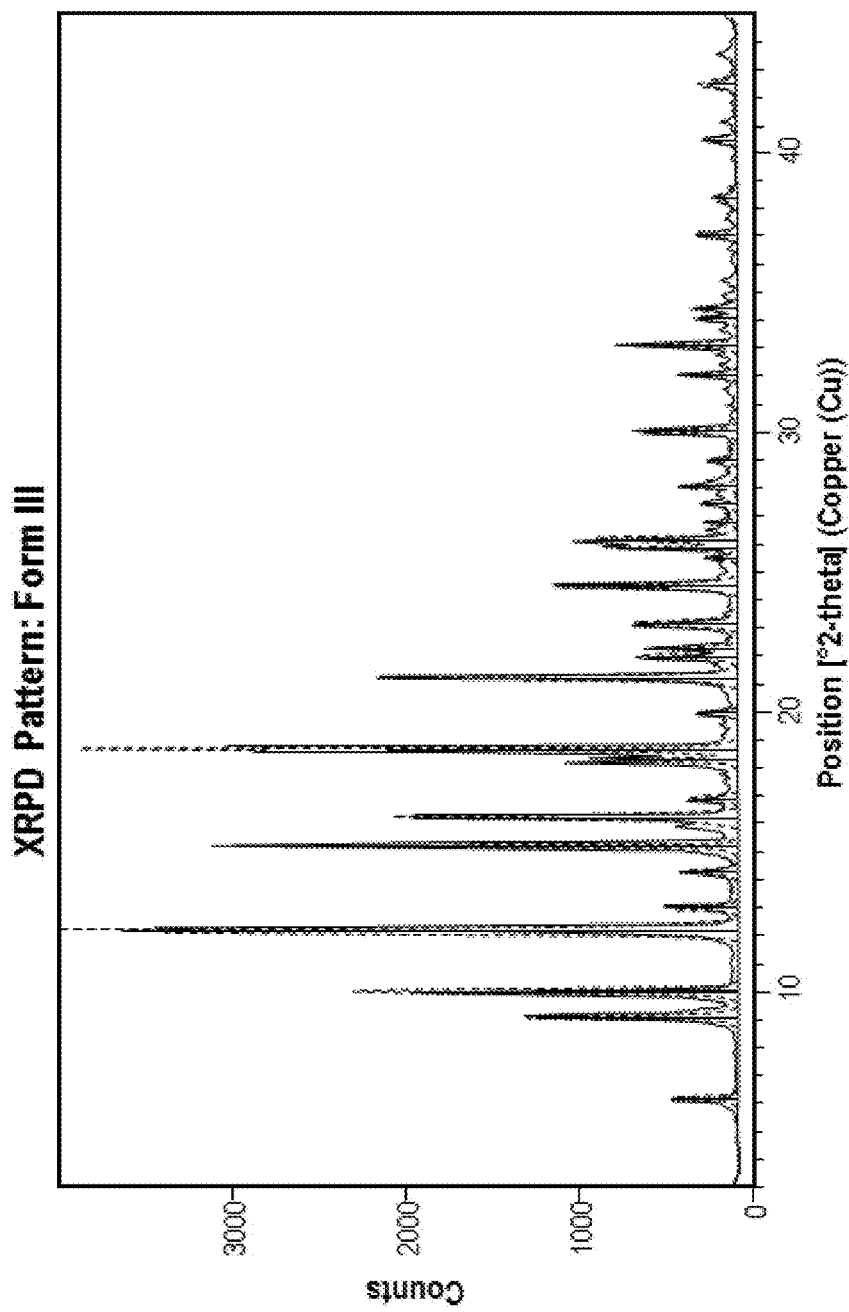

FIG. 10 shows the X-ray powder diffraction pattern of Form III of Compound 1.

Figure 11A:
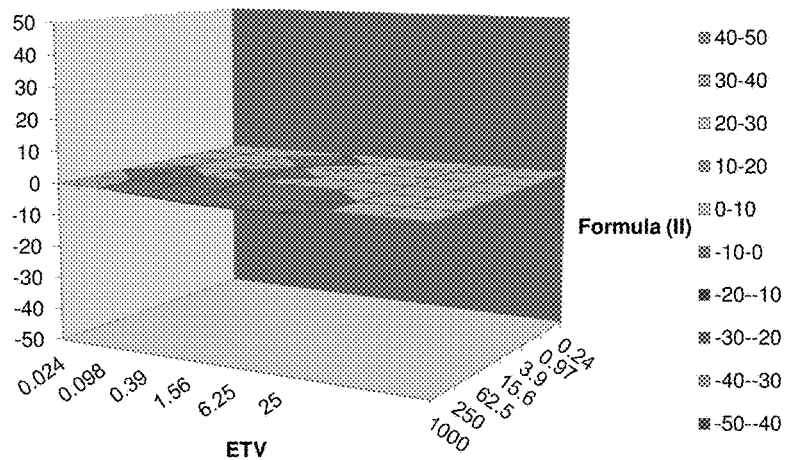
Figure 11B:
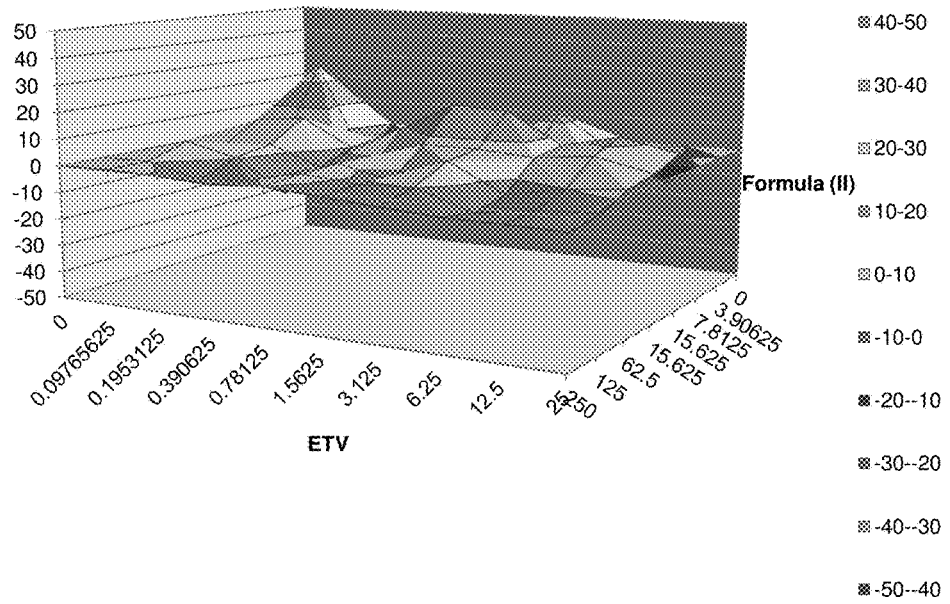
Figure 11C:
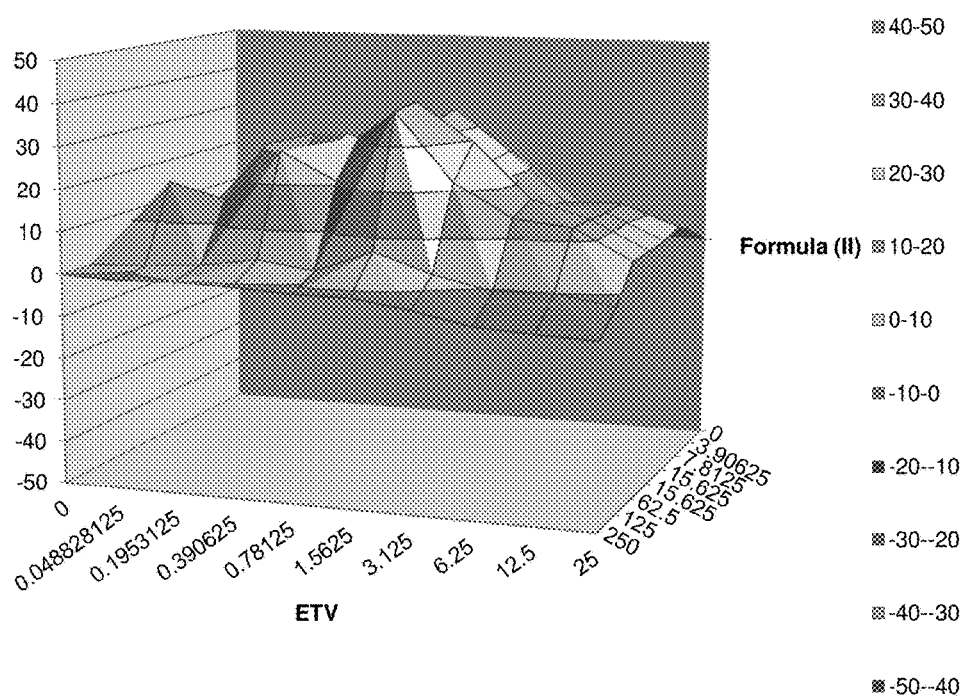
Figure 12A:
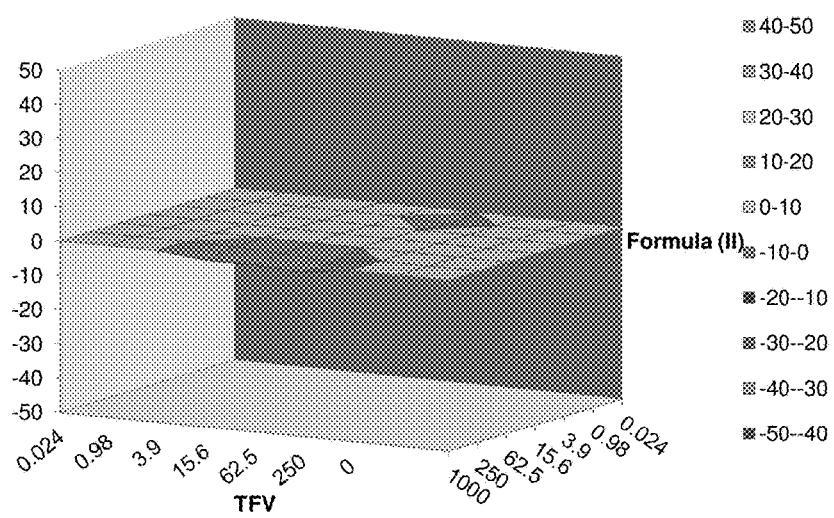
Figure 12B:
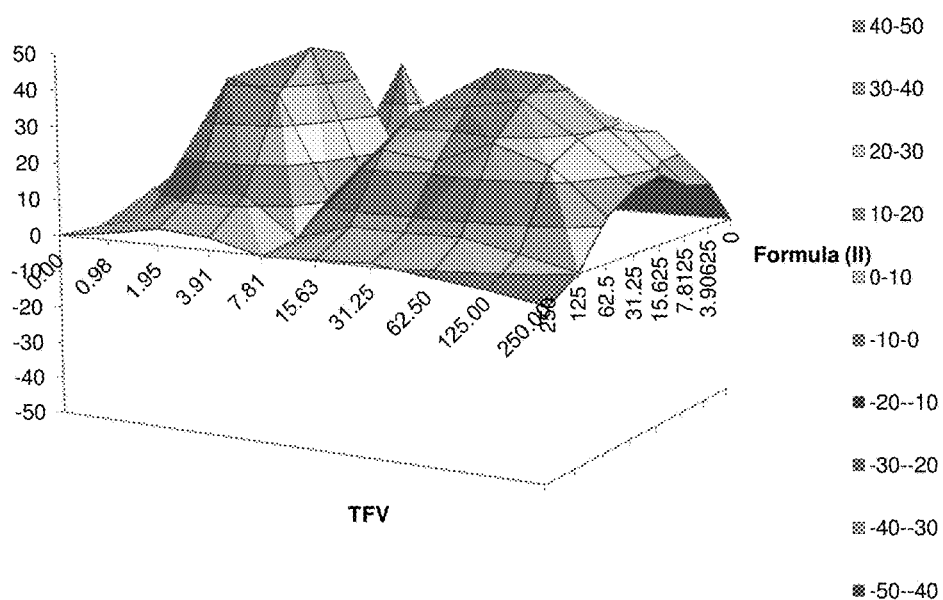
Figure 12C:
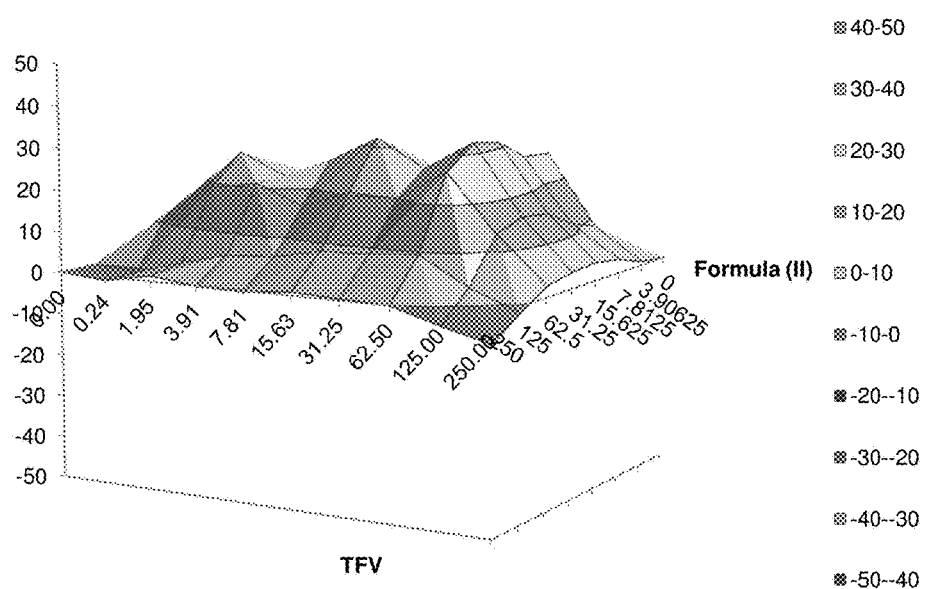

FIG. 11A, FIG. 11B, and FIG. 11C show Synergy Plots of the Combination of Compound 2 with ETV in HepG2.2.15 cells. Synergy plot calculations are based on lower limit values of the 95% CI (Y-axis). Compound concentrations are provided on X- and Z-axis in nM. FIG. 12A corresponds to Experiment 1. FIG. 12B corresponds to Experiment 2. FIG. 12C corresponds to Experiment 3.

FIG. 12A, FIG. 12B, and FIG. 12C show Synergy Plots of the Combination Compound 2 with TFV in HepG2.2.15 cells. Synergy plot calculations are based on lower limit values of the 95% CI (Y-axis). Compound concentrations are provided on X- and Z-axis in nM. FIG. 12A corresponds to Experiment 1. FIG. 12B corresponds to Experiment 2. FIG. 12C corresponds to Experiment 3.

Figure 13:
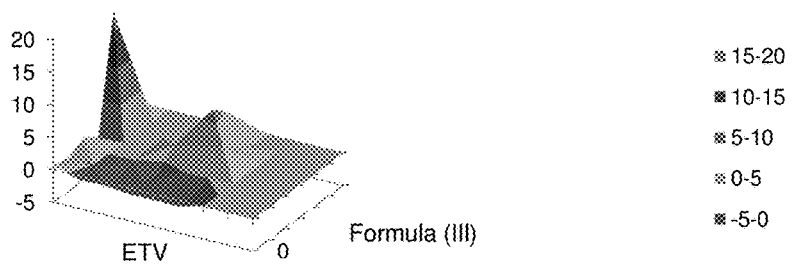

FIG. 13 shows a Synergy Plot of the Combination of Compound 3 with ETV in HepG2.2.15 cells. Synergy plot calculations are based on lower limit values of the 95% CI (Y-axis). Compound concentrations are provided on X- and Z-axis in nM.

Figure 14:
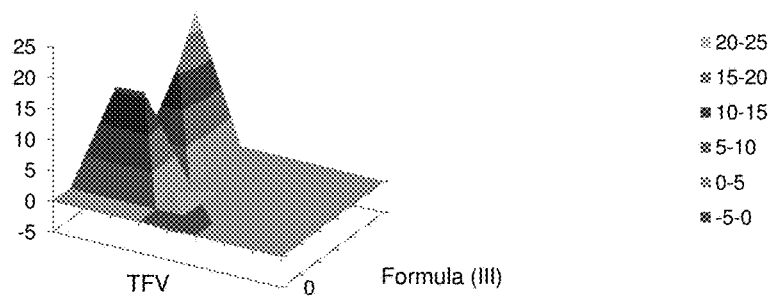

FIG. 14 shows a Synergy Plot of the Combination of Compound 3 with TFV in HepG2.2.15 cells. Synergy plot calculations are based on lower limit values of the 95% CI (Y-axis). Compound concentrations are provided on X- and Z-axis in nM.

FIG. 15A, FIG. 15B, FIG. 15C, and FIG. 15D show the percent inhibition of HBV replication in the presence of Compound 2 and ETV or TFV, at a range of concentrations. Each plot shows the percent inhibition for each compound when the concentration of the other was set to zero.

DETAILED DESCRIPTION OF THE INVENTION

The present disclosure is directed to methods of using a capsid assembly inhibitor for the treatment of hepatitis B virus (HBV) infection. In particular, provided herein is a method of treating an HBV infection in a patient in need thereof, comprising administering to the patient a therapeutically effective amount of a core protein allosteric modulator (CpAM) and a reverse transcriptase inhibitor. In an embodiment, the CpAM is a core protein allosteric modulator that causes aberrant, defective or incomplete assembly of HBV capsids. In another embodiment, the CpAM is a core protein allosteric modulator that causes assembly of capsids that are essentially empty with respect to their viral contents. Also provided herein are methods for treating an HBV infection a patient in need thereof comprising administering a CpAM (e.g., a compound of Formula I, Formula IA, Formula IB, Formula IIA, Formula IIIA or Formula IIIB, Compound 1, Compound 2, or Compound 3) and a reverse transcriptase inhibitor. Further provided herein are combination products and pharmaceutical compositions comprising a CpAM (e.g., a compound of Formula I, Formula IA, Formula IB, Formula IIA, Formula IIIA or Formula IIIB, Compound 1, Compound 2, or Compound 3) and a reverse transcriptase inhibitor. Also provided herein are combination products and pharmaceutical compositions comprising a CpAM having the Formula IB and a reverse transcriptase inhibitor. Also, provided herein are methods for treating an HBV infection in patient resistant or refractory to treatment with a reverse transcriptase inhibitor or a nucleos(t)ide agent comprising administering a compound of Formula I, Formula IA, Formula IB, Formula IIA, Formula IIIA or Formula IIIB, Compound 1, Compound 2, or Compound 3. Also, provided herein are methods for treating an HBV infection in patient resistant or refractory to treatment with a reverse transcriptase inhibitor or a nucleos(t)ide agent comprising administering a compound of Formula IB.

I. Definitions

As used in the specification and in the claims, the term "comprising" may include the embodiments "consisting of" and "consisting essentially of." The terms "comprise(s)," "include(s)," "having," "has," "may,∞ "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated compounds, which allows the presence of only the named compounds, along with any pharmaceutically acceptable carriers, and excludes other compounds.

All ranges disclosed herein are inclusive of the recited endpoint and independently combinable (for example, the range of "from 600 mg to 3000 mg" is inclusive of the endpoints, 600 mg and 3000 mg, and all the intermediate values, such as 2000 mg). The endpoints of the ranges and any values disclosed herein are not limited to the precise range or value; they are sufficiently imprecise to include values approximating these ranges and/or values.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. In at least some instances, the approximating language may correspond to the precision of an instrument for measuring the value. The modifier "about" should also be considered as disclosing the range defined by the absolute values of the two endpoints. For example, the expression "from about 600 to about 3000" also discloses the range "from 600 to 3000." The term "about" may refer to plus or minus 10% of the indicated number. For example, "about 10%" may indicate a range of 9% to 11%, and "about 0" may mean from 0.9 to 1.1. Other meanings of "about" may be apparent from the context, such as rounding off, so, for example "about 1" may also mean from 0.5 to 1.4.

As used herein, the phrase "core protein allosteric modulator (CpAM)" refers to a compound that alters core protein assembly or activity (Zlotnick, Antiviral Research 121 (2015) 82-93). At least two classes of CpAMs have been identified that alter core protein assembly in two distinct ways.

A first class CpAM is shown to misdirect capsid assembly to form aberrant non-capsid polymers. This first class is hereinafter referred to as "a core protein allosteric modulator that causes aberrant, defective or incomplete assembly of HBV capsids." An example of this class is heteroaryldihydropyrimidine (HAP) based compounds. At high concentrations, HAPs lead to misdirected capsid assembly to form aberrant non-capsid polymers. At sub-stoichiometirc concentrataions, when compared to Cp concentration, HAPs increase the rate of capsid assembly. Crystal structures between the HBV capsid and HAP show quaternary structure changes in the capsid, forming connected rigid bodies, with little change to the tertiary structure. An example of a HAP includes, but is not limited to, methyl 4-(2-chloro-4-fluorophenyl)-6-methyl-2-(pyridin-2-yl)-1,4-dihydropyrimidine-5-carboxylate (HAP-1).

One other type of CpAM increases the rate of capsid assembly without affecting capsid morphology, hereinafter referred to as "a core protein allosteric modulator that causes assembly of capsids that are essentially empty with respect to their viral contents."

An example of this class are non-nucleoside-based phenylpropenamide (PPA) based compounds. PPAs increase the rate of capsid assembly without affecting capsid morphology. Cell culture studies reveal that capsids formed in the presence of PPAs are empty with respect to their viral contents, a result of blocking viral RNA packaging. Crystal structures between HBV and PPA show both quaternary and tertiary structure changes as well. Another example of such empty capsid forming CpAMs include, but are not limited to compounds of Formula I, Formula IA, Formula IB, Formula IIA, Formula IIIA or Formula IIIB, Compound 1, Compound 2, and Compound 3 described herein.

Formula IB is also an example of an "a core protein allosteric modulator that causes assembly of essentially empty capsids."

As used herein, the term "reverse transcriptase inhibitor" refers to nucleosides and nulceotides and analogues thereof that inhibit the activity of HBV reverse transcriptase. Examples include, but are not limited to, for example, entecavir, tenofovir, lamivudine, telbivudine, adefovir, clevudine, CMX157, AGX-1009, zidovudine, didanosine, zalcitabine, stavudine, emtricitabine, abacavir, D-D4FC, alovudine, amdoxovir, elvucitabine, delavirdine, efavirenz, nevirapine, capravirine, calanolide A, TMC278, BMS-561390, and DPC-083, or prodrugs thereof and pharmaceutically acceptable salts thereof. Pharmaceutically acceptable prodrugs of tenofovir, for example, include tenofovir disoproxil fumarate and tenofovir alafenamide fumarate.

As used herein, a "reverse transcriptase inhibitor" can be a "purine-based reverse transcriptase inhibitor," which is a reverse transcriptase inhibitor having a purine ring, such as, but not limited to, entecavir and tenofovir.

As used herein, the term "treatment" or "treating," is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has an HBV infection, a symptom of an HBV infection or the potential to develop an HBV infection, with the purpose to cure, heal, alleviate, relieve, alter, remedy, ameliorate, improve or affect the HBV infection, the symptoms of the HBV infection or the potential to develop the HBV infection. Such treatments may be specifically tailored or modified, based on knowledge obtained from the field of pharmacogenomics.

As used herein, the term "patient," "individual," or "subject" refers to a human or a non-human mammal. Non-human mammals include, for example, livestock and pets, such as ovine, bovine, porcine, canine, feline and murine mammals. Preferably, the patient, subject or individual is human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention may be synthesized from the parent compound which contains a basic or acidic moiety by conventional chemical methods. Generally, such salts may be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

The terms "combination," "therapeutic combination," "pharmaceutical combination," or "combination product" as used herein refer to either a fixed combination in one dosage unit form, or non-fixed combination, or a kit of parts for the combined administration where two or more therapeutic agents may be administered independently, at the same time or separately within time intervals, especially where these time intervals allow that the combination partners show a cooperative, e.g., synergistic, effect. The term "combination therapy" refers to the administration of two or more therapeutic agents to treat a therapeutic condition or disorder described in the present disclosure. Such administration encompasses co-administration of these therapeutic agents in a substantially simultaneous manner, such as in a single formulation having a fixed ratio of active ingredients or in separate formulations (e.g., capsules and/or intravenous formulations) for each active ingredient. In addition, such administration also encompasses use of each type of therapeutic agent in a sequential or separate manner, either at approximately the same time or at different times. Regardless of whether the active ingredients are administered as a single formulation or in separate formulations, the drugs are administered to the same patient as part of the same course of therapy. In any case, the treatment regimen will provide beneficial effects in treating the conditions or disorders described herein.

The term "synergistic effect" refers to the action of two agents, such as, for example, a capsid assembly inhibitor and a reverse transcriptase inhibitor, producing an effect, for example, slowing the symptomatic progression of HBV-infection or symptoms thereof, which is greater than the simple addition of the effects of each drug administered alone. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984) and Chou, Pharmacol. Rev. 58: 621-681 (2006). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively. In some embodiments, the combination of compounds exhibits a synergistic effect (i.e., greater than additive effect) in the treatment of HBV infection. In further embodiments, the combination of compounds exhibits a synergistic effect (i.e., greater than additive effect) in the treatment of HBV-infection.

Synergy volumes of <−100, −100 to −50, −50 to −25, −25 to 25, 25 to 50, 50 to 100, and >100 indicate strong antagonism, moderate antagonism, slight antagonism, insignificant synergism/antagonism (additivity), slight synergism, moderate synergism, and strong synergism respectively.

As used herein, the term "resistant" or "refractive" to a therapeutic agent when referring to an HBV patient means that the HBV patient has innate, or achieved resistance to, the effects of the therapeutic agent as a result of contact with the therapeutic agent. Stated alternatively, the HBV patient is resistant to the ordinary standard of care associated with the particular therapeutic agent.

As used herein, "treatment naïve" refers to the patient not having previously received treatment with a drug—investigational or approved—for HBV infection, in particular, a nucleos(t)ide drug.

Alternatively, patients treated according to the methods of the disclosure may be "treatment experienced." As used herein, "treatment experienced" refers to a patient who has had at least one previous course of an HBV antiviral therapy, in particular a nucleos(t)ide. In some embodiments, the last dose in this previous course occurred at least three months prior to implementing a method according to the present disclosure.

HBV infections that may be treated according to the disclosed methods include HBV genotype A, B, C, and/or D infections. However, in an embodiment, the methods disclosed may treat any HBV genotype ("pan-genotypic treatment"). HBV genotyping may be performed using methods known in the art, for example, INNO-LIPA® HBV Genotyping, Innogenetics N.V., Ghent, Belgium).

As used herein, the term "alkyl," by itself or as part of another substituent means, unless otherwise stated, a straight or branched chain hydrocarbon having the number of carbon atoms designated (i.e., $C_1$-$C_6$-alkyl means an alkyl having one to six carbon atoms) and includes straight and branched chains. Examples include methyl, ethyl, propyl, isopropyl, butyl, isobutyl, tert-butyl, pentyl, neopentyl, and hexyl. Other examples of $C_1$-$C_6$-alkyl include ethyl, methyl, isopropyl, isobutyl, n-pentyl, and n-hexyl.

As used herein, the term "alkenyl" denotes a monovalent group derived from a hydrocarbon moiety containing at least two carbon atoms and at least one carbon-carbon double bond. The double bond may or may not be the point of attachment to another group. Alkenyl groups (e.g., $C_2$-$C_8$-alkenyl) include, but are not limited to, for example, ethenyl, propenyl, prop-1-en-2-yl, butenyl, 1-methyl-2-buten-1-yl, heptenyl, octenyl and the like.

As used herein, "alkynyl," means a straight or branched hydrocarbon radical containing up to 6 carbon atoms and having at least one carbon-carbon triple bond. Examples of alkynyl groups include, without limitation, ethynyl, 1-propynyl, 1-butynyl, and the like.

As used herein, the term "alkoxy," refers to the group —O-alkyl, wherein alkyl is as defined herein. Alkoxy includes, by way of example, methoxy, ethoxy, n-propoxy, isopropoxy, n-butoxy, sec-butoxy, t-butoxy and the like.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" means a non-aromatic carbocyclic system that is partially or fully saturated having 1, 2 or 3 rings wherein such rings may be fused. The term "fused" means that a second ring is present (i.e., attached or formed) by having two adjacent atoms in common (i.e., shared) with the first ring. Cycloalkyl also includes bicyclic structures that may be bridged or spirocyclic in nature with each individual ring within the bicycle varying from 3-8 atoms. The term "cycloalkyl" includes, but is not limited to, cyclopropyl, cyclobutyl, cyclopentyl, cyclohexyl, bicyclo[3.1.0]hexyl, spiro[3.3]heptanyl, and bicyclo[1.1.1]pentyl.

As used herein, the term "heterocycloalkyl" means a non-aromatic carbocyclic system containing 1, 2, 3 or 4 heteroatoms selected independently from N, O, and S and having 1, 2 or 3 rings wherein such rings may be fused, wherein fused is defined above. Heterocycloalkyl also includes bicyclic structures that may be bridged or spirocyclic in nature with each individual ring within the bicycle varying from 3-8 atoms, and containing 0, 1, or 2N, O, or S atoms. The term "heterocycloalkyl" includes cyclic esters (i.e., lactones) and cyclic amides (i.e., lactams) and also specifically includes, but is not limited to, epoxidyl, oxetanyl, tetrahydrofuranyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-azabicyclo[2.1.1]hexanyl, 5-azabicyclo[2.1.1]hexanyl, 6-azabicyclo[3.1.1]heptanyl, 2-azabicyclo[2.2.1]heptanyl, 3-azabicyclo[3.1.1]heptanyl, 2-azabicyclo[3.1.1]heptanyl, 3-azabicyclo[3.1.0]hexanyl, 2-azabicyclo[3.1.0]hexanyl, 3-azabicyclo[3.2.1]octanyl, 8-azabicyclo[3.2.1]octanyl, 3-oxa-7-azabicyclo[3.3.1] nonanyl, 3-oxa-9-azabicyclo[3.3.1]nonanyl, 2-oxa-5-azabicyclo[2.2.1]heptanyl, 6-oxa-3-azabicyclo[3.1.1]heptanyl, 2-azaspiro[3.3]heptanyl, 2-oxa-6-azaspiro[3.3]heptanyl, 2-oxaspiro[3.3]heptanyl, 2-oxaspiro[3.5]nonanyl, 3-oxaspiro[5.3]nonanyl, and 8-oxabicyclo [3.2.1]octanyl.

As used herein, the term "aromatic" refers to a carbocycle or heterocycle with one or more polyunsaturated rings and having aromatic character, i.e., having (4n+2) delocalized 7E (pi) electrons, where n is an integer.

As used herein, the term "aryl" means an aromatic carbocyclic system containing 1, 2 or 3 rings, wherein such rings may be fused, wherein fused is defined above. If the rings are fused, one of the rings must be fully unsaturated and the fused ring(s) may be fully saturated, partially unsaturated or fully unsaturated. The term "aryl" includes, but is not limited to, phenyl, naphthyl, indanyl, and 1,2,3,4-tetrahydronaphthalenyl.

As used herein, the term "heteroaryl" means an aromatic carbocyclic system containing 1, 2, 3, or 4 heteroatoms selected independently from N, O, and S and having 1, 2, or 3 rings wherein such rings may be fused, wherein fused is defined above. The term "heteroaryl" includes, but is not limited to, furanyl, thiophenyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl.

It is to be understood that if an aryl, heteroaryl, cycloalkyl, or heterocycloalkyl moiety is bonded or otherwise attached to a designated moiety through differing ring atoms (i.e., shown or described without denotation of a specific point of attachment), then all possible points are intended, whether through a carbon atom or, for example, a trivalent nitrogen atom. For example, the term "pyridinyl" means 2-, 3- or 4-pyridinyl, the term "thiophenyl" means 2- or 3-thiophenyl, and so forth.

As used herein, the term "substituted" means that an atom or group of atoms has replaced hydrogen as the substituent attached to another group.

I. Compounds

Provided herein is a method of treating an HBV infection in a patient in need thereof, comprising administering to the patient a therapeutically effective amount of a core protein allosteric modulator (CpAM) and a reverse transcriptase inhibitor. In an embodiment, the CpAM is a core protein allosteric modulator that causes aberrant, defective or incomplete assembly of HBV capsids. In another embodiment, the CpAM is a core protein allosteric modulator that causes assembly of capsids that are essentially empty with respect to their viral contents. The methods, combination product, and compositions provided herein comprise a compound of Formula I

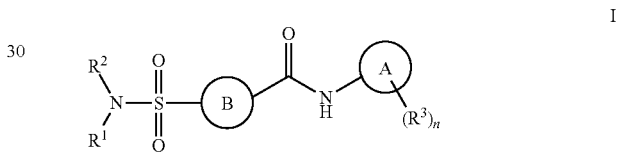

or a pharmaceutically acceptable salt thereof, a hydrate thereof, solvate thereof, or a crystalline form thereof and a reverse transcriptase inhibitor, or a pharmaceutically acceptable salt, or a prodrug thereof.

wherein

A is phenyl or pyridinyl;

B is a monocyclic 5-to-6-membered aromatic or heteroaromatic ring, wherein the aromatic ring or heteroaromatic ring is optionally substituted with one or more substitutents each independently selected from halogen or $C_1$-$C_6$ alkyl;

$R^1$ is H or $C_1$-$C_6$ alkyl;

$R^2$ is $C_1$-$C_6$ alkyl, wherein said $C_1$-$C_6$ alkyl is optionally substituted with one or more substituents each independently selected from the group consisting of: halogen, $C_1$-$C_6$ alkoxy, oxo, $C_1$-$C_6$ alkyl, OH, CN, $CFH_2$, $CF_2H$ and $CF_3$, or $R^1$ and $R^2$ are taken together to form a $C_2$-$C_7$ heterocycloalkyl ring, wherein said $C_2$-$C_7$ heterocycloalkyl ring is optionally substituted with one or more substituents each independently selected from the group consisting of: halogen, $C_1$-$C_6$ alkoxy, oxo, $C_1$-$C_6$ alkyl, OH, CN, $CFH_2$, $CF_2H$ and $CF_3$;

each $R^3$ is independently selected from the group consisting of: halogen, $C_1$-$C_6$ alkyl, $C_1$-$C_6$ alkoxy, cyano, $C_1$-$C_6$ alkenyl, $C_1$-$C_6$ alkynyl, and OH; and n is 0, 1, 2, or 3.

In an embodiment of Formula I, B is a 5-membered heteroaromatic ring that is optionally and independently substituted one or more times with halogen or $C_1$-$C_6$ alkyl.

In an embodiment, the compound of Formula I is a compound of Formula IA

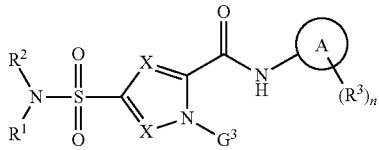

IA or a pharmaceutically acceptable salt thereof, a hydrate thereof, solvate thereof, or a crystalline form thereof,
wherein
A is phenyl or pyridinyl;
$R^1$ is H or $C_1$-$C_6$ alkyl;
$R^2$ is $C_1$-$C_6$ alkyl, which is optionally and independently substituted one or more times with halogen, $C_1$-$C_6$ alkoxy, oxo, $C_1$-$C_6$ alkyl, OH, CN, $CFH_2$, $CF_2H$ or $CF_3$;
$R^3$ is independently for each occurrence halogen, $C_1$-$C_6$ alkyl, $C_1$-$C_6$ alkoxy, cyano, $C_1$-$C_6$ alkenyl, $C_1$-$C_6$ alkynyl, or OH;
X is $CR^4$;
$G^3$ is H or $C_1$-$C_6$ alkyl;
$R^4$ is independently for each occurrence H, halogen, $C_1$-$C_3$ alkyl, or cyano; and
n is 0, 1, 2, or 3.

In an embodiment, the compound of Formula I is a compound of Formula IB

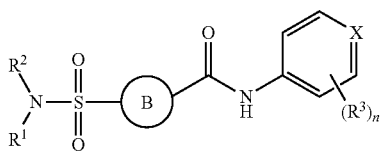

IB or a pharmaceutically acceptable salt thereof, a hydrate thereof, solvate thereof, or a crystalline form thereof,
wherein
X is CR or N;
B is $C_5$-$C_6$ aryl, $C_5$-$C_6$ cycloalkyl, 5-6-membered heteroaryl, or 5-6-membered heterocyclyl, all of which may be optionally substituted with $C_1$-$C_4$ alkyl or halo;
$R^1$ is H or $C_1$-$C_6$ alkyl;
$R^2$ is $C_1$-$C_6$ alkyl, which is optionally and independently substituted one or more times with halogen, $C_1$-$C_6$ alkoxy, oxo, $C_1$-$C_6$ alkyl, OH, CN, $CFH_2$, $CF_2H$ or $CF_3$;
$R^3$ is independently for each occurrence halogen, $C_1$-$C_6$ alkyl, $C_1$-$C_6$ alkoxy, cyano, $C_1$-$C_6$ alkenyl, $C_1$-$C_6$ alkynyl, or OH;
R is $C_1$-$C_4$ alkyl, or halo; and
n is 0, 1, 2, or 3.

In an embodiment, the compound of Formula I is a compound of Formula II

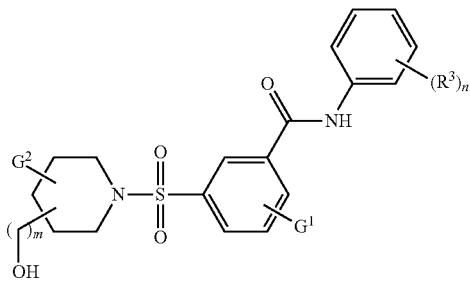

II or a pharmaceutically acceptable salt thereof, a hydrate thereof, solvate thereof, or a crystalline form thereof,
wherein
$R^3$ is halo;
$G^1$ is H, $C_1$-$C_4$ alkyl, or halo;
$G^2$ is selected from the group consisting of: H, halo, $C_1$-$C_4$ alkyl, and OH;
n is 0, 1, 2, or 3; and
m is 0, 1, or 2.

In another embodiment, the compound of Formula I is a compound of Formula IIIA

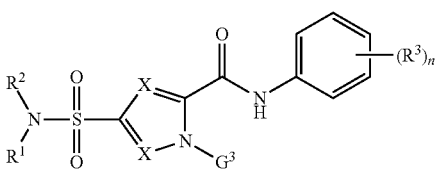

IIIA or a pharmaceutically acceptable salt thereof, a hydrate thereof, solvate thereof, or a crystalline form thereof,
wherein
$R^1$ is H or $C_1$-$C_6$ alkyl;
$R^2$ is $C_1$-$C_6$ alkyl, which is optionally and independently substituted one or more times with halogen, $C_1$-$C_6$ alkoxy, oxo, $C_1$-$C_6$ alkyl, OH, CN, $CFH_2$, $CF_2H$ or $CF_3$;
$R^3$ is independently for each occurrence halogen, $C_1$-$C_6$ alkyl, $C_1$-$C_6$ alkoxy, cyano, $C_1$-$C_6$ alkenyl, $C_1$-$C_6$ alkynyl, or OH;
$R^4$ is H, halogen, $C_1$-$C_3$ alkyl, or cyano; and In yet another embodiment, the compound of Formula I is a compound of Formula IIIB

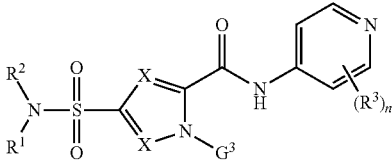

IIIB or a pharmaceutically acceptable salt thereof, a hydrate thereof, solvate thereof, or a crystalline form thereof,
wherein
$R^1$ is H or $C_1$-$C_6$ alkyl;
$R^2$ is $C_1$-$C_6$ alkyl, wherein said $C_1$-$C_6$ alkyl is optionally substituted with one or more substitutents each independently selected from the group consisting of: halogen, $C_1$-$C_6$ alkoxy, oxo, $C_1$-$C_6$ alkyl, OH, CN, $CFH_2$, $CF_2H$ and $CF_3$;

each $R^3$ is independently selected from the group consisting of: halogen, $C_1$-$C_6$ alkyl, $C_1$-$C_6$ alkoxy, cyano, $C_1$-$C_6$ alkenyl, $C_1$-$C_6$ alkynyl, and OH;

$G^3$ is H or $C_1$-$C_6$ alkyl;

X is $CR^4$;

$R^4$ is selected from the group consisting of: H, halogen, $C_1$-$C_3$ alkyl, and cyano; and n is 0, 1, 2, or 3.

The methods, combination product, and compositions provided herein can comprise Compound 1:

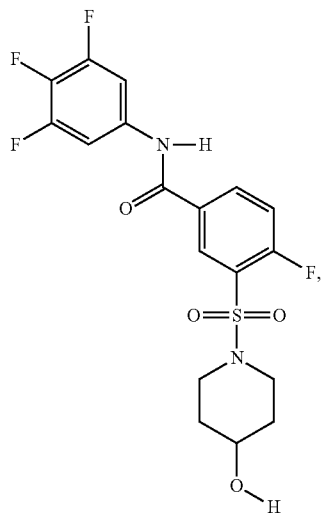

Compound 1

Compound 1 is also referred to herein as "Compound I" or "Cmpd (I)." Compound 1, including the synthesis thereof, is disclosed in PCT Publication No. WO/2013/096744, which is hereby incorporated by reference in its entirety.

Further, Compound 1 can exist in crystalline form, preferably one that is stable upon exposure to higher temperatures and humidity. Various crystal forms of Compound 1 are described in WO/2017/059059, which is hereby incorporated by reference in its entirety.

For example Form (XVI) of Compound 1 has an X-ray powder diffraction pattern as shown in FIG. 9. The corresponding °2-theta values are found in Table 12.

TABLE 12

X-Ray powder diffraction pattern of Form XVI of Compound 1

| No. | Pos. [° 2-theta] | Peak Height [cts] |
| --- | --- | --- |
| 1 | 8.3325 | 177.19 |
| 2 | 10.9344 | 1935.52 |
| 3 | 14.3722 | 3710.48 |
| 4 | 14.9241 | 373.24 |
| 5 | 15.8427 | 2224.43 |
| 6 | 16.4561 | 2064.13 |
| 7 | 17.0677 | 5116.86 |
| 8 | 18.5296 | 4972.27 |
| 9 | 18.9049 | 872.76 |
| 10 | 20.0163 | 3381.98 |
| 11 | 20.7658 | 13446.21 |
| 12 | 21.5994 | 1648.19 |
| 13 | 22.1592 | 5552.43 |
| 14 | 22.8341 | 878.36 |
| 15 | 23.4421 | 2910.94 |
| 16 | 23.6338 | 2169.37 |
| 17 | 24.9292 | 12671.51 |
| 18 | 26.5972 | 15673.37 |

TABLE 12-continued

X-Ray powder diffraction pattern of Form XVI of Compound 1

| No. | Pos. [° 2-theta] | Peak Height [cts] |
| --- | --- | --- |
| 19 | 27.9963 | 3230.31 |
| 20 | 28.3825 | 1934.34 |
| 21 | 29.5627 | 1788.4 |
| 22 | 29.766 | 1697.44 |
| 23 | 30.4527 | 1526.62 |
| 24 | 31.1958 | 954.79 |
| 25 | 31.7034 | 1030.38 |
| 26 | 32.9259 | 1755.93 |
| 27 | 34.1563 | 1312 |
| 28 | 34.5404 | 2059.7 |
| 29 | 35.6022 | 1008.97 |
| 30 | 36.3734 | 2480.94 |
| 31 | 36.753 | 1575.29 |
| 32 | 38.3689 | 1684.63 |
| 33 | 39.7099 | 915.35 |
| 34 | 40.1675 | 1190.9 |
| 35 | 41.707 | 685.21 |
| 36 | 43.6419 | 800.32 |
| 37 | 44.6892 | 1534.39 |

Thus, in one embodiment, Compound 1 is in a crystalline form characterized by an X-ray powder diffraction pattern having peaks expressed in degrees-2-theta at angles (±0.2°) of 17.1, 20.8, 22.2, 24.9, and 26.6 (Form XVI).

In a further embodiment, the crystalline form is characterized by an X-ray powder diffraction pattern having peaks expressed in degrees-2-theta at angles (±0.2°) of 14.4, 17.1, 18.5, 20.0, 20.8, 22.2, 23.4, 24.9, 26.6, 28.0, and 36.4 (Form XVI).

In yet a further embodiment, the crystalline form is characterized by an X-ray powder diffraction pattern having peaks expressed in degrees-2-theta at angles (±0.2°) of 8.3, 10.9, 14.4, 14.9, 15.8, 16.5, 17.1, 18.5, 18.9, 20.0, 20.8, 21.6, 22.2, 22.8, 23.4, 23.6, 24.9, 26.6, 28.0, 28.4, 29.6, 29.8, 30.5, 31.2, 31.7, 32.9, 34.2, 34.5, 35.6, 36.4, 36.8, 38.4, 39.7, 40.2, 41.7, 43.6, and 44.7 (Form XVI).

In another embodiment, the crystalline form is characterized by an X-ray powder diffraction pattern having peaks expressed in degrees-2-theta at angles (±0.2°) of of 8.33, 10.93, 14.37, 14.92, 15.84, 16.46, 17.07, 18.53, 18.90, 20.02, 20.77, 21.60, 22.16, 22.83, 23.44, 23.63, 24.93, 26.60, 28.00, 28.38, 29.56, 29.77, 30.45, 31.20, 31.70, 32.93, 34.16, 34.54, 35.60, 36.37, 36.75, 38.37, 39.71, 40.17, 41.71, 43.64, and 44.69 (Form XVI).

In an embodiment, the crystalline form is characterized by an X-ray powder diffraction pattern that is substantially the same as that of FIG. 9.

The X-ray powder diffraction pattern of Form III of Compound 1 is shown in FIG. 10. The corresponding °2-theta values are found in Table 11.

TABLE 11

X-Ray powder diffraction pattern of Compound 1 (Form III, Solvate of Acetone)

| No. | Pos. [° 2-theta] | Height [cts] |
| --- | --- | --- |
| 1 | 6.1533 | 339.26 |
| 2 | 9.0816 | 1104.7 |
| 3 | 9.9483 | 1907.02 |
| 4 | 10.0321 | 1552.49 |
| 5 | 12.1685 | 3556.97 |
| 6 | 12.9616 | 383.06 |
| 7 | 14.2397 | 315.01 |
| 8 | 15.1483 | 2480.83 |
| 9 | 16.2048 | 1828.9 |

TABLE 11-continued

X-Ray powder diffraction pattern of Compound 1 (Form III, Solvate of Acetone)

| No. | Pos. [° 2-theta] | Height [cts] |
|---|---|---|
| 10 | 16.8775 | 256.66 |
| 11 | 18.269 | 953.62 |
| 12 | 18.6378 | 3776.85 |
| 13 | 19.9348 | 205.82 |
| 14 | 21.1993 | 1960.44 |
| 15 | 21.9332 | 550.39 |
| 16 | 22.2455 | 479.41 |
| 17 | 23.1308 | 548.36 |
| 18 | 24.4803 | 948.12 |
| 19 | 25.4636 | 170.21 |
| 20 | 25.8397 | 586.56 |
| 21 | 26.139 | 787.4 |
| 22 | 26.7489 | 173.31 |
| 23 | 27.404 | 149.44 |
| 24 | 28.053 | 307.13 |
| 25 | 28.9464 | 155.2 |
| 26 | 30.0145 | 564.17 |
| 27 | 31.9986 | 284.25 |
| 28 | 33.0882 | 659.21 |
| 29 | 34.0244 | 203.24 |
| 30 | 34.3991 | 227.63 |
| 31 | 37.0076 | 210.03 |
| 32 | 38.3419 | 102.07 |
| 33 | 40.4682 | 165.35 |
| 34 | 42.4278 | 144.39 |

In another aspect, the methods, combination product, and compositions provided herein comprise Compound 2:

Compound 2

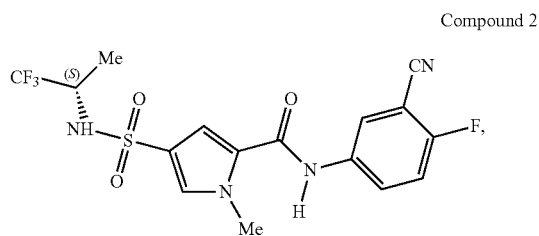

or a pharmaceutically acceptable salt thereof, a hydrate thereof, a solvate thereof, or a crystalline form thereof. Compound 2 is also referred to herein as "Compound II" or "Cmpd II." Compound 2, including the synthesis thereof, is disclosed in PCT Publication No. WO 2014/184350 which is hereby incorporated by reference in its entirety.

In yet another aspect, the methods, combination product, and compositions provided herein comprise Compound 3:

Compound 3

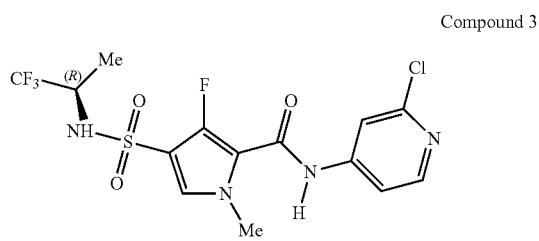

or a pharmaceutically acceptable salt thereof, a hydrate thereof, a solvate thereof, or a crystalline form thereof. Compound 3 is also referred to herein as "Compound III" or "Cmpd (III)." Compound 3, including the synthesis thereof, is disclosed in PCT Publication No WO2015/118057, which is hereby incorporated by reference in its entirety.

II. Methods

In an aspect, provided herein is a method of treating an HBV infection in a patient in need thereof, comprising administering to the patient a therapeutically effective amount of a core protein allosteric modulator (CpAM) and a therapeutically effective amount of a reverse transcriptase inhibitor. In an embodiment of the method, the CpAM is a core protein allosteric modulator that causes aberrant, defective or incomplete assembly of HBV capsids. In another embodiment of the method, the CpAM is a core protein allosteric modulator that causes assembly of capsids that are essentially empty with respect to their viral contents. In an aspect, provided herein is a method of treating an HBV infection in a patient in need thereof comprising administering to the patient a therapeutically effective amount of a compound of Formula I, or a pharmaceutically acceptable salt thereof, a hydrate thereof, a solvate thereof, or a crystalline form thereof, and a reverse transcriptase inhibitor, or a pharmaceutically acceptable salt or a prodrug thereof.

In another aspect, provided herein is a method of treating an HBV infection in a patient in need thereof comprising administering to the patient a therapeutically effective amount of a compound of Formula IA, or a pharmaceutically acceptable salt thereof, a hydrate thereof, a solvate thereof, or a crystalline form thereof, and a reverse transcriptase inhibitor, or a pharmaceutically acceptable salt or a prodrug thereof.

In another aspect, provided herein is a method of treating an HBV infection in a patient in need thereof comprising administering to the patient a therapeutically effective amount of a compound of Formula IB, or a pharmaceutically acceptable salt thereof, a hydrate thereof, a solvate thereof, or a crystalline form thereof, and a reverse transcriptase inhibitor, or a pharmaceutically acceptable salt or a prodrug thereof.

In another aspect, provided herein is a method of treating an HBV infection in a patient in need thereof comprising administering to the patient a therapeutically effective amount of a compound of Formula II, or a pharmaceutically acceptable salt thereof, a hydrate thereof, a solvate thereof, or a crystalline form thereof, and a reverse transcriptase inhibitor, or a pharmaceutically acceptable salt or a prodrug thereof.

In still another aspect, provided herein is a method of treating an HBV infection in a patient in need thereof comprising administering to the patient a therapeutically effective amount of a compound of Formula IIIA, or a pharmaceutically acceptable salt thereof, a hydrate thereof, a solvate thereof, or a crystalline form thereof, and a reverse transcriptase inhibitor, or a pharmaceutically acceptable salt or a prodrug thereof.

In still another aspect, provided herein is a method of treating an HBV infection in a patient in need thereof comprising administering to the patient a therapeutically effective amount of: a compound of Formula IIIB, or a pharmaceutically acceptable salt thereof, a hydrate thereof, a solvate thereof, or a crystalline form thereof, and a reverse transcriptase inhibitor, or a pharmaceutically acceptable salt or a prodrug thereof.

In still another aspect, provided herein is a method of treating an HBV infection in a patient in need thereof comprising administering to the patient a therapeutically effective amount of Compound 1:

Compound 1

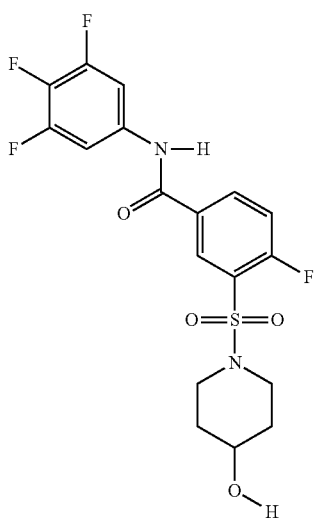

or a pharmaceutically acceptable salt thereof, a hydrate thereof, a solvate thereof, or a crystalline form thereof, and a reverse transcriptase inhibitor, or a pharmaceutically acceptable salt or a prodrug thereof.

In another aspect, provided herein is a method of treating an HBV infection in a patient in need thereof comprising administering to the patient a therapeutically effective amount of Compound 2:

Compound 2

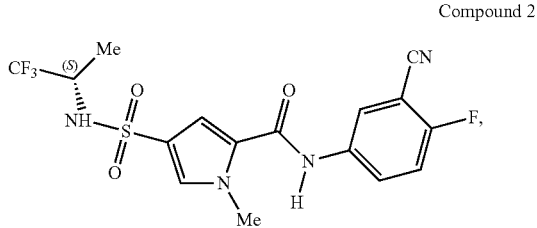

or a pharmaceutically acceptable salt thereof, a hydrate thereof, a solvate thereof, or a crystalline form thereof, and a reverse transcriptase inhibitor, or a pharmaceutically acceptable salt or a prodrug thereof.

In yet another aspect, provided herein is a method of treating an HBV infection in a patient in need thereof comprising administering to the patient a therapeutically effective amount of Compound 3:

Compound 3

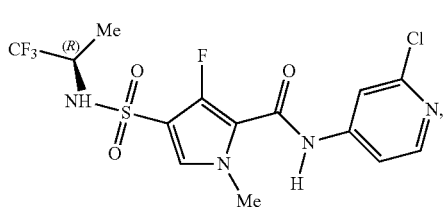

or a pharmaceutically acceptable salt thereof, a hydrate thereof, a solvate thereof, or a crystalline form thereof, and a reverse transcriptase inhibitor, or a pharmaceutically acceptable salt or a prodrug thereof.

Patients who may be treated using the described methods are in some embodiments human Other warm-blooded animals may also be treated.

In an embodiment of the method, the reverse transcriptase inhibitor is selected from the group consisting of entecavir, tenofovir, and lamivudine, or pharmaceutically acceptable salts or prodrugs thereof. Pharmaceutically acceptable prodrugs of tenofovir include tenofovir disoproxil fumarate and tenofovir alafenamide fumarate.

In another embodiment, the reverse transcriptase inhibitor is a purine-based reverse transcriptase inhibitor.

In an embodiment, the compound of Formula I, Formula IA, Formula IB, Formula II, Formula IIIA or Formula IIIB and the reverse transcriptase inhibitor are in the same formulation. In another embodiment, the compound of Formula I, Formula IA, Formula IB, Formula II, Formula IIIA or Formula IIIB and the reverse transcriptase inhibitor are in separate formulations.

In another embodiment, the compound of Formula IA and the reverse transcriptase inhibitor are in the same formulation. In another embodiment, the compound of Formula IA and the reverse transcriptase inhibitor are in separate formulations.

In another embodiment, the compound of Formula IB and the reverse transcriptase inhibitor are in the same formulation. In another embodiment, the compound of Formula IB and the reverse transcriptase inhibitor are in separate formulations.

In an embodiment, Formula II and the reverse transcriptase inhibitor are in the same formulation. In another embodiment, Formula II and the reverse transcriptase inhibitor are in separate formulations.

In an embodiment, Formula III and the reverse transcriptase inhibitor are in the same formulation. In another embodiment, Formula III and the reverse transcriptase inhibitor are in separate formulations.

In an embodiment, Compound 1 and the reverse transcriptase inhibitor are in the same formulation. In another embodiment, Compound 1 and the reverse transcriptase inhibitor are in separate formulations.

In an embodiment, Compound 2 or Compound 3 and the reverse transcriptase inhibitor are in the same formulation. In another embodiment, Compound 2 or Compound 3 and the reverse transcriptase inhibitor are in separate formulations.

In an embodiment of the method, the patient is resistant or refractory to treatment with a reverse transcriptase inhibitor. In another embodiment, the patient is resistant or refractory to treatment with a nucleoside agent. In yet another embodiment, the patient is a treatment naïve patient.

In an embodiment, Compound 1 is administered in an amount from 600 mg per day to 3000 mg per day (inclusive of, e.g., about 600, about 800, about 1000, about 1200, about 1400, about 1600, about 1800, about 2000 mg). In an embodiment, Compound 1 is administered in an amount from 600 mg per day to 3000 mg per day. In a particular embodiment, Compound 1 is administered in an amount of about 2000 mg per day. In a further embodiment, Compound 1 is administered in an amount of about 1000 mg twice per day.

In an embodiment, Compound 2 or Compound 3 is administered in an amount from 5 mg per day to 600 mg per day (inclusive of, e.g., about 5, about 25, about 50, about 100, about 200, about 300, about 400, about 500, about 600 mg). In an embodiment, Compound 2 or Compound 3 is administered in an amount from 5 mg per day to 600 mg per day. In a particular embodiment, Compound 2 or Compound 3 is administered in an amount of about 25 mg per day. In a further embodiment, Compound 2 or Compound 3 is administered in an amount of about 10 mg once per day to 200 mg once per day.

In an embodiment provided herein, Compound 1 is in a crystalline form. In a further embodiment, the crystalline form is characterized by X-ray powder diffraction pattern having peaks expressed in degrees-2-theta at angles (±0.2°) of 17.1, 20.8, 22.2, 24.9, and 26.6 (Form XVI).

In another embodiment of the method provided herein, the administration of the compound of Formula I, Formula IA, Formula IB, Formula II, Formula IIIA or Formula IIIB and the reverse transcriptase inhibitor occurs over a period of time shorter than 48 weeks.

In another embodiment of the method provided herein, the administration of Compound 1 and the reverse transcriptase inhibitor occurs over a period of time shorter than 48 weeks.

In another embodiment of the method provided herein, the administration of Compound 2 or Compound 3 and the reverse transcriptase inhibitor occurs over a period of time shorter than 48 weeks.

In an embodiment, the patient is a chronically HBV-infected patient (with or without evidence of underlying liver inflammation).

In an embodiment, the method further comprises the administration of an additional HBV antiviral agent. In a particular embodiment, the additional HBV antiviral agent is pegylated interferon alpha-2a.

In an aspect, provided herein is a method of treating an HBV infection in a patient in need thereof comprising administering to the patient a therapeutically effective amount of a compound of Formula I, Formula IA, Formula IB, Formula II, Formula IIIA or Formula IIIB, or a pharmaceutically acceptable salt thereof, a hydrate thereof, a solvate thereof, or a crystalline form thereof, wherein the patient is resistant or refractory to treatment with a reverse transcriptase inhibitor.

In an aspect, provided herein is a method of treating an HBV infection in a patient in need thereof comprising administering to the patient a therapeutically effective amount of Compound 1 or a pharmaceutically acceptable salt thereof, a hydrate thereof, a solvate thereof, or a crystalline form thereof, wherein the patient is resistant or refractory to treatment with a reverse transcriptase inhibitor.

In another aspect, provided herein is a method of treating an HBV infection in a patient in need thereof comprising administering to the patient a therapeutically effective amount of Compound 2 or Compound 3, or pharmaceutically acceptable salts thereof, hydrates thereof, solvates thereof, or crystalline forms thereof, wherein the patient is resistant or refractory to treatment with a reverse transcriptase inhibitor.

In yet another aspect, provided herein is a method of treating an HBV infection in a patient in need thereof comprising administering to the patient a therapeutically effective amount of a compound of Formula I, Formula IA, Formula IB, Formula II, Formula IIIA or Formula IIIB, or a pharmaceutically acceptable salt thereof, a hydrate thereof, a solvate thereof, or a crystalline form thereof, wherein the patient is resistant or refractory to treatment with a nucleoside agent.

In yet another aspect, provided herein is a method of treating an HBV infection in a patient in need thereof comprising administering to the patient a therapeutically effective amount of Compound 1 or a pharmaceutically acceptable salt thereof, a hydrate thereof, a solvate thereof, or a crystalline form thereof, wherein the patient is resistant or refractory to treatment with a nucleoside agent.

In an embodiment, provided herein is a method of treating an HBV infection in a patient in need thereof comprising administering to the patient a therapeutically effective amount of a Compound 1 and entecavir.

In another embodiment, provided herein is a method of treating an HBV infection in a patient in need thereof comprising administering to the patient a therapeutically effective amount of a Compound 1 and tenofovir.

In another embodiment, provided herein is a method of treating an HBV infection in a patient in need thereof comprising administering to the patient a therapeutically effective amount of a compound of Formula I and entecavir.

In another embodiment, provided herein is a method of treating an HBV infection in a patient in need thereof comprising administering to the patient a therapeutically effective amount of a compound of Formula I and tenofovir.

In another embodiment, provided herein is a method of treating an HBV infection in a patient in need thereof comprising administering to the patient a therapeutically effective amount of a compound of Formula IA and entecavir.

In another embodiment, provided herein is a method of treating an HBV infection in a patient in need thereof comprising administering to the patient a therapeutically effective amount of a compound of Formula IA and tenofovir.

In another embodiment, provided herein is a method of treating an HBV infection in a patient in need thereof comprising administering to the patient a therapeutically effective amount of a compound of Formula IB and entecavir.

In another embodiment, provided herein is a method of treating an HBV infection in a patient in need thereof comprising administering to the patient a therapeutically effective amount of a compound of Formula IB and tenofovir.

In another embodiment, provided herein is a method of treating an HBV infection in a patient in need thereof comprising administering to the patient a therapeutically effective amount of a compound of Formula II and entecavir.

In another embodiment, provided herein is a method of treating an HBV infection in a patient in need thereof comprising administering to the patient a therapeutically effective amount of a compound of Formula II and tenofovir.

In another embodiment, provided herein is a method of treating an HBV infection in a patient in need thereof comprising administering to the patient a therapeutically effective amount of a compound of Formula IIIA and entecavir.

In another embodiment, provided herein is a method of treating an HBV infection in a patient in need thereof comprising administering to the patient a therapeutically effective amount of a compound of Formula IIIA and tenofovir.

In another embodiment, provided herein is a method of treating an HBV infection in a patient in need thereof comprising administering to the patient a therapeutically effective amount of a compound of Formula IIIB and entecavir.

In another embodiment, provided herein is a method of treating an HBV infection in a patient in need thereof comprising administering to the patient a therapeutically effective amount of a compound of Formula IIIB and tenofovir.

In another embodiment, provided herein is a method of treating an HBV infection in a patient in need thereof comprising administering to the patient a therapeutically effective amount of a Compound 2 and entecavir.

In another embodiment, provided herein is a method of treating an HBV infection in a patient in need thereof comprising administering to the patient a therapeutically effective amount of a Compound 2 and tenofovir.

In another embodiment, provided herein is a method of treating an HBV infection in a patient in need thereof comprising administering to the patient a therapeutically effective amount of a Compound 3 and entecavir.

In another embodiment, provided herein is a method of treating an HBV infection in a patient in need thereof comprising administering to the patient a therapeutically effective amount of a Compound 3 and tenofovir.

In an embodiment for treating an HBV infection, Compound 1 is administered in an amount from 600 mg per day to 3000 mg per day (e.g., about 600, about 800, about 1000, about 1200, about 1400, about 1600, about 1800, about 2000 mg). In a further embodiment, Compound 1 is administered in an amount from 600 mg per day to 2000 mg per day. In yet a further embodiment, Compound 1 is administered in an amount of about 2000 mg per day. In an embodiment of this embodiment, Compound 1 is administered in an amount of about 1000 mg twice per day.

In yet another aspect, provided herein is a method of treating an HBV infection in a patient in need thereof comprising administering to the patient a therapeutically effective amount of Compound 2 or Compound 3, or pharmaceutically acceptable salts thereof, hydrates thereof, solvates thereof, or crystalline forms thereof, wherein the patient is resistant or refractory to treatment with a nucleoside agent.

In an embodiment for treating an HBV infection, Compound 2 or Compound 3 is administered in an amount from 5 mg per day to 600 mg per day (e.g., about 5, about 25, about 50, about 100, about 200, about 300, about 400, about 500, about 600 mg). In a further embodiment, Compound 2 or Compound 3 is administered in an amount from 5 mg per day to 600 mg per day. In yet a further embodiment, Compound 2 or Compound 3 is administered in an amount of about 25 mg per day. In an embodiment of this embodiment, Compound 2 or Compound 3 is administered in an amount of about 10 mg once per day to 200 mg once per day.

In another embodiment of these methods, the administration of the compound of Formula I, Formula IA, Formula IB, Formula II, Formula IIIA or Formula IIIB and the reverse transcriptase inhibitor occurs over a period of time shorter than 48 weeks.

In another embodiment of these methods, the administration of Compound 1 and the reverse transcriptase inhibitor occurs over a period of time shorter than 48 weeks.

In another embodiment of these methods, the administration of Compound 2 or Compound 3 and the reverse transcriptase inhibitor occurs over a period of time shorter than 48 weeks.

In another embodiment, the patient is a chronically HBV-infected patient (with or without evidence of underlying liver inflammation).

In an aspect, provided herein is a method of inhibiting replication of a nucleoside resistant HBV variant comprising contacting said variant with an effective amount of a compound of Formula I, Formula IA, Formula IB, Formula II, Formula IIIA or Formula IIIB, or a pharmaceutically acceptable salt thereof, a hydrate thereof, a solvate thereof, or a crystalline form thereof.

In an aspect, provided herein is a method of inhibiting replication of a nucleoside resistant HBV variant comprising contacting said variant with an effective amount of Compound 1, or a pharmaceutically acceptable salt thereof, a hydrate thereof, a solvate thereof, or a crystalline form thereof. In yet another aspect, provided herein is a method of inhibiting replication of a nucleoside resistant HBV variant comprising contacting said variant with an effective amount of Compound 2 or Compound 3 or pharmaceutically acceptable salts thereof, hydrates thereof, solvates thereof, or crystalline forms thereof.

In another aspect, provided herein is a method of treating an HBV infection in a patient in need thereof comprising administering to the patient a therapeutically effective amount of a compound of Formula I, Formula IA, Formula IB, Formula II, Formula IIIA or Formula IIIB, or a pharmaceutically acceptable salt thereof, a hydrate thereof, a solvate thereof, or a crystalline form thereof, and Compound A

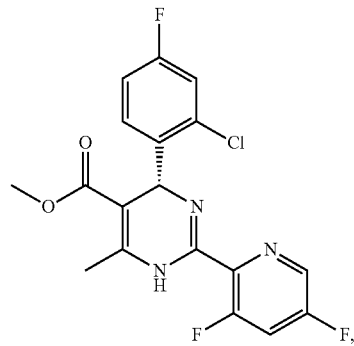

or a pharmaceutically acceptable salt thereof.

In another aspect, provided herein is a method of treating an HBV infection in a patient in need thereof comprising administering to the patient a therapeutically effective amount of Compound 1, or a pharmaceutically acceptable salt thereof, a hydrate thereof, a solvate thereof, or a crystalline form thereof, and Compound A, or a pharmaceutically acceptable salt thereof.

In yet another aspect, provided herein is a method of treating an HBV infection in a patient in need thereof comprising administering to the patient a therapeutically effective amount of Compound 2 or Compound 3, or pharmaceutically acceptable salts thereof, hydrates thereof, solvates thereof, or crystalline forms thereof, and Compound A, or a pharmaceutically acceptable salt thereof.

In another aspect, provided herein is a method of treating an HBV infection in a patient in need thereof comprising administering to the patient a therapeutically effective amount of a compound of Formula I, Formula IA, Formula IB, Formula II, Formula IIIA or Formula IIIB, or a pharmaceutically acceptable salt thereof, a hydrate thereof, a solvate thereof, or a crystalline form thereof, and entecavir, or a pharmaceutically acceptable salt thereof. In an embodiment the compound of Formula I, Formula IA, Formula IB, Formula II, Formula IIIA or Formula IIIB and entecavir are administered at dosages and over time intervals producing a synergistic effect.

In another aspect, provided herein is a method of treating an HBV infection in a patient in need thereof administering to the patient a therapeutically effective amount of Compound 1, or a pharmaceutically acceptable salt thereof, a hydrate thereof, a solvate thereof, or a crystalline form thereof, and entecavir, or a pharmaceutically acceptable salt thereof. In an embodiment Compound 1 and entecavir are administered at dosages and over time intervals producing a synergistic effect.

In another aspect, provided herein is a method of treating an HBV infection in a patient in need thereof comprising administering to the patient a therapeutically effective amount of Compound 2, or pharmaceutically acceptable salts thereof, hydrates thereof, solvates thereof, or crystalline forms thereof, and entecavir, or a pharmaceutically acceptable salt thereof. In an embodiment Compound 2 and entecavir are administered at dosages and over time intervals producing a synergistic effect.

In yet another aspect, provided herein is a method of treating an HBV infection in a patient in need thereof comprising administering to the patient a therapeutically effective amount of Compound 3, or pharmaceutically acceptable salts thereof, hydrates thereof, solvates thereof, or crystalline forms thereof, and entecavir, or a pharmaceutically acceptable salt thereof. In an embodiment Compound 3 and entecavir are administered at dosages and over time intervals producing a synergistic effect.

In another aspect, provided herein is a method of treating an HBV infection in a patient in need thereof comprising administering to the patient a therapeutically effective amount of a compound of Formula I, Formula IA, Formula IB, Formula II, Formula IIIA or Formula IIIB, or pharmaceutically acceptable salts thereof, hydrates thereof, solvates thereof, or crystalline forms thereof, and tenofovir or a pharmaceutically acceptable salt or prodrug thereof. In an embodiment the tenofovir is tenofovir disoproxil fumarate or tenofovir alafenamide fumarate. In a further embodiment the compound of Formula I, Formula IA, Formula IB, Formula II, Formula IIIA or Formula IIIB and tenofovir are administered at dosages and over time intervals producing a synergistic effect.

In another aspect, provided herein is a method of treating an HBV infection in a patient in need thereof comprising administering to the patient a therapeutically effective amount of Compound 1, or a pharmaceutically acceptable salt thereof, a hydrate thereof, a solvate thereof, or a crystalline form thereof, and tenofovir or a pharmaceutically acceptable salt or prodrug thereof. In an embodiment the tenofovir is tenofovir disoproxil fumarate or tenofovir alafenamide fumarate. In a further embodiment Compound 1 and tenofovir are administered at dosages and over time intervals producing a synergistic effect.

In another aspect, provided herein is a method of treating an HBV infection in a patient in need thereof comprising administering to the patient a therapeutically effective amount of Compound 2, or pharmaceutically acceptable salts thereof, hydrates thereof, solvates thereof, or crystalline forms thereof, and tenofovir or a pharmaceutically acceptable salt or prodrug thereof. In an embodiment the tenofovir is tenofovir disoproxil fumarate or tenofovir alafenamide fumarate. In a further embodiment Compound 2 and tenofovir are administered at dosages and over time intervals producing a synergistic effect.

In yet another aspect, provided herein is a method of treating an HBV infection in a patient in need thereof comprising administering to the patient a therapeutically effective amount of Compound 3, or pharmaceutically acceptable salts thereof, hydrates thereof, solvates thereof, or crystalline forms thereof, and tenofovir or a pharmaceutically acceptable salt or prodrug thereof. In an embodiment the tenofovir is tenofovir disoproxil fumarate or tenofovir alafenamide fumarate. In a further embodiment Compound 3 and tenofovir are administered at dosages and over time intervals producing a synergistic effect.

In an embodiment, provided herein is a core protein allosteric modulator (CpAM) and a reverse transcriptase inhibitor for use in therapy.

In an embodiment, provided herein is a compound of Formula I and a reverse transcriptase inhibitor for use in therapy.

In an embodiment, provided herein is a compound of Formula IB and a reverse transcriptase inhibitor for use in therapy.

In an embodiment, provided herein is Compound 1 and a reverse transcriptase inhibitor for use in therapy.

In another embodiment, provided herein is Compound 2 and a reverse transcriptase inhibitor for use in therapy.

In a further embodiment, provided herein is Compound 3 and a reverse transcriptase inhibitor for use in therapy.

In an embodiment, provided herein is a core protein allosteric modulator (CpAM) and a reverse transcriptase inhibitor for use in treating an HBV infection in a patient in need thereof.

In an embodiment, provided herein is a compound of Formula I and a reverse transcriptase inhibitor for use in treating an HBV infection in a patient in need thereof.

In an embodiment, provided herein is a compound of Formula IA and a reverse transcriptase inhibitor for use in treating an HBV infection in a patient in need thereof.

In an embodiment, provided herein is a compound of Formula IB and a reverse transcriptase inhibitor for use in treating an HBV infection in a patient in need thereof.

In an embodiment, provided herein is a compound of Formula II and a reverse transcriptase inhibitor for use in treating an HBV infection in a patient in need thereof.

In an embodiment, provided herein is a compound of Formula IIIA and a reverse transcriptase inhibitor for use in treating an HBV infection in a patient in need thereof.

In an embodiment, provided herein is a compound of Formula IIIB and a reverse transcriptase inhibitor for use in treating an HBV infection in a patient in need thereof.

In an embodiment, provided herein is Compound 1 and a reverse transcriptase inhibitor for use in treating an HBV infection in a patient in need thereof.

In another embodiment, provided herein is Compound 2 and a reverse transcriptase inhibitor for use in treating an HBV infection in a patient in need thereof.

In a further embodiment, provided herein is Compound 3 and a reverse transcriptase inhibitor for use in treating an HBV infection in a patient in need thereof.

In an embodiment, provided herein is a core protein allosteric modulator (CpAM) for use in treating an HBV infection in a patient in need thereof, wherein the CpAM is for use in combination with a reverse transcriptase inhibitor.

In an embodiment, provided herein is a compound of Formula I for use in treating an HBV infection in a patient in need thereof, wherein the compound of Formula I is for use in combination with a reverse transcriptase inhibitor.

In an embodiment, provided herein is a compound of Formula IA for use in treating an HBV infection in a patient in need thereof, wherein the compound of Formula IA is for use in combination with a reverse transcriptase inhibitor.

In an embodiment, provided herein is a compound of Formula IB for use in treating an HBV infection in a patient in need thereof, wherein the compound of Formula IB is for use in combination with a reverse transcriptase inhibitor.

In an embodiment, provided herein is a compound of Formula II for use in treating an HBV infection in a patient in need thereof, wherein the compound of Formula II is for use in combination with a reverse transcriptase inhibitor.

In an embodiment, provided herein is a compound of Formula IIIA for use in treating an HBV infection in a patient in need thereof, wherein the compound of Formula IIIA is for use in combination with a reverse transcriptase inhibitor.

In an embodiment, provided herein is a compound of Formula IIIB for use in treating an HBV infection in a patient in need thereof, wherein the compound of Formula IIIB is for use in combination with a reverse transcriptase inhibitor.

In an embodiment, provided herein is Compound 1 for use in treating an HBV infection in a patient in need thereof, wherein Compound 1 is for use in combination with a reverse transcriptase inhibitor.

In another embodiment, provided herein is Compound 2 for use in treating an HBV infection in a patient in need thereof, wherein Compound 2 is for use in combination with a reverse transcriptase inhibitor.

In a further embodiment, provided herein is Compound 3 for use in treating an HBV infection in a patient in need thereof, wherein Compound 3 is for use in combination with a reverse transcriptase inhibitor.

In an embodiment, provided herein is a reverse transcriptase inhibitor for use in treating an HBV infection in a patient in need thereof, wherein the reverse transcriptase inhibitor is for use in combination with a core protein allosteric modulator (CpAM).

In an embodiment, provided herein is a reverse transcriptase inhibitor for use in treating an HBV infection in a patient in need thereof, wherein the reverse transcriptase inhibitor is for use in combination with a compound of Formula I.

In an embodiment, provided herein is a reverse transcriptase inhibitor for use in treating an HBV infection in a patient in need thereof, wherein the reverse transcriptase inhibitor is for use in combination with a compound of Formula IA.

In an embodiment, provided herein is a reverse transcriptase inhibitor for use in treating an HBV infection in a patient in need thereof, wherein the reverse transcriptase inhibitor is for use in combination with Compound 1.

In an embodiment, provided herein is a reverse transcriptase inhibitor for use in treating an HBV infection in a patient in need thereof, wherein the reverse transcriptase inhibitor is for use in combination with a core protein allosteric modulator (CpAM).

In an embodiment, provided herein is a reverse transcriptase inhibitor for use in treating an HBV infection in a patient in need thereof, wherein the reverse transcriptase inhibitor is for use in combination with a compound of Formula I.

In an embodiment, provided herein is a reverse transcriptase inhibitor for use in treating an HBV infection in a patient in need thereof, wherein the reverse transcriptase inhibitor is for use in combination with a compound of Formula IA.

In an embodiment, provided herein is a reverse transcriptase inhibitor for use in treating an HBV infection in a patient in need thereof, wherein the reverse transcriptase inhibitor is for use in combination with a compound of Formula IB.

In an embodiment, provided herein is a reverse transcriptase inhibitor for use in treating an HBV infection in a patient in need thereof, wherein the reverse transcriptase inhibitor is for use in combination with a compound of Formula II.

In an embodiment, provided herein is a reverse transcriptase inhibitor for use in treating an HBV infection in a patient in need thereof, wherein the reverse transcriptase inhibitor is for use in combination with a compound of Formula IIIA.

In an embodiment, provided herein is a reverse transcriptase inhibitor for use in treating an HBV infection in a patient in need thereof, wherein the reverse transcriptase inhibitor is for use in combination with a compound of Formula IIIB.

In an embodiment, provided herein is a reverse transcriptase inhibitor for use in treating an HBV infection in a patient in need thereof, wherein the reverse transcriptase inhibitor is for use in combination with Compound 1.

In another embodiment, provided herein is a reverse transcriptase inhibitor for use in treating an HBV infection in a patient in need thereof, wherein the reverse transcriptase inhibitor is for use in combination with Compound 2.

In a further embodiment, provided herein is a reverse transcriptase inhibitor for use in treating an HBV infection in a patient in need thereof, wherein the reverse transcriptase inhibitor is for use in combination with Compound 3.

In an embodiment, provided herein is a core protein allosteric modulator (CpAM) and a reverse transcriptase inhibitor for use in combination therapy for treating an HBV infection in a patient in need thereof, wherein the CpAM and the reverse transcriptase inhibitor are for concurrent, sequential or separate administration.

In an embodiment, provided herein is a compound of Formula I and a reverse transcriptase inhibitor for use in combination therapy for treating an HBV infection in a patient in need thereof, wherein the compound of Formula I and the reverse transcriptase inhibitor are for concurrent, sequential or separate administration.

In an embodiment, provided herein is a compound of Formula IA and a reverse transcriptase inhibitor for use in combination therapy for treating an HBV infection in a patient in need thereof, wherein the compound of Formula IA and the reverse transcriptase inhibitor are for concurrent, sequential or separate administration.

In an embodiment, provided herein is a compound of Formula IB and a reverse transcriptase inhibitor for use in combination therapy for treating an HBV infection in a patient in need thereof, wherein the compound of Formula IB and the reverse transcriptase inhibitor are for concurrent, sequential or separate administration.

In an embodiment, provided herein is a compound of Formula II and a reverse transcriptase inhibitor for use in combination therapy for treating an HBV infection in a patient in need thereof, wherein the compound of Formula II and the reverse transcriptase inhibitor are for concurrent, sequential or separate administration.

In an embodiment, provided herein is a compound of Formula IIIA and a reverse transcriptase inhibitor for use in combination therapy for treating an HBV infection in a patient in need thereof, wherein the compound of Formula IIIA and the reverse transcriptase inhibitor are for concurrent, sequential or separate administration.

In an embodiment, provided herein is a compound of Formula IIIB and a reverse transcriptase inhibitor for use in combination therapy for treating an HBV infection in a patient in need thereof, wherein the compound of Formula IIIB and the reverse transcriptase inhibitor are for concurrent, sequential or separate administration.

In an embodiment, provided herein is Compound 1 and a reverse transcriptase inhibitor for use in combination therapy for treating an HBV infection in a patient in need thereof, wherein Compound 1 and the reverse transcriptase inhibitor are for concurrent, sequential or separate administration.

In another embodiment, provided herein is Compound 2 and a reverse transcriptase inhibitor for use in combination therapy for treating an HBV infection in a patient in need thereof, wherein Compound 2 and the reverse transcriptase inhibitor are for concurrent, sequential or separate administration.

In another embodiment, provided herein is Compound 3 and a reverse transcriptase inhibitor for use in combination therapy for treating an HBV infection in a patient in need thereof, wherein Compound 3 and the reverse transcriptase inhibitor are for concurrent, sequential or separate administration.

The daily doses described herein are calculated for an average body weight of about 60 to about 70 kg and should be recalculated in case of pediatric applications, or when used with patients with a substantially diverting body weight.

III. Combination Products and Compositions

In an aspect, provided herein is a combination product comprising a core protein allosteric modulator (CpAM) and a reverse transcriptase inhibitor. In an embodiment of the combination product, the CpAM is a core protein allosteric modulator that causes aberrant, defective or incomplete assembly of HBV capsids. In another embodiment of the combination product, the CpAM is a core protein allosteric modulator that causes assembly of capsids that are essentially empty with respect to their viral contents. In an embodiment of the combination product of Formula I, Formula IA, Formula IB, Formula II, Formula IIIA or Formula IIIB, the reverse transcriptase inhibitor is selected from the group consisting of entecavir, tenofovir, lamivudine, telbivudine, adefovir, clevudine, CMX157, AGX-1009, zidovudine, didanosine, zalcitabine, stavudine, emtricitabine, abacavir, D-D4FC, alovudine, amdoxovir, elvucitabine, delavirdine, efavirenz, nevirapine, capravirine, calanolide A, TMC278, BMS-561390, and DPC-083, or prodrugs thereof and pharmaceutically acceptable salts thereof. Pharmaceutically acceptable prodrugs of tenofovir, for example, include tenofovir disoproxil fumarate and tenofovir alafenamide fumarate.

In embodiments, the combination product comprises at least Compound 1, or a pharmaceutically acceptable salt thereof, a hydrate thereof, a solvate thereof, and entecavir.

In embodiments, the combination product comprises at least Compound 1 or a pharmaceutically acceptable salt thereof, a hydrate thereof, a solvate thereof and tenofovir.

In embodiments, the combination product comprises at least one compound of Formula I and entecavir.

In embodiments, the combination product comprises at least one compound of Formula I and tenofovir.

In embodiments, the combination product comprises at least one compound of Formula IA and entecavir.

In embodiments, the combination product comprises at least one compound of Formula IA and tenofovir.

In embodiments, the combination product comprises at least one compound of Formula IB and entecavir.

In embodiments, the combination product comprises at least one compound of Formula IB and tenofovir.

In embodiments, the combination product comprises at least one compound of Formula II and entecavir.

In embodiments, the combination product comprises at least one compound of Formula II and tenofovir.

In embodiments, the combination product comprises at least one compound of Formula IIIA and entecavir.

In embodiments, the combination product comprises at least one compound of Formula IIIA and tenofovir.

In embodiments, the combination product comprises at least one compound of Formula IIIB and entecavir.

In embodiments, the combination product comprises at least one compound of Formula IIIB and tenofovir.

In embodiments, the combination product comprises at least Compound 1, or a pharmaceutically acceptable salt thereof, a hydrate thereof, a solvate thereof, and entecavir.

In embodiments, the combination product comprises at least Compound 1, or a pharmaceutically acceptable salt thereof, a hydrate thereof, a solvate thereof, and tenofovir.

In embodiments, the combination product comprises at least Compound 2, or a pharmaceutically acceptable salt thereof, a hydrate thereof, a solvate thereof, and entecavir.

In embodiments, the combination product comprises at least Compound 2, or a pharmaceutically acceptable salt thereof, a hydrate thereof, a solvate thereof, and tenofovir.

In embodiments, the combination product comprises at least Compound 3, or a pharmaceutically acceptable salt thereof, a hydrate thereof, a solvate thereof, and entecavir.

In embodiments, the combination product comprises at least Compound 3, or a pharmaceutically acceptable salt thereof, a hydrate thereof, a solvate thereof, and tenofovir.

In an aspect, provided herein is a combination product comprising Compound 1, or pharmaceutically acceptable salts thereof, hydrates thereof, solvates thereof, or crystalline forms thereof, and a reverse transcriptase inhibitor, or a pharmaceutically acceptable salt thereof.

In an embodiment of the combination product, the reverse transcriptase inhibitor is selected from the group consisting of entecavir, tenofovir, lamivudine, telbivudine, adefovir, clevudine, CMX157, AGX-1009, zidovudine, didanosine, zalcitabine, stavudine, emtricitabine, abacavir, D-D4FC, alovudine, amdoxovir, elvucitabine, delavirdine, efavirenz, nevirapine, capravirine, calanolide A, TMC278, BMS-561390, and DPC-083, or prodrugs thereof and pharmaceutically acceptable salts thereof. Pharmaceutically acceptable prodrugs of tenofovir, for example, include tenofovir disoproxil fumarate and tenofovir alafenamide fumarate.

In an embodiment of the combination product, the reverse transcriptase inhibitor is selected from the group consisting of entecavir, tenofovir and lamivudine, or pharmaceutically acceptable salts thereof. Pharmaceutically acceptable prodrugs of tenofovir include tenofovir disoproxil fumarate and tenofovir alafenamide fumarate.

In another aspect, provided herein is a combination product comprising Compound 2, or pharmaceutically acceptable salts thereof, hydrates thereof, solvates thereof, or crystalline forms thereof, and a reverse transcriptase inhibitor, or a pharmaceutically acceptable salt thereof.

In an embodiment of the combination product of Compound 2, the reverse transcriptase inhibitor is selected from the group consisting of entecavir, tenofovir, lamivudine, telbivudine, adefovir, clevudine, CMX157, AGX-1009, zidovudine, didanosine, zalcitabine, stavudine, emtricitabine, abacavir, D-D4FC, alovudine, amdoxovir, elvucitabine, delavirdine, efavirenz, nevirapine, capravirine, calanolide A, TMC278, BMS-561390, and DPC-083, or prodrugs thereof and pharmaceutically acceptable salts thereof. Pharmaceutically acceptable prodrugs of tenofovir, for example, include tenofovir disoproxil fumarate and tenofovir alafenamide fumarate.

In yet another aspect, provided herein is a combination product comprising Compound 3, or pharmaceutically acceptable salts thereof, hydrates thereof, solvates thereof, or crystalline forms thereof, and a reverse transcriptase inhibitor, or a pharmaceutically acceptable salt thereof.

In an embodiment of the combination product of Compound 3, the reverse transcriptase inhibitor is selected from the group consisting of entecavir, tenofovir, lamivudine, telbivudine, adefovir, clevudine, CMX157, AGX-1009, zidovudine, didanosine, zalcitabine, stavudine, emtricitabine, abacavir, D-D4FC, alovudine, amdoxovir, elvucitabine, delavirdine, efavirenz, nevirapine, capravirine, calanolide A, TMC278, BMS-561390, and DPC-083, or prodrugs thereof and pharmaceutically acceptable salts thereof. Pharmaceutically acceptable prodrugs of tenofovir, for example, include tenofovir disoproxil fumarate and tenofovir alafenamide fumarate.

In an embodiment of the combination product, Compound 1 and the reverse transcriptase inhibitor are in the same formulation. In another embodiment of the combination product, Compound 1 and the reverse transcriptase inhibitor are in separate formulations. In a further embodiment of this embodiment, the formulations are for simultaneous or sequential administration.

In an embodiment of the combination product, Compound 2 or Compound 3 and the reverse transcriptase inhibitor are in the same formulation. In another embodiment of the combination product, Compound 2 or Compound 3 and the reverse transcriptase inhibitor are in separate formulations. In a further embodiment of this embodiment, the formulations are for simultaneous or sequential administration.

In an embodiment, the combination product is for use in the treatment of HBV infection in a patient.

In an embodiment, the combination product is for use in the treatment of HBV infection in a patient, wherein the patient is resistant to treatment with a reverse transcriptase inhibitor. In another embodiment, the combination product is for use in the treatment of HBV infection in a patient, wherein the patient is resistant to treatment with a nucleoside agent.

In an embodiment, the combination product is for use in the treatment of HBV infection in a patient, wherein the patient is treatment naïve.

In an embodiment, the combination product of Compound 2 or Compound 3 is for use in the treatment of HBV infection in a patient.

In an embodiment, the combination product of Compound 2 or Compound 3 is for use in the treatment of HBV infection in a patient, wherein the patient is resistant to treatment with a reverse transcriptase inhibitor. In another embodiment, the combination product is for use in the treatment of HBV infection in a patient, wherein the patient is resistant to treatment with a nucleoside agent.

In an embodiment, the combination product of Compound 2 or Compound 3 is for use in the treatment of HBV infection in a patient, wherein the patient is treatment naïve.

In an embodiment, the combination product is for use in the treatment of HBV infection in a patient, wherein the patient is a chronically HBV-infected patient (with or without evidence of underlying liver inflammation).

In an embodiment of the combination product, Compound 1 is in an amount from 600 mg to 3000 mg (e.g., about 600, about 800, about 1000, about 1200, about 1400, about 1600, about 1800, about 2000 mg). In a further embodiment of the combination product, Compound 1 is in an amount from 600 mg to 2000 mg. In another embodiment of the combination product, Compound 1 is in an amount of about 2000 mg. In yet another embodiment of the combination product, Compound 1 is in an amount of about 1000 mg.

In an embodiment of the combination product, Compound 2 or Compound 3 is in an amount from 5 mg to 600 mg (e.g., about 5, about 25, about 50, about 100, about 200, about 300, about 400, about 500, about 600 mg). In a further embodiment of the combination product, Compound 2 or Compound 3 is in an amount from 5 mg to 600 mg. In another embodiment of the combination product, Compound 2 or Compound 3 is in an amount of about 25 mg. In yet another embodiment of the combination product, Compound 2 or Compound 3 is 10 mg to 200 mg.

In an embodiment of the combination product, Compound 1 is in a crystalline form. In a further embodiment, the crystalline form is characterized by X-ray powder diffraction pattern having peaks expressed in degrees-2-theta at angles (±0.2°) of 17.1, 20.8, 22.2, 24.9, and 26.6 (Form XVI).

In an embodiment, the combination product further comprises an additional HBV antiviral agent. In an embodiment, the additional HBV antiviral agent is pegylated interferon alpha-2a.

In an aspect, provided herein is a combination product comprising Compound 1 or a pharmaceutically acceptable salt thereof, a hydrate thereof, a solvate thereof, or a crystalline form thereof, and a reverse transcriptase inhibitor, or a pharmaceutically acceptable salt thereof.

In an embodiment of the combination product, the ratio of CpAM to reverse transcriptase inhibitor is in the range of 700:1-1:40. In another embodiment, the ratio of CpAM to reverse transcriptase inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In an aspect, provided herein is a combination product comprising a compound of Formula I, Formula IA, Formula IB, Formula II, Formula IIIA or Formula IIIB, or a pharmaceutically acceptable salt thereof, a hydrate thereof, a solvate thereof, or a crystalline form thereof, and a reverse transcriptase inhibitor, or a pharmaceutically acceptable salt thereof.

In an embodiment of the combination product, the ratio of Formula I to reverse transcriptase inhibitor is in the range of 700:1-1:40. In another embodiment of the combination product, the ratio of Formula I to reverse transcriptase inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In an embodiment of the combination product, the ratio of Formula IA to reverse transcriptase inhibitor is in the range of 700:1-1:40. In another embodiment of the combination product, the ratio of Formula I to reverse transcriptase inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In an embodiment of the combination product, the ratio of Formula IB to reverse transcriptase inhibitor is in the range of 700:1-1:40. In another embodiment of the combination product, the ratio of Formula I to reverse transcriptase inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In an embodiment of the combination product, the ratio of Formula II to reverse transcriptase inhibitor is in the range of 700:1-1:40. In another embodiment of the combination product, the ratio of Formula I to reverse transcriptase inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In an embodiment of the combination product, the ratio of Formula IIIA to reverse transcriptase inhibitor is in the range of 700:1-1:40. In another embodiment of the combination product, the ratio of Formula I to reverse transcriptase inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In an embodiment of the combination product, the ratio of Formula IIIB to reverse transcriptase inhibitor is in the range of 700:1-1:40. In another embodiment of the combination product, the ratio of Formula I to reverse transcriptase inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In an embodiment of the combination product, the ratio of Compound 1 to entecavir is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In an embodiment of the combination product, the ratio of Compound 1 to tenofovir is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In an embodiment of the combination product, the ratio of Compound 2 to entecavir is in the range of 200:1 to 1:40, for example, 200:1, 175:1, 150:1, 125:1, 100:1, 90:1, 80:1, 70:1, 60:1, 50:1, 40:1, 30:1, 20:1, 15:1, 10:1, 8:1, 5:1, 2:1, 1:1, 1:2, 1:5, 1:8, 1:10, 1:15, 1:20, 1:30, or 1:40. In another embodiment of the combination product, the ratio of Compound 2 to entecavir is in the range of 40:1 to 1:1, for example, 40:1, 30:1, 20:1, 10:1, 8:1, 6:1, 4:1, 2:1, or 1:1. In a further embodiment of the combination product, the ratio of Compound 2 entecavir is in the range of 30:1 to 10:1, for example, 30:1, 20:1 or 10:1. In yet another embodiment of the combination product, the ratio of Compound 2 to entecavir is 20:1.

In an embodiment of the combination product, the ratio of Compound 2 to tenofovir is in the range of 40:1 to 1:40, for example, 40:1, 30:1, 20:1, 15:1, 10:1, 8:1, 5:1, 2:1, 1:1, 1:2, 1:5, 1:8, 1:10, 1:15, 1:20, 1:30, or 1:40. In another embodiment of the combination product, the ratio of Compound 2 to tenofovir is in the range of 10:1 to 1:1, for example, 10:1, 8:1, 6:1, 4:1, 2:1, or 1:1. In a further embodiment of the combination product, the ratio of Compound 2 to tenofovir is in the range of 3:1 to 1:1, for example, 3:1, 2:1 or 1:1. In yet another embodiment of the combination product, the ratio of Compound 2 to tenofovir is 2:1.

In an embodiment of the combination product, the ratio of Compound 3 to entecavir is in the range of 700:1 to 1:30, for example, 700:1, 600:1, 500:1, 400:1, 300:1, 200:1, 190:1, 180:1, 170:1, 160:1, 150:1, 140:1, 130:1, 120:1, 110:1, 100:1, 20:1, 15:1, 10:1, 8:1, 5:1, 2:1, 1:1, 1:2, 1:5, 1:8, 1:10, 1:15, or 1:20. In another embodiment of the combination product, the ratio of Compound 3 to entecavir is in the range of 180:1 to 1:2, for example, 180:1, 170:1, 160:1, 150:1, 140:1, 130:1, 120:1, 110:1, 100:1, 50:1, 20:1, 10:1, 1:1, or 1:2. In a further embodiment of the combination product, the ratio of Compound 3 entecavir is in the range of 170:1 to 150:1, for example, 170:1, 160:1 or 150:1. In yet another embodiment of the combination product, the ratio of Compound 3 to entecavir is 160:1.

In an embodiment of the combination product, the ratio of Compound 3 to tenofovir is in the range of 80:1 to 1:10, for example, 80:1, 70:1, 60:1, 50:1, 40:1, 30:1, 20:1, 15:1, 10:1, 1:1, or 1:10. In another embodiment of the combination product, the ratio of Compound 3 to tenofovir is in the range of 10:1 to 1:10, for example, 10:1, 8:1, 6:1, 4:1, 2:1, 1:1, 1:2, 1:4, 1:6, 1:8, and 1:10. In a further embodiment of the combination product, the ratio of Compound 3 tenofovir is in the of range 2:1 to 1:2, for example, 2:1, 1:1, or 1:2. In yet another embodiment of the combination product, the ratio of Compound 3 to tenofovir is 1:1.

In another aspect, provided herein is a pharmaceutical composition comprising Compound 1, or a pharmaceutically acceptable salt thereof, a hydrate thereof, a solvate thereof, or a crystalline form thereof, and a reverse transcriptase inhibitor, or a pharmaceutically acceptable salt thereof.

In an embodiment of the pharmaceutical composition, the reverse transcriptase inhibitor is selected from the group consisting of entecavir, tenofovir (including, e.g., prodrugs thereof such tenofovir disoproxil and tenofovir alafenamide) and lamivudine, or pharmaceutically acceptable salts thereof.

In another embodiment, the pharmaceutical composition further comprises one or more pharmaceutically acceptable carriers.

In another aspect, provided herein is a pharmaceutical composition comprising a compound of Formula I, Formula IA, Formula IB, Formula II, Formula IIIA or Formula IIIB, or pharmaceutically acceptable salts thereof, hydrates thereof, solvates thereof, or crystalline forms thereof, and a reverse transcriptase inhibitor, or a pharmaceutically acceptable salt thereof.

In an embodiment of the pharmaceutical composition of Formula I, Formula IA, Formula IB, Formula II, Formula IIIA or Formula IIIB, the reverse transcriptase inhibitor is selected from the group consisting of entecavir, tenofovir, lamivudine, telbivudine, adefovir, clevudine, CMX157, AGX-1009, zidovudine, didanosine, zalcitabine, stavudine, emtricitabine, abacavir, D-D4FC, alovudine, amdoxovir, elvucitabine, delavirdine, efavirenz, nevirapine, capravirine, calanolide A, TMC278, BMS-561390, and DPC-083, or prodrugs thereof and pharmaceutically acceptable salts thereof. Pharmaceutically acceptable prodrugs of tenofovir, for example, include tenofovir disoproxil fumarate and tenofovir alafenamide fumarate.

In another embodiment, the pharmaceutical composition of Formula I, Formula IA, Formula IB, Formula II, Formula IIIA or Formula IIIB further comprises one or more pharmaceutically acceptable carriers.

In another aspect, provided herein is a pharmaceutical composition comprising Compound 1, or pharmaceutically acceptable salts thereof, hydrates thereof, solvates thereof, or crystalline forms thereof, and a reverse transcriptase inhibitor, or a pharmaceutically acceptable salt thereof.

In an embodiment of the pharmaceutical composition of Compound 1, the reverse transcriptase inhibitor is selected from the group consisting of entecavir, tenofovir, lamivudine, telbivudine, adefovir, clevudine, CMX157, AGX-1009, zidovudine, didanosine, zalcitabine, stavudine, emtricitabine, abacavir, D-D4FC, alovudine, amdoxovir, elvucitabine, delavirdine, efavirenz, nevirapine, capravirine, calanolide A, TMC278, BMS-561390, and DPC-083, or prodrugs thereof and pharmaceutically acceptable salts thereof. Pharmaceutically acceptable prodrugs of tenofovir, for example, include tenofovir disoproxil fumarate and tenofovir alafenamide fumarate.

In another embodiment, the pharmaceutical composition of Compound 1 further comprises one or more pharmaceutically acceptable carriers.

In another aspect, provided herein is a pharmaceutical composition comprising Compound 2, or pharmaceutically acceptable salts thereof, hydrates thereof, solvates thereof, or crystalline forms thereof, and a reverse transcriptase inhibitor, or a pharmaceutically acceptable salt thereof.

In an embodiment of the pharmaceutical composition of Compound 2, the reverse transcriptase inhibitor is selected from the group consisting of entecavir, tenofovir, lamivudine, telbivudine, adefovir, clevudine, CMX157, AGX-1009, zidovudine, didanosine, zalcitabine, stavudine, emtricitabine, abacavir, D-D4FC, alovudine, amdoxovir, elvucitabine, delavirdine, efavirenz, nevirapine, capravirine, calanolide A, TMC278, BMS-561390, and DPC-083, or prodrugs thereof and pharmaceutically acceptable salts thereof. Pharmaceutically acceptable prodrugs of tenofovir, for example, include tenofovir disoproxil fumarate and tenofovir alafenamide fumarate.

In another embodiment, the pharmaceutical composition of Compound 2 further comprises one or more pharmaceutically acceptable carriers.

In yet another aspect, provided herein is a pharmaceutical composition comprising Compound 3, or pharmaceutically acceptable salts thereof, hydrates thereof, solvates thereof, or crystalline forms thereof, and a reverse transcriptase inhibitor, or a pharmaceutically acceptable salt thereof.

In an embodiment of the pharmaceutical composition of Compound 3, the reverse transcriptase inhibitor is selected from the group consisting of entecavir, tenofovir, lamivudine, telbivudine, adefovir, clevudine, CMX157, AGX-1009, zidovudine, didanosine, zalcitabine, stavudine, emtricitabine, abacavir, D-D4FC, alovudine, amdoxovir, elvucitabine, delavirdine, efavirenz, nevirapine, capravirine, calanolide A, TMC278, BMS-561390, and DPC-083, or prodrugs thereof and pharmaceutically acceptable salts thereof. Pharmaceutically acceptable prodrugs of tenofovir, for example, include tenofovir disoproxil fumarate and tenofovir alafenamide fumarate.

In another embodiment, the pharmaceutical composition of Compound 3 further comprises one or more pharmaceutically acceptable carriers.

In another aspect, the present disclosure provides a kit for treating HBV infections, comprising a CpAM, Compound 1, Compound 2, or Compound 3, or pharmaceutically acceptable salts thereof, hydrates thereof, solvates thereof, or crystalline forms thereof, in an amount from 600 mg per day to 3000 mg per day, and a reverse transcriptase inhibitor. In another embodiment, the present disclosure provides a kit for treating HBV infections, comprising at least two or more of the group consisting of a CpAM, Compound 1, Compound 2, or Compound 3, or pharmaceutically acceptable salts thereof, hydrates thereof, solvates thereof, or crystalline forms thereof, in an amount from 600 mg per day to 3000 mg per day; a reverse transcriptase inhibitor; and an additional HBV antiviral agent. In some embodiments, the kit further comprises packaging and instructions. In certain embodiments, the kit comprises a pharmaceutical product comprising a pharmaceutical composition comprising a CpAM, Compound 1, Compound 2, or Compound 3, or pharmaceutically acceptable salts thereof, hydrates thereof, solvates thereof, or crystalline forms thereof, and a pharmaceutically acceptable carrier or diluent; and a pharmaceutical composition comprising a reverse transcriptase inhibitor and a pharmaceutically acceptable carrier or diluent.

In some embodiments, the kit comprises a pharmaceutical composition comprising a CpAM, Compound 1, Compound 2, or Compound 3, or pharmaceutically acceptable salts thereof, hydrates thereof, solvates thereof, or crystalline forms thereof; an additional HBV antiviral agent; and a pharmaceutically acceptable carrier or diluent. In another embodiment, the kit comprises a pharmaceutical product comprising:

a pharmaceutical composition comprising a CpAM, Compound 1, Compound 2, or Compound 3, or pharmaceutically acceptable salts thereof, hydrates thereof, solvates thereof, or crystalline forms thereof, in an amount from 600 mg to 3000 mg, and a pharmaceutically acceptable carrier or diluent; and a reverse transcriptase inhibitor;

a sealed container for housing the pharmaceutical composition;

a sealed contained for housing the reverse transcriptase inhibitor; and instructions for use.

In yet another embodiment, the kit comprises a pharmaceutical product comprising at least two or more of the group consisting of:

a pharmaceutical composition comprising a CpAM, Compound 1, Compound 2, or Compound 3, or pharmaceutically acceptable salts thereof, hydrates thereof, solvates thereof, or crystalline forms thereof, in an amount from 600 mg to 3000 mg, and a pharmaceutically acceptable carrier or diluent;

a reverse transcriptase inhibitor; and an additional HBV antiviral agent;

further comprising:

a sealed container for housing the pharmaceutical composition;

a sealed contained for housing the interferon; and instructions for use.

In additional embodiments, pharmaceutical kits are provided. The kit includes a sealed container approved for the storage of pharmaceutical compositions, the container containing one of the above-described pharmaceutical compositions. In some embodiments, the sealed container minimizes the contact of air with the ingredients, e.g. an airless bottle. In other embodiments, the sealed container is a sealed tube. An instruction for the use of the composition and the information about the composition are to be included in the kit.

EXAMPLES

Example 1

Antiviral Activity of Compound 1 Against Lamivudine-, Tenofovir-, and Entecavir-Resistant HBV Variants In this example, the antiviral activity of Compound 1 was determined using HepG2 liver cells transiently transfected with plasmids expression replication-competent HBV DNA and quantitation of intracellular encapsidated HBV DNA. The antiviral activity of Compound 1 was measured against nucleoside inhibitor sensitive, wild-type HBV, as well as against HBV variants resistant to nucleoside analogs that contain defined amino acid changes in the coding sequence of the reverse transcriptase protein: rtL180M/M204V, rtN236T, rtA181V, rtA181V/N236T, and rtL180M/M204V/N236T.

Example 1.1

Materials and Methods

Compounds

Compound 1 was synthesized. Lamivudine (LMV), entecavir (ETV), and tenofovir disoproxil fumarate (TDF) were purchased from Toronto Research Chemicals (Toronto, Canada), which chemical structures are shown below as Compounds (IV), (V) and (VI), respectively.

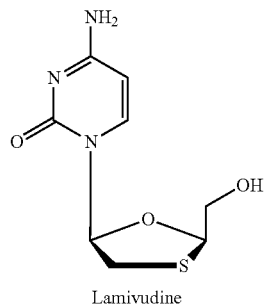
Lamivudine (IV)

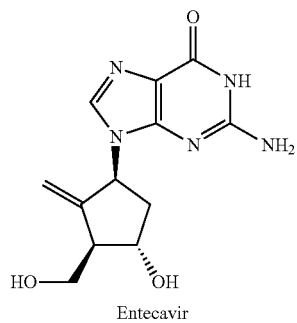
Entecavir (V)

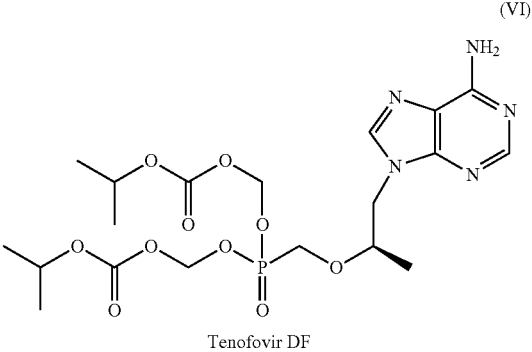
Tenofovir DF (VI)

HBV Plasmids

Plasmid DNA constructs containing a 1.1×HBV genome under the control of a CMV promoter were previously cloned from serum of an HBV infected patient prior to LMV treatment (Genbank AY220698, Fudan University, China; SEQ ID NO:1, see Table 1) and after development of resistance to LMV (Genbank AY220697, Fudan University, China; SEQ ID NO:2, see Table 1) (Zhang J M et al. 2005. J Med Virol 77: 203-208). Genotyping analysis confirmed that both isolates belong to genotype B HBV, and that the isolate collected after the development of resistance to LMV contained two amino acid changes within the polymerase gene (L180M/M204V). The HBV variant was named rtL180M/M204V to indicate that the amino acid changes were present in the reverse transcriptase (rt) protein. Two additional plasmids were generated by introducing coding sequence changes resulting in the amino acid changes N236T and A181V in the HBV polymerase, respectively. The nucleotide changes were introduced into the wild type genotype B plasmid by site directed mutagenesis according to manufacturer recommendation (Agilent Technologies; Santa Clara, Calif.; Catalog#200519) using the following primers and their corresponding reverse complement sequence (nucleotide change underlined): 5'-CTT TGG GTA TAC ATT TAA CCC CTC ACA AAA C-3' (rtN236T; SEQ ID NO:3), 5'-GTC CGT TTC TCT TGG TTC AGT TTA CTA GTG-3' (rtA181V; SEQ ID NO:4). In two additional plasmid constructs, the rtN236T amino acid change was also added into the rtA181V and rtL180M/M204V plasmids to generate the rtA181V/N236T double mutant and rtL180M/M204V/N236T triple mutant HBV variants, respectively. The full length HBV genome was sequenced in all plasmids to confirm that only the intended nucleotide change(s) were present in the final HBV expression constructs.

TABLE 1

| HBV genome sequences for plasmid constructs |
|---|

```
SEQ ID NO: 1
aactccacca ctttccacca aactcttcaa gatcccagag tcagggccct gtactttcct    60
gctggtggct ccagttcagg aacagtgagc cctgctcaaa atactgtctc tgccatatcg   120
tcaatcttat cgaaaactgg ggaccctgta ccgaacatgg agaacatcgc atcaggactc   180
ctaggacccc tgctcgtgtt acaggcgggg ttttccttgt tgacaaaaat cctcacaata   240
ccacagagtc tagactcgtg gtggacttct ctcaatttc taggggggaac acccgtgtgt   300 cttggccaaa attcgcagtc ccaaatctcc agtcactcac caacctgttg tcctccaatt   360
tgtcctggtt atcgctggat gtatctgcgg cgttttatca tattcctctg catcctgctg   420
ctatgcctca tcttcttgtt ggttcttctg gactatcaag gtatgttgcc cgtttgtcct   480
```

TABLE 1-continued

HBV genome sequences for plasmid constructs

| | |
|---|---|
| ctaattccag gatcatcaac aaccagcacc ggaccatgca aaacctgcac gactcctgct | 540 |
| caaggaacct ctatgtttcc ctcatgttgc tgtacaaaac ctacggacgg aaactgcacc | 600 |
| tgtattccca tcccatcatc ttgggctttc gcaaaattcc tatgggagtg ggcctcagtc | 660 |
| cgtttctctt ggctcagttt actagtgcca tttgttcagt ggttcgtagg gctttccccc | 720 |
| actgtctggc tttcagttat atggatgatt tggttttggg ggccaagtct gtacaacatc | 780 |
| ttgagtccct ttatgccgct gttaccaatt ttcttttgtc tttgggtata catttaaacc | 840 |
| ctcacaaaac aaaagatgg ggatattccc ttaactttat gggatatgta attgggagtt | 900 |
| ggggcacatt gccacaggaa catattgtac aaaaaatcaa aatatgtttt aggaaacttc | 960 |
| ctgtaaacag gcctattgat tggaaagtct gtcaacgaat tgtgggtctt ttggggtttg | 1020 |
| ccgcccttt cacgcaatgt ggatatcctg ctttaatgcc tttatatgca tgtatacaag | 1080 |
| caaaacaggc ttttattttc tcgccaactt acaaggcctt tctgagtaaa cagtatttga | 1140 |
| acctttaccc cgttgctcgg caacggcctg gtctgtgcca agtgtttgct gacgcaaccc | 1200 |
| ccactggttg gggcttggcc ataggccatc agcgcatgcg tggcaccttt gtgtctcctc | 1260 |
| tgccgatcca tactgcggaa ctcctagccg cttgttttgc tcgcagcagg tctgggcaa | 1320 |
| aactcatcgg gactgacaat tctgtcgtgc tctcccgcaa gtatacatca tttccatggc | 1380 |
| tgctaggctg tgctgccaac tggatcctgc gcgggacgtc attgatac gtcccgtcgg | 1440 |
| cgctgaatcc cgcggacgac ccctcccggg gccgcttggg gctctaccgc ccgcttctcc | 1500 |
| gcctgttgta ccgaccgacc acggggcgca cctctcttta cgcggactcc ccgtctgtgc | 1560 |
| cttctcatct gccggaccgt gtgcacttcg cttcacctct gcacgtcgca tggaaaccac | 1620 |
| cgtgaacgcc cacaggaacc tgcccaaggt cttgcataag aggactcttg gactttcagc | 1680 |
| aatgtcaacg accgaccttg aggcatactt caaagactgt gtgtttactg agtgggagga | 1740 |
| gttgggggag gaggttaggt taatgatctt tgtactagga ggctgtaggc ataaattggt | 1800 |
| gtgttcacca gcaccatgca actattcac ctctgcctaa tcatctcatg ttcatgtcct | 1860 |
| actgttcaag cctccaagct gtgccttggg tggctttggg gcatggacat tgacccgtat | 1920 |
| aaagaatttg gagcttctgt ggagttactc tcttttttgc cactgactt ctttccttct | 1980 |
| attcgagatc tcctcgacac cgcctctgct ctgtatcggg aggccttaga gtctccggaa | 2040 |
| cattgttcac ctcaccatac ggcactcagg caagctattc tgtgttgggg tgagttaatg | 2100 |
| aatctagcca cctgggtggg aagtaatttg gaagatccag catccaggga attagtagtc | 2160 |
| agctatgtca acgttaatat gggcctaaaa atcagacaac tattgtggtt tcacatttcc | 2220 |
| tgtcttactt ttgggagaga aactgttctt gaatatttgg tgtcttttgg agtgtggatt | 2280 |
| cgcactcctc ccgcatatag accgccaaat gcccctatct tatcaacact tccggaaact | 2340 |
| actgagtta gacgaagagg caggtcccct agaagaagaa ctccctcgcc tcgcagacga | 2400 |
| aggtctcaat cgccgcgtcg cagaagatct caatctcggg aatctcaatg ttagtattcc | 2460 |
| ttggacacac aaggtgggaa actttacggg gctttattct tctacggtac cttgctttaa | 2520 |
| tcctaaatgg caaactcctt cttttcctga cattcatttg caggaggaca ttgttgatag | 2580 |
| atgtaagcaa tttgtggggc cccttacagt aaatgaaaac aggagactta aattaattat | 2640 |
| gcctgctagg ttttatccca atgttactaa atatttgccc ttagataaag ggatcaaacc | 2700 |
| gtattatcca gagtatgtag ttaatcatta cttccgacg cgacattatt tacacactct | 2760 |
| ttggaaggcg gggatcttat ataaaagaga gtccacacgt agcgcctcat tttgcgggtc | 2820 |

TABLE 1-continued

HBV genome sequences for plasmid constructs

| | | | | | |
|---|---|---|---|---|---|
| accatattct | tgggaacaag | atctacagca | tgggaggttg | gtcttccaaa | cctcgaaaag | 2880 |
| gcatggggac | aaatctttct | gtccccaatc | ccctgggatt | cttccccgat | catcagttgg | 2940 |
| accctgcatt | caaagccaac | tcagaaaatc | cagattggga | cctcaacccg | cacaaggaca | 3000 |
| actggccgga | cgccaacaag | gtgggagtgg | gagcattcgg | gccagggttc | accccctccc | 3060 |
| atggggggact | gttggggtgg | agccctcagg | ctcagggcct | actcacaact | gtgccagcag | 3120 |
| ctcctcctcc | tgcctccacc | aatcggcagt | taggaaggca | gcctactccc | ttatctccac | 3180 |
| ctctaaggga | cactcatcct | caggccatgc | agtgg | | | 3215 |

SEQ ID NO: 2

| | | | | | |
|---|---|---|---|---|---|
| aactccacca | ctttccacca | aactcttcaa | gatcccagag | tcagggccct | gtactttcct | 60 |
| gctggtggct | ccagttcagg | aacagtgagc | cctgctcaga | atactgtctc | tgccatatcg | 120 |
| tcaatcttat | cgaagactgg | ggaccctgta | ccgaacatgg | agaacatcgc | atcaggactc | 180 |
| ctaggacccc | tgctcgtgtt | accggcgggg | ttttccttgt | tgacaaaaat | cctcacaata | 240 |
| ccacagagtc | tagactcgtg | gtggacttct | ctcagttttc | taggggggaac | acccgtgtgt | 300 |
| cgtggccaaa | attcgcagtc | ccaaatctcc | agtcactcac | caacctgttg | tcctccaatt | 360 |
| tgtcctggtt | atcgctggat | gtgtctgcgg | cgttttatca | tattcctctg | catcctgctg | 420 |
| ctatgcctca | tcttcttgtt | ggttcttctg | gactatcaag | gtatgttgcc | cgtttgtcct | 480 |
| ctaattccag | gatcatcaac | aaccagcacc | ggaccatgca | aaacctgcac | gactcctgct | 540 |
| caaggaacct | ctatgtttcc | ctcatgttgc | tgtacaaaac | ctacgacgg | aaactgcacc | 600 |
| tgtattccca | tcccatcatc | ttgggctttc | gcaaaattcc | tatgggagtg | ggcctcagtc | 660 |
| cgtttctcat | ggctcagttt | actagtgcca | tttgttcagt | ggttcgtagg | gctttccccc | 720 |
| actgtctggc | tttcagttat | gtggatgatt | tggttttggg | ggccaagtct | gtacaacatc | 780 |
| ttgagtccct | ttatgccgct | gttaccaatt | ttcttttgtc | tttgggtata | catttaaacc | 840 |
| ctcacaaaac | aaaaagatgg | ggatattccc | ttaacttcat | gggatatgta | attgggagtt | 900 |
| ggggcacatt | gccacaggaa | catattgtac | aaaaaatcaa | aatgtgtttt | aggaaacttc | 960 |
| ctgtaaacag | gccattgat | tggaaagtct | gtcaacgaat | tgtgggtctt | tggggttttg | 1020 |
| ccgcccctttt | cacgcaatgt | ggatatcctg | ctttaatgcc | tttatatgca | tgtatacaag | 1080 |
| caaaacaggc | ttttatttc | tcgccaactt | acaaggcctt | tctgagtaaa | cagtatctga | 1140 |
| acctttaccc | cgttgctcgg | caacggcctg | gtctgtgcca | agtgtttgct | gacgcaaccc | 1200 |
| ccactggttg | gggcttggcc | ataggccatc | agcgcatgcg | tggaaccttt | gtgtctcctc | 1260 |
| tgccgatcca | tactgcggaa | ctcctagccg | cttgttttgc | tcgcagcagg | tctgggcaa | 1320 |
| aactcatcgg | gactgacaat | tctgtcgtgc | tctcccgcaa | gtatacatca | tttccatggc | 1380 |
| tgctaggctg | tgctgccaac | tggatcctgc | gcgggacgtc | attgatac | gtcccgtcgg | 1440 |
| cgctgaatcc | cgcggacgac | ccctcccggg | gccgcttggg | gctctaccgc | ccgcttctcc | 1500 |
| gcctgttgta | ccgaccgacc | acggggcgca | cctctcttta | cgcggactcc | ccgtctgtgc | 1560 |
| cttctcatct | gccggaccgt | gtgcacttcg | cttcacctct | gcacgtcgca | tggaaaccac | 1620 |
| cgtgaacgcc | cactggaacc | tgcccaaggt | cttgcataag | aggactcttg | gactacagc | 1680 |
| aatgtcaacg | accgaccttg | aggcatactt | caaagactgt | gtgttcaatg | agtgggagga | 1740 |
| gttgggggag | gagtttaagt | taatgatctt | tgtactagga | ggctgtaggc | ataaattggt | 1800 |
| gtgttcacca | gcaccatgca | actattcac | ctctgcctaa | tcatctcttg | ttcatgtcct | 1860 |
| actgttcaag | cctccaagct | gtgccttggg | tggctttagg | gcatggacat | tgacacgtat | 1920 |

TABLE 1-continued

HBV genome sequences for plasmid constructs

```
aaagaatttg gagcttctgt ggaattactc tctttttgc cactgactt ctttccttct    1980 attcgagatc tcctcgacac cgccactgct ctgtatcggg aggccttaga gtctccggaa    2040
cattgttcac ctcaccatac ggcactcagg caagctattc tgtgttgggg tgagttaatg    2100
aatctagcca cctgggtggg aagtaatttg gaagatcaag catccaggga tttagtagtc    2160
ggctatgtca acgttaatat gggcctaaaa ctcagacaac tattgtggtt tcacatttcc    2220
tgtcttactt ttggaagaga aactgttctt gaatatttgg tgtcttttgg agtgtggatt    2280
cgcactcctc ccgcatatag accgccaaat gcccctatct tatcaacact tccggaaact    2340 actgagtta gacgaagagg caggtcccct agaagaagaa ctccctcgcc tcgcagacga    2400
aggtctcaat cgccgcgtcg cagaagatct aaatctcggg aatctcaatg ttagtattcc    2460
ttggacacac aaggtgggaa actttacggg gctttattct tctacggtac cttgctttaa    2520
tcctaaatgg caaactcctt cttttcctga cattcatttg caggaggaca ttgttgatag    2580
atgtaagcaa tttgtggggc cccttacagt aaatgaaaat aggagactta aattaattat    2640
gcctgctagg ttttatccca atgttactaa atatttgccc ttagataaag ggatcaaacc    2700
gtattatcca gagtatgtag ttgatcatta cttccagacg cgacattatt tacacactct    2760
ttggaaggcg gggatcttat ataaaagaga gtccacacgt agcgcctcat tttgcgggtc    2820
accatattct tgggaacaag atctacagca tgggaggttg gtcttccaaa cctcgaaaag    2880
gcatggggac aaatctttct gtccccaatc ccctgggatt cttccccgat catcagttgg    2940
accctgcatt caaagccaac tcagaaaatc cagattggga cctcaacccg tacaaggaca    3000
actggccgga cgccaacaag gtgggagtgg gagcattcgg gccagggttc accctctccc    3060 atggggact gttgggttgg agccctcagg ctcaggtct actcacaact gtgccagcag    3120
ctcctcctcc tgcctccacc aatcggcagt taggaaggca gcctactccc ttatctccac    3180
ctctaaggga cactcatcct caggccatac agtgg                                3215
```

SEQ ID NO: 5
```
aactccacca ctttccacca aactcttcaa gatcccagag tcagggccct gtactttcct     60
gctggtggct ccagttcagg aacagtgagc cctgctcaga atactgtctc tgccatatcg    120
tcaatcttat cgaagactgg ggaccctgta ccgaacatgg agaacatcgc atcaggactc    180
ctaggacccc tgctcgtgtt accggcgggg ttttccttgt tgacaaaaat cctcacaata    240
ccacagagtc tagactcgtg gtggacttct ctcagtttc taggggggaac acccgtgtgt    300 cgtggccaaa attcgcagtc ccaaatctcc agtcactcac caacctgttg tcctccaatt    360
tgtcctggtt atcgctggat gtgtctgcgg cgttttatca tattcctctg catcctgctg    420
ctatgcctca tcttcttgtt ggttcttctg gactatcaag gtatgttgcc cgtttgtcct    480
ctaattccag gatcatcaac aaccagcacc ggaccatgca aaacctgcac gactcctgct    540
caaggaacct ctatgtttcc ctcatgttgc tgtacaaaac ctacggacgg aaactgcacc    600
tgtattccca tcccatcatc ttgggctttc gcaaaattcc tatgggagtg gcctcagtc    660 cgtttctcat ggctcagttt actagtgcca tttgttcagt ggttcgtagg gctttccccc    720
actgtctggc tttcagttat gtggatgatt tggttttggg ggccaagtct gtacaacatc    780
ttgagtccct ttatgccgct gttaccaatt ttcttttgtc tttgggtata catttaaacc    840
ctcacaaaac aaaagatgg ggatattccc ttaacttcat gggatatgta attgggagtt    900
ggggcacatt gccacaggaa catattgtac aaaaaatcaa aatgtgtttt aggaaacttc    960
```

TABLE 1-continued

HBV genome sequences for plasmid constructs

```
ctgtaaacag gcctattgat tggaaagtct gtcaacgaat tgtgggtctt ttggggtttg   1020
ccgccccttt cacgcaatgt ggatatcctg ctttaatgcc tttatatgca tgtatacaag   1080
caaaacaggc ttttattttc tcgccaactt acaaggcctt tctgagtaaa cagtatctga   1140
accttacccc cgttgctcgg caacggcctg gtctgtgcca agtgtttgct gacgcaaccc   1200
ccactggttg gggcttggcc ataggccatc agcgcatgcg tggaaccttt gtgtctcctc   1260
tgccgatcca tactgcggaa ctcctagccg cttgttttgc tcgcagcagg tctgggcaa    1320
aactcatcgg gactgacaat tctgtcgtgc tctcccgcaa gtatacatca tttccatggc   1380
tgctaggctg tgctgccaac tggatcctgc gcgggacgtc attgatac gtcccgtcgg     1440
cgctgaatcc cgcggacgac ccctcccggg gccgcttggg gctctaccgc ccgcttctcc   1500
gcctgttgta ccgaccgacc acggggcgca cctctcttta cgcggactcc ccgtctgtgc   1560
cttctcatct gccggaccgt gtgcacttcg cttcacctct gcacgtcgca tggaaaccac   1620
cgtgaacgcc cactggaacc tgcccaaggt cttgcataag aggactcttg gactacagc    1680
aatgtcaacg accgaccttg aggcatactt caaagactgt gtgttcaatg agtggggagga 1740
gttgggggag gagtttaagt taatgatctt tgtactagga ggctgtaggc ataaattggt   1800
gtgttcacca gcaccatgca actattcac ctctgcctaa tcatctcttg ttcatgtcct    1860
actgttcaag cctccaagct gtgccttggg tggctttagg gcatggacat tgacacgtat   1920
aaagaatttg gagcttctgt ggaattactc tcttttttgc cactgactt ctttccttct    1980
attcgagatc tcctcgacac cgccactgct ctgtatcggg aggccttaga gtctccggaa   2040
cattgttcac ctcaccatac ggcactcagg caagctattc tgtgttgggg tgagttaatg   2100
aatctagcca cctgggtggg aagtaatttg gaagatcaag catccaggga tttagtagtc   2160
ggctatgtca acgttaatat gggcctaaaa ctcagacaac tattgtggtt tcacatttcc   2220
tgtcttactt ttggaagaga aactgttctt gaatatttgg tgtcttttgg agtgtggatt   2280
cgcactcctc ccgcatatag accgccaaat gcccctatct tatcaacact tccggaaact   2340
actgagtta gacgaagagg caggtcccct agaagaagaa ctccctcgcc tcgcagacga    2400
aggtctcaat cgccgcgtcg cagaagatct aaatctcggg aatctcaatg ttagtattcc   2460
ttggacacac aaggtgggaa actttacggg gctttattct tctacggtac cttgcttaa    2520
tcctaaatgg caaactcctt cttttcctga cattcatttg caggaggaca ttgttgatag   2580
atgtaagcaa tttgtggggc cccttacagt aaatgaaaat aggagactta aattaattat   2640
gcctgctagg ttttatccca atgttactaa atatttgccc ttagataaag ggatcaaacc   2700
gtattatcca gagtatgtag ttgatcatta cttccagacg cgacattatt tacacactct   2760
ttggaaggcg gggatcttat ataaaagaga gtccacacgt agcgcctcat tttgcgggtc   2820
accatattct tgggaacaag atctacagca tgggaggttg gtcttccaaa cctcgaaaag   2880
gcatggggac aaatctttct gtccccaatc cctgggatt cttccccgat catcagttgg    2940
accctgcatt caaagccaac tcagaaaatc cagattggga cctcaacccg tacaaggaca   3000
actggccgga cgccaacaag gtgggagtgg gagcattcgg gccagggttc accccctcccc  3060
atggggggact gttgggttgg agccctcagg ctcagggtct actcacaact gtgccagcag  3120
ctcctcctcc tgcctccacc aatcggcagt taggaaggca gcctactccc ttatctccac   3180
ctctaaggga cactcatcct caggccatac agtgg                              3215
```

Cell Culture

HepG2 cells were obtained from the American Type Culture Collection (Manassas, Va.; ATCC Catalog#HB-8065) and maintained in humidified incubators at 37° C. and 5% $CO_2$ in complete media containing Dulbecco's Modified Eagle Medium (DMEM) (Fisher Scientific (Life Technologies); Waltham, Mass.; Catalog#11995-065), 10% fetal bovine serum (FBS) (Life Technologies, Catalog#10082-147), 100 units/mL penicillin, 10 µg/mL streptomycin, and 0.25 µg/mL of Fungizone (Life Technologies, Catalog#15240-062).

Transient Transfection

HepG2 cells were seeded in collagen coated 96-well plates (BIOCOAT™; Fisher Scientific, Catalog#354407) at a density of 20,000 cells/well and allowed to attach overnight at 37° C. and 5% $CO_2$. Cells were co-transfected with HBV plasmids (100 ng/well) and *Gaussia* expression plasmid (10 ng/well) (THERMO SCIENTIFIC™, Fisher Scientific, Catalog#16148) using the Lipofectamine LTX Plus transfection reagent according to manufacturer recommendation (Life Technologies, Catalog#15338-100). Transfection mixtures were removed the following day, cells were washed twice with complete media and were treated with serially diluted compounds at a final dimethyl sulfoxide (DMSO) concentration of 0.5%. Cells were incubated with compounds for three days, after which intracellular HBV DNA was extracted from cells and levels of secreted Gaussian luciferase was determined from the medium using the *Gaussia* Flash Luciferase assay kit (THERMO SCIENTIFIC™, Fisher Scientific, Catalog#16158). To extract intracellular HBV DNA, cells were washed once with 100 µL Dulbecco's phosphate-buffered saline (Life Technologies, Catalog#14190-144) and lysed with 0.33% NP-40 (THERMO SCIENTIFIC™, Fisher Scientific, Catalog#85124) by incubating for 30 minutes at room temperature (110 µL/well). Turbo DNase was prepared by diluting 5-fold into Turbo DNase buffer (Life Technologies, Catalog# AM2238), and S7 nuclease (Roche Catalog#10-107-921-001, available from Sigma-Aldrich; St. Louis, Mo.) was prepared by diluting 50-fold into CUTSMART® buffer (New England Bioloabs; Ipswich, Mass.; Catalog#B7204S) containing 25 µM $CaCl_2$ (GBiosciences; St. Louis, Mo.; Catalog#R033). Nuclei were pelleted by centrifugation and supernatant (35 µL) was transferred into a fresh 96-well plate and treated with 2 units of Turbo DNase and 10 units of S7 nuclease at 37° C. for 60 minutes, followed by inactivation of the enzyme at 75° C. for 15 minutes. Encapsidated HBV DNA was diluted with 60 µL molecular biology grade water (GBiosciences Catalog#786-293) and extracted by incubating in 50 µL lysis buffer (Affymetrix Catalog#QS0010) containing 2.5 µg Protease K (Affymetrix; Santa Clara, Calif. Catalog#14600) at 50° C. for 40 minutes. HBV DNA was denatured for 30 minutes at 25° C. by the addition of 2.5 M NaOH (Sigma, Catalog #S5881) to a final concentration of 0.2 M in the presence of 1 µL HBV DNA probes (Affymetrix, 10 Catalog#SF-10326). The denatured DNA was neutralized by the addition of 2 M HEPES (Sigma, Catalog#H3375) to a final concentration of 0.3 M and detected using QuantiGene assay kit (Affymetrix, Catalog#QS0010). The mean background signal from wells containing only culture medium was subtracted from all other samples, and percent inhibition at each compound concentration was calculated by normalizing to signals from cells treated with 0.5% DMSO using equation E1.

$$\% \text{ inhibition}=(DMSO_{ave}-X_i)/DMSO_{ave}\times100\% \quad (E1):$$

where $DMSO_{ave}$ is the mean signal calculated from the wells that were treated with DMSO control (0% inhibition control) and Xi is the signal measured from the individual wells. EC50 values, effective concentrations that achieved 50% inhibitory effect, were determined by non-linear fitting using Graphpad Prism software (San Diego, Calif.) and equation E2.

$$Y=Y_{min}+(Y_{max}-Y_{min})/(1\pm10^{(LogEC50-x)\times HillSlope)} \quad (E2):$$

where Y represents percent inhibition values and X represents the logarithm of compound concentrations.

To determine the replication competence of HBV variants, the background corrected values for HBV DNA from the QuantiGene assay were normalized using the Gaussian luciferase activity values in order to account for any differences in transfection efficiency. The normalized HBV DNA values obtained from cells transfected with HBV variants were then compared with those obtained from the wild type HBV transfection, with wild-type HBV replication competence set at 100%.

Example 1.2

Relative Replication Competence of Nucleoside Resistant HBV Variants

Five HBV expression plasmids were generated to represent a panel of the nucleoside resistant HBV variants that are most commonly observed in HBV infected patients treated with nucleoside drugs. The HBV nucleoside resistance panel consists of five HBV variants with the following single, double, or triple mutations in the HBV polymerase protein: (1) L180M/M204V, (2) N236T, (3) A181V, (4) A181V/N236T, and (5) L180M/M204V/N236T. A181V, N236T, and A181V/N236T were introduced into the backbone of the HBV DNA obtained from a genotype B clinical isolate (Genbank 11 AY220698). Sequencing of the A181V, N236T, and A181V/N236T variants confirmed the intended amino acid change within the wild type genotype B HBV construct. To generate the triple mutant, N236T was introduced into the backbone of the HBV DNA obtained from the LMV resistant clinical isolate (Genbank AY220697; SEQ ID NO:5 (see Table 1)). It was previously reported that the LMV resistant clinical isolate contained a number of additional amino acid changes within the HBV genome compared to the isolate obtained prior to LMV treatment (Zhang J M et al. 2005. J Med Virol 77: 203-208). Sequencing the L180M/M204V and the L180M/M204V/N236T variants confirmed that there was an additional amino acid change at position 271 within the reverse transcriptase domain, which was consistent with the published sequence from the LMV resistant clinical isolate (Genbank AY220697; SEQ ID NO:5).

These plasmids were used to transfect HepG2 cells, and the amount of intracellular, encapsidated HBV DNA that was formed from HBV replication was quantified on day 3 after transfection. A *Gaussia* luciferase expression plasmid was co-transfected with HBV (*Gaussia*-Luc:HBV at 1:10 ratio) to allow normalization for any differences in transfection efficiency. The normalized HBV DNA signal obtained in cells transfected with wild-type HBV was defined as 100% relative replication competence. The N236T variant showed similar replication competence as wild type HBV, while the other four variants showed similar or up to two-fold higher replication competence as compared to wild type. The replication competence of all HBV variants was suitable for antiviral activity studies with nucleoside analogs and Compound 1.

Example 1.3

HBV Variants were Resistant to Nucleoside Analogs but Remained Susceptible to Compound 1

Figure 1A:
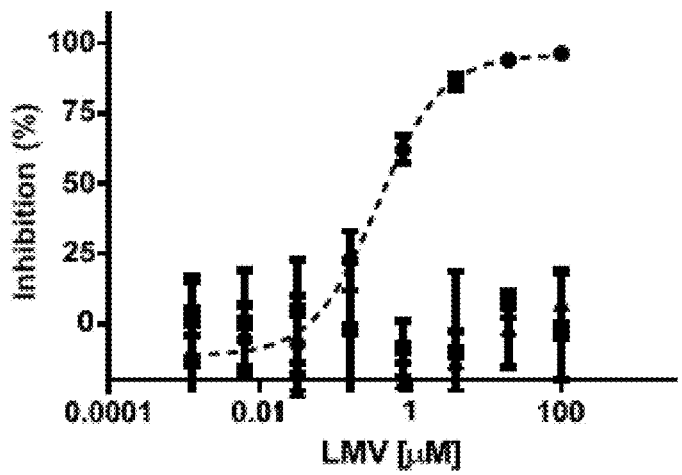
FIG. 1A, FIG. 1B, and FIG. 1C show HepG2 cells transiently transfected with wild type HBV (filled circles) and variants containing rtL180M/M2004V (filled triangles) or rtL180M/M204V/N236T (filled squares) amino acid changes were incubated with increasing concentrations of LMV (FIG. 1A), ETV (FIG. 1B), or TDF (FIG. 1C). Dose response curves against wild type HBV are shown as dash lines. Data points represented mean values from at least three independent transfection studies, and standard deviations are shown as error bars.
Figure 1B:
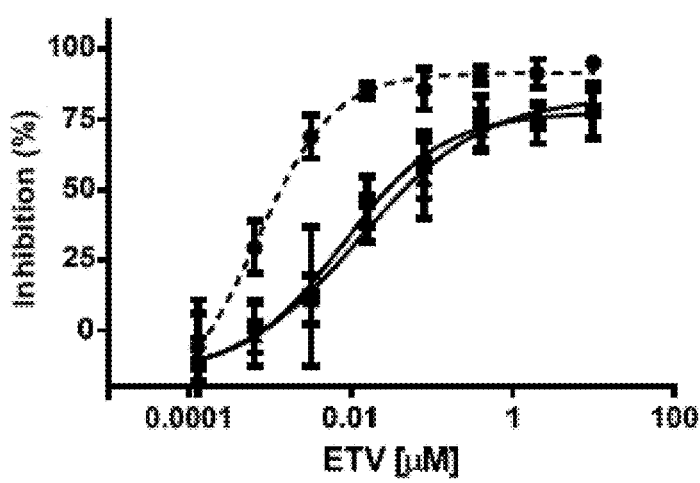
Figure 1C:
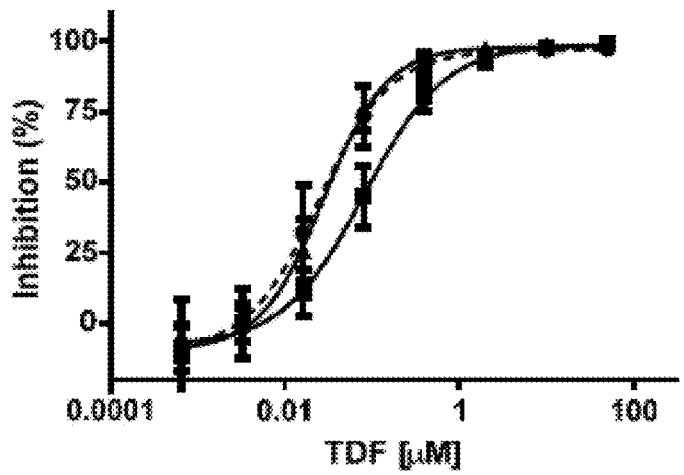

HBV variants with nucleoside resistance mutations were first evaluated for their susceptibility towards the inhibitory effect of nucleoside analogs. As expected from published data (Yang et al. 2005. Antivir Ther 10: 625-633; Brunelle et al. 2005. Hep 41: 1391-1398), both rtL180M/M204V and rtL180M/M204V/N236T HBV variants were resistant to inhibition by lamivudine (LMV) and entecavir (ETV): LMV inhibited wild-type HBV with a mean EC50 value of 0.53 µM, but did not inhibit replication of any of the two variants up to the highest concentration of LMV tested (100 µM), while the antiviral activity of ETV was reduced by 31- and 14-fold against the rtL180M/M204V and rtL180M/M204V/N236T variants, respectively (FIG. 1 and Table 2).

showed that cross resistance could exist among different classes of nucleoside analogs including LMV, ETV, and TDF. In contrast, Compound 1 remained active against nucleoside resistant variants and therefore lacked cross resistance with the nucleoside analogs.

Example 2

Viability of Primary Human Hepatocytes in the Presence of Compound 1 and Nucleoside Analogs Alone or in Combination In this example, the viability of primary human hepatocytes (PHH) was determined in the presence of Compound 1 and nucleoside analogs alone or in combination. Cell viability was determined as the relative concentration of intracellular ATP concentration in compound treated as compared to untreated cells. PHH viability was similar in untreated cells and cells treated with either 300 µM lamivudine (LMV), 30 µM tenofovir (TFV), or 30 µM entecavir (ETV). A dose dependent reduction in cell viability was

TABLE 2

Antiviral activity of Compound 1, LMV, ETV, and TDF in HepG2 cells transiently transfected with nucleoside resistant variants

| Compound | WT EC$_{50}$ [µM] | Fold Change | | | | |
|---|---|---|---|---|---|---|
| | | rtL 180M/M204V | rtL 180M/M204V/ N236T | rtA181V | rtN236T | rtA181V/ N236T |
| LMV | 0.53 ± 0.12 | >190 | >190 | 1.7 ± 0.9$^{ns}$ | 1.0 ± 0.5$^{ns}$ | 4.8 ± 2.3$^{a}$ |
| ETV | 0.0014 ± 0.0004 | 31 ± 16$^{a}$ | 14 ± 4$^{a}$ | 2.2 ± 0.5$^{a}$ | 0.67 ± 0.22$^{ns}$ | 1.8 ± 0.6$^{ns}$ |
| TDF | 0.032 ± 0.015 | 1.1 ± 0.3$^{ns}$ | 2.9 ± 1.5$^{b}$ | 1.4 ± 0.05$^{ns}$ | 2.2 ± 1.0$^{b}$ | 2.8 ± 1.4$^{b}$ |
| Cmpd 1 | 0.31 ± 0.10 | 1.3 ± 0.6$^{ns}$ | 1.4 ± 0.5$^{ns}$ | 0.82 ± 0.19$^{ns}$ | 0.85 ± 0.40$^{ns}$ | 0.85 ± 0.26$^{ns}$ |

EC$_{50}$ and fold change shown as mean value ± standard deviation (SD) from at least three independent studies.
*Mean Fold change and Fold change SD calculated from individual fold change values of mutant variants relative to mean wild-type EC$_{50}$ value.
$^{a}$as compared to wild-type, ttest p value < 0.01;
$^{b}$ttest p value < 0.05;
$^{ns}$ ttest p value > 0.05.

Tenofovir disoproxil fumarate (TDF) showed similar antiviral activity against wild type HBV and the rtL180M/M204V and rtA181V variants (mean EC50 values of 0.032, 0.034 and 0.043 µM, respectively), but showed mean reductions in antiviral activity ranging from 2.2 to 2.9-fold against HBV variants containing the rtN236T mutation either alone or in combination with rtL180M/M204V or rtA181V (FIG. 1; Table 2). These relative fold changes associated with the N236T mutation were similar to previously published fold change values (Delaney et al. 2006. Antimicrob Agents Chemother 50: 2471-2477).

HBV containing the rtN236T mutation remained sensitive to inhibition by LMV and ETV, similar to wild-type HBV (Table 2). A slight increase in mean EC50 values (about 2-fold) was observed for LMV and ETV when tested against the rtA181V variant (Table 2). The combination of the rtN236T to rtA181V mutations into a double mutant variant resulted in mean 4.8-fold and 1.8-fold increases in EC50 values for LMV and ETV, respectively (Table 2).

All five nucleoside resistant HBV variants were sensitive to inhibition by Compound 1 with antiviral EC50 values similar to wild-type HBV. Mean EC50 fold changes ranged from 0.82 to 1.4-fold, indicating that nucleoside resistance conferring mutations tested here did not confer cross resistance to the HBV core inhibitor Compound 1 (Table 2).

As shown in this example, phenotyping assay using HepG2 cells transiently transfected with nucleoside analogs observed in cells treated with Compound 1; mean CC50 values ranged from 16 to 82 µM. The CC50 values obtained with Compound 1 in the presence of 300 µM lamivudine (LMV), 30 µM tenofovir (TFV), or 30 µM entecavir (ETV) were similar to those obtained when the cells were treated with Compound 1 alone.

Example 2.1

Materials and Methods

Compounds

Compound 1 was synthesized. Lamivudine, Tenofovir, and Entecavir were purchased from Toronto Research Chemicals (Toronto, Canada).

Cell Culture

Cryopreserved primary human hepatocytes from individual donors (primary hepatocyte IDs: HuM4038, HuM4055A, and HuM4059) were purchased from Triangle Research Labs (TRL; Research Triangle Park, N.C.). Cells were thawed using hepatocyte thawing medium (TRL, Catalog#MCHT50) according to manufacturers' recommendations. After centrifugation, cells were resuspended in supplemented hepatocyte plating medium (TRL, Catalog#MP250). Cells were plated in collagen Type I coated 96-well plates (Corning; Corning, N.Y.; Catalog#356407) at a density of 40,000 cells per well and maintained in humidified incubators at 37° C. and 5% $CO_2$ overnight prior to addition of test compounds.

Cell Viability Assays

For each donor, three 96-well plates were set up to evaluate the effect of increasing concentrations of Compound 1 either alone or in combination with nucleoside analogs on hepatocyte cell viability. On each plate, cells were incubated with Compound 1 alone as duplicates, or Compound 1 in the presence of LMV, TFV, or ETV as triplicates. The effects of nucleoside analogs alone on hepatocyte cell viability were also determined in triplicates for each donor. Compound 1 was half-log serially diluted in DMSO (Sigma, Catalog #D2650) and added to primary human hepatocytes either alone or in combination with LMV (30 and 300 µM), TFV (30 µM), or ETV (30 µM). Single and combined drugs were added to primary human hepatocytes at a final DMSO (Sigma D2650) concentration of 0.5% across all concentrations. Cells were incubated with compounds for three days, after which medium was removed and fresh medium containing compounds was added and incubated for another three days. As a no compound control, primary human hepatocytes were treated with 0.5% DMSO, and these values were then used to define the 0% inhibition level. Background signal was determined as the mean value from wells containing only culture medium. Cell viability was monitored by using CellTiter-Glo cell viability reagent according to the manufacturer protocol (Promega; Madison, Wis.; G7573). Chemiluminescence signal proportional to the amount of cellular ATP was measured by using the Victor X4 plate reader (Perkin Elmer; Waltham, Mass.). The mean background signal from the medium only wells was subtracted from all other samples, and percent inhibition was calculated using equation E1 (as in Example 1):

$$\% \text{ inhibition} = (DMSO_{ave} - X_i)/DMSO_{ave} \times 100\% \quad (E1)$$

where $DMSO_{ave}$ is the mean signal calculated from the wells that were treated with 0.5% DMSO control (0% inhibition control) and X, is the signal measured from the individual wells. CC50 values were determined from the % inhibition data obtained at different compound concentrations by non-linear fitting using Graphpad Prism software and equation E3, in cases were % inhibition values exceeded 50% at the highest concentration tested.

$$Y = Y_{min} + (Y_{max} - Y_{min})/(1 + 10^{(LogCC50-X) \times HillSlope}) \quad (E3)$$

where Y represents percent inhibition values and X represents the logarithm of compound concentrations.

Example 2.2

Effect of Compound 1 or Nucleoside Analogs on Cell Viability Using Primary Human Hepatocytes Primary human hepatocytes from three different donors (TRL HuM4038, HuM4055A and HuM4059) were incubated with increasing concentrations of Compound 1. Cells from the same three donors were also incubated with LMV (30 and 300 µM), TFV (30 µM) or ETV (30 µM). Analysis of cell viability was based on intracellular ATP levels after 6 days of drug treatment. There was a concentration dependent reduction of cell viability, when hepatocytes were incubated with Compound 1: CC50 values for Compound 1 ranged from 16 µM to 82 µM (Table 3). Previously reported CC50 values for Compound 1 using fresh (Bioreclamation-IVT) and cryopreserved primary hepatocytes (donors TRL HuM4038 and Invitrogen Hu1457), ranged from 14 to 27 µM. No reduction of cell viability was observed when hepatocytes were treated with 30 or 300 µM LMV, 30 µM TFV, or 30 µM ETV (Table 3).

TABLE 3

Effect of Compound 1, LMV, TFV, or ETV on cell viability in primary human hepatocytes

| Compound | HuM4038 CC50 [µM] | HuM4038 CC50 [µM] | HuM4055A CC50 [µM] | HuM4059 CC50 [µM] |
|---|---|---|---|---|
| Cmpd 1 | 16 | 26 | 19 | 82 |
| LMV | >30 | >300 | >300 | >300 |
| TFV | >30 | >30 | >30 | >30 |
| ETV | >30 | >30 | >30 | >30 |

Example 2.3

Figure 2A:
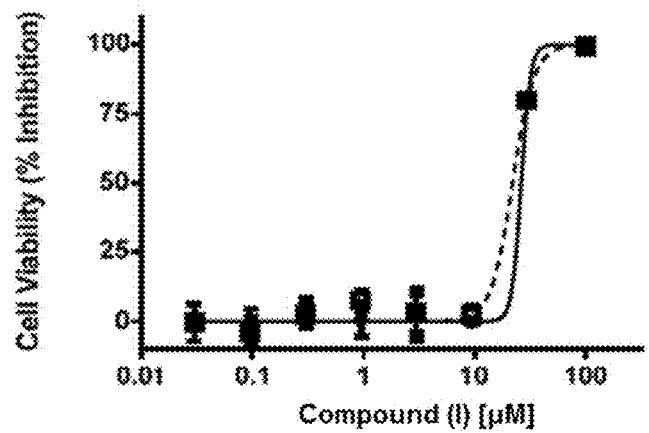
FIG. 2A, FIG. 2B, and FIG. 2C show the effect of combining Compound 1 with nucleoside analogs on cell viability in primary human hepatocytes from donor HuM4038. Cell viability dose response curves of Compound 1 alone (circle, solid line) or in combination with nucleoside analogs (square, dash line)
Figure 2B:
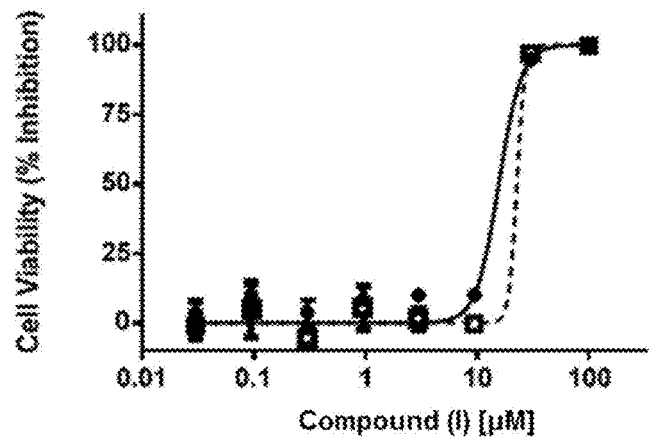
Figure 2C:
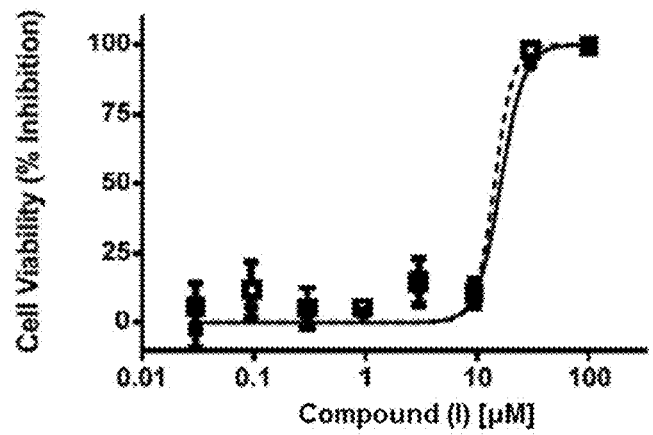
Figure 3A:
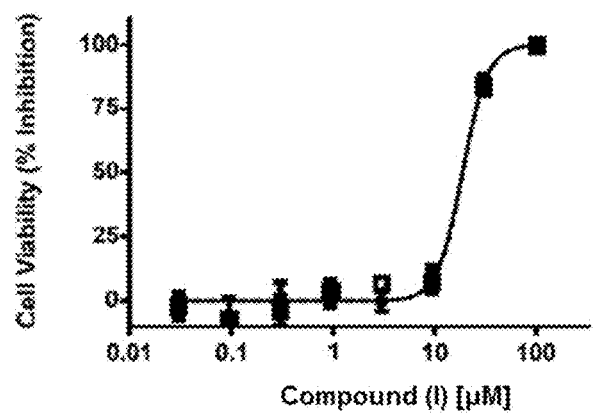
FIG. 3A, FIG. 3B, and FIG. 3C show the effect of combining Compound 1 with nucleoside analogs on cell viability in primary human hepatocytes from donor HuM4055A. Cell viability dose response curves of Compound 1 alone (circle, solid line) or in combination with nucleoside analogs (square, dash line)
Figure 3B:
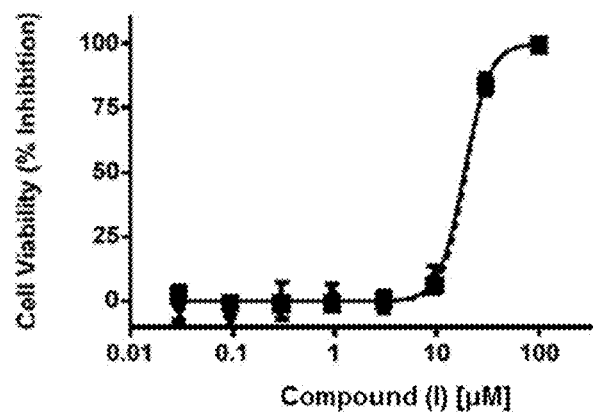
Figure 3C:
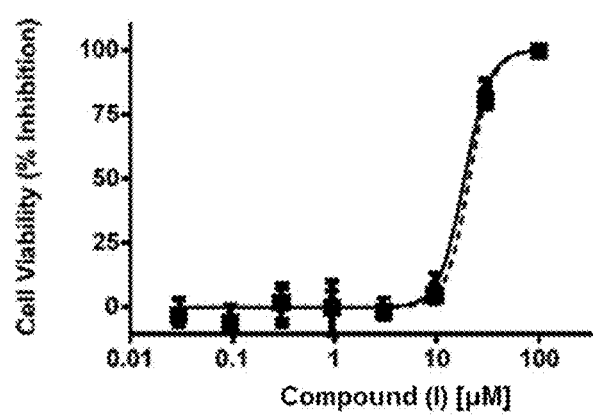
Figure 4A:
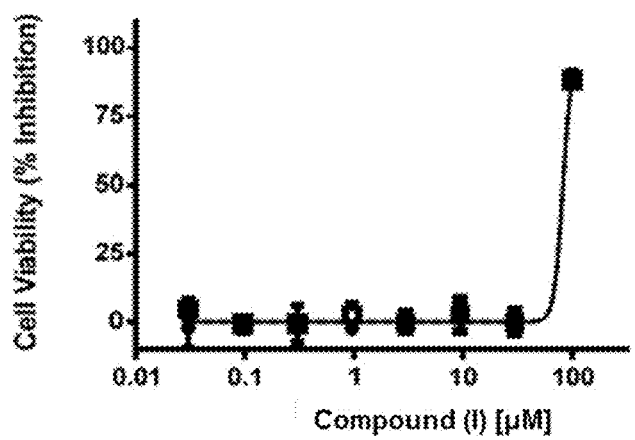
FIG. 4A, FIG. 4B, and FIG. 4C show the effect of combining Compound 1 with nucleoside analogs on cell viability in primary human hepatocytes from donor HuM4059. Cell viability dose response curves of Compound 1 alone (circle, solid line) or in combination with nucleoside analogs (square, dash line)
Figure 4B:
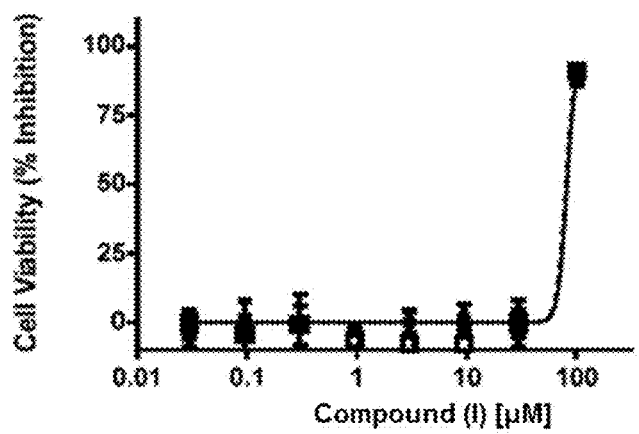
Figure 4C:
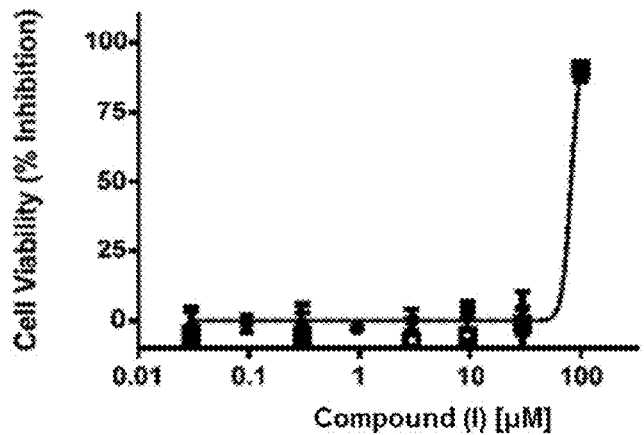
Figure 5:
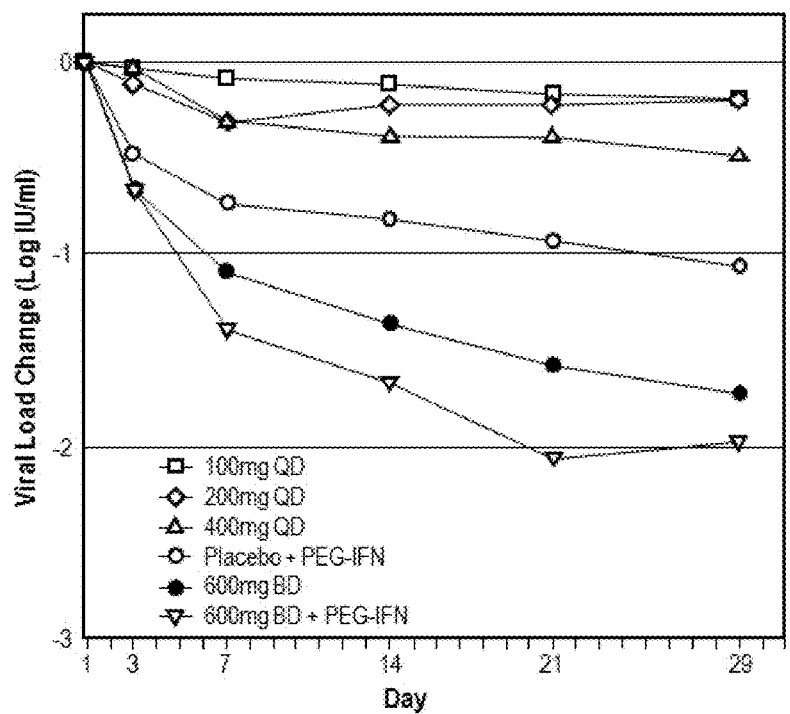
FIG. 5 shows the efficacy results in a trial of patients administered Compound 1 alone or with PegIFN.
Figure 6:
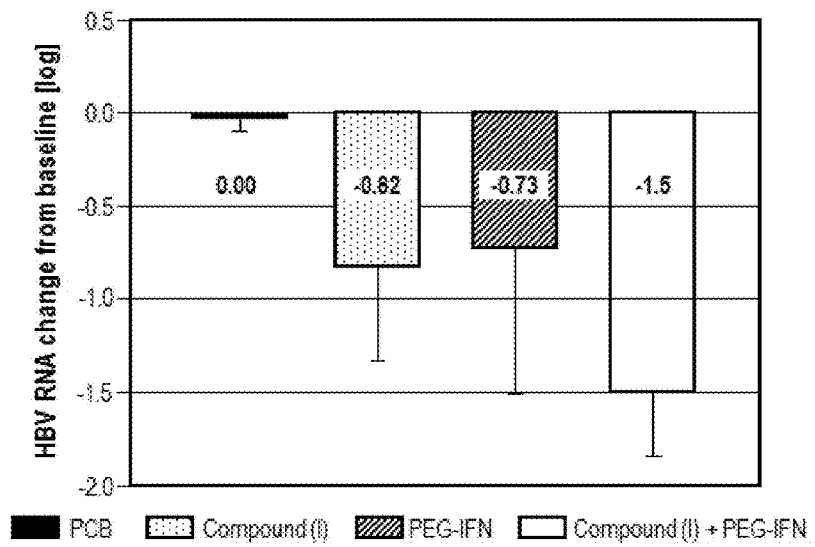
FIG. 6 shows serum HBV RNA reductions in patients administer placebo (PCB), Compound 1 (600 mg BD), 180

Combined Effect of Compound 1 with Nucleoside Analogs on Cell Viability Using Primary Human Hepatocytes In order to determine the effect of combining Compound 1 and nucleoside analogs on cell viability, primary human hepatocytes were treated with increasing concentrations of Compound 1 in combination with single concentrations of LMV (300 µM), TFV (30 µM), or ETV (30 µM). As shown in FIGS. 2-4, the presence of LMV, TFV, or ETV did not affect the dose response profiles of Compound 1 when tested across the three different donors. The corresponding CC50 values of Compound 1 were similar when determined in the presence or absence of nucleoside analogs (Tables 4-6).

TABLE 4

Effect of Compound 1 alone and in combination with 300 µM LMV on viability of primary human hepatocytes

| Donor ID | Cmpd (I) CC50 [µM] | Cmpd (I) + LMV CC50 [µM] | CC50 fold change mono/combo |
|---|---|---|---|
| HuM4038 | 26 | 22 | 1.2 |
| HuM4055A | 19 | 19 | 1.0 |
| HuM4059 | 83 | 83 | 1.0 |

TABLE 5

Effect of Compound 1 alone and in combination with 30 µM TFV on viability of primary human hepatocytes

| Donor ID | Cmpd (I) CC50 [µM] | Cmpd (I) + TFV CC50 [µM] | CC50 fold change mono/combo |
|---|---|---|---|
| HuM4038 | 16 | 23 | 0.7 |
| HuM4055A | 19 | 19 | 1.0 |
| HuM4059 | 83 | 80 | 1.0 |

TABLE 6

Effect of Compound 1 alone and in combination with 30 µM ETV on viability of primary human hepatocytes

| Donor ID | Cmpd (I) CC50 [µM] | Cmpd (I) + ETV CC50 [µM] | CC50 fold change mono/combo |
|---|---|---|---|
| HuM4038 | 16 | 14 | 1.1 |
| HuM4055A | 19 | 21 | 0.9 |
| HuM4059 | 83 | 81 | 1.0 |

In this example, the viability of primary human hepatocytes (PHH) was determined in the presence of Compound 1 and nucleoside analogs alone or in combination. Cell viability was determined as the relative concentration of intracellular ATP concentration in compound treated as compared to untreated cells. PHH viability was similar in untreated cells and cells treated with either 300 µM lamivudine (LMV), 30 µM tenofovir (TFV) or 30 µM entecavir (ETV). A dose dependent reduction in cell viability was observed in cells treated with Compound 1; CC50 values ranged from 16 to 82 µM. The CC50 values obtained with Compound 1 in the presence of 300 µM lamivudine (LMV), 30 µM tenofovir (TFV) or 30 entecavir (ETV) were similar to those obtained when the cells were treated with Compound 1 alone.

Example 3

Effect of the Combination of the HBV Core Inhibitor Compound 1 with Nucleoside Analogs or Other HBV Core Inhibitors on the Inhibition of HBV DNA Replication in HepG2.2.15 Cells In this example, the combination of the HBV core modulator Compound 1 with LMV is shown to be additive as analyzed by both MacSynergy and CalcuSyn. Combining Compound 1 with TFV or ETV showed additive effect as analyzed by MacSynergy and slight to moderate synergism as analyzed by CalcuSyn. The combination of two different HBV core inhibitors showed overall additive antiviral activity. Cell viability remained above 85% in all samples treated with the highest compound concentrations, either alone or in combination.

Example 3.1

Materials and Methods

HepG2.2.15 cells were treated with increasing concentrations of Compound 1 (0.05-5 µM) combined with increasing concentrations of either lamivudine (LMV), tenofovir (TFV), entecavir (ETV), or Bay 41-4109 (0.01-5 µM) for six days. Secreted HBV DNA was measured by Quantigene assay and cell viability was measured by CellTiter-glo assay. Synergy was measured by both MacSyngergy analysis and Calcusyn analysis.

Example 3.2

Results

FIG. 7 shows the effect of Compound 1 in combination with nucleoside analogs. Synergy plots at 95% confidence from MacSynergy using three different assay plates of HepG2.2.15 cells treated with Compound 1 in combination with LMV (FIG. 7A), TFV (FIG. 7B), or ETV (FIG. 7C).

Table 7 shows the synergy/antagonism volumes for Compound 1 in combination with nucleoside analogs, show the MacSynergy predicted effect. Synergy/antagonism volumes at 95% confidence of <25 µM2% defined as insignificant, between 25 and 50 µM2% as minor, between 50 and 100 µM2% as moderate, and >100 µM2% as strong synergy/antagonism. As shown, a Compound 1 showed additive effects when combined with LMV, TFV, or ETV when using MacSynergy.

TABLE 7

| Combination Compound 1 with | Synergy ($\mu M^2$ %) | Antagonism ($\mu M^2$ %) | MacSynergy predicted effect |
| --- | --- | --- | --- |
| LMV | 5.1 | −14.3 | Additive |
| TFV | 18.5 | −7.3 | Additive |
| ETV | 1.0 | −16.5 | Additive |

Table 8 shows the combination index (CI) values for Compound 1 in combination with nucleoside analogs. These results show that Compound 1 in combination with LMV shows an additive effect when using CalcuSyn, and slight to moderate synergy when Compound 1 is combined with TFV or ETV.

TABLE 8

| Combination | CI Values | | | | CalcuSyn predicted effect |
| --- | --- | --- | --- | --- | --- |
| Compound 1 with | ED50 | ED75 | ED90 | Overall CI | |
| LMV | 1.0 | 0.8 | 0.8 | 0.9 ± 0.1 | Additive |
| TFV | 0.8 | 0.8 | 0.8 | 0.8 ± 0.06 | Slight to moderate synergy |
| ETV | 1.0 | 0.5 | 0.5 | 0.7 ± 0.4 | Slight to moderate synergy |

Figure 8:
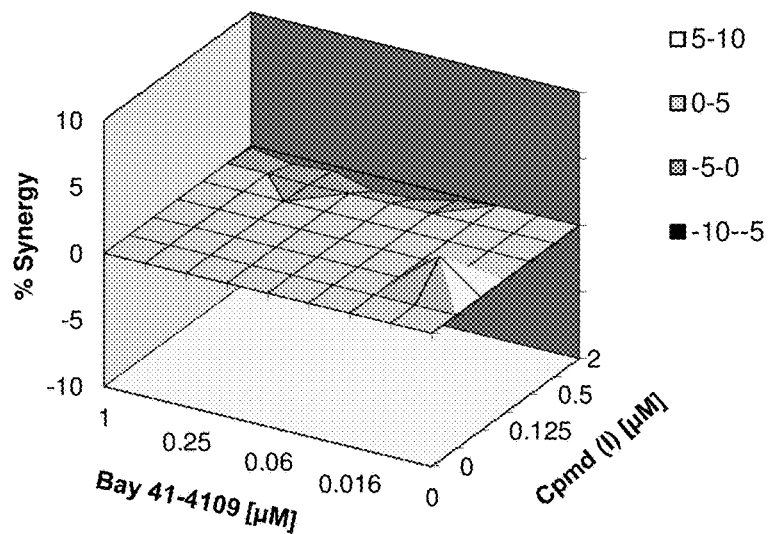

FIG. 8 shows the effect of Compound 1 in combination with other core modulators. Synergy plots at 95% confidence from MacSynergy using three different assay plates of HepG2.2.15 cells treated with Compound 1 in combination with Bay 41-4109 (FIG. 8).

Table 9 shows the synergy/antagonism volumes for Compound 1 in combination with another core modulator. Using MacSynergy, Compound 1 has an additive effect when combined with Bay 41-4109 (Formula B).

TABLE 9

| Combination of Compound 1 with | Synergy ($\mu M^2$ %) | Antagonism ($\mu M^2$ %) | MacSynergy predicted effect |
| --- | --- | --- | --- |
| Bay 41-4109 | 2.3 | −3.9 | Additive |

Table 10 shows CI values for Compound 1 in combination with another core modulator, Bay 41-4109, showing that the combinations has additive effects as predicted using CalcuSyn.

TABLE 10

| Combination | CI Values | | | | CalcuSyn predicted effect |
| --- | --- | --- | --- | --- | --- |
| Compound 1 with | ED50 | ED75 | ED90 | Overall CI | |
| Bay 41-4109 | 1.1 | 1.1 | 1.1 | 1.1 ± 0.1 | Additive |

Example 4

Effect of the Combination of the HBV Core Inhibitor Compound 2 and Compound 3 with Nucleoside Analogs on the Inhibition of HBV DNA Replication in HepG2.2.15 Cells In this example, the combination of the HBV core modulator Compound 2 or Compound 3 with TFV or ETV is shown to be additive to synergistic as analyzed by MacSynergy.

Example 4.1

Materials and Methods

The anti-HBV activity of combinations of Compound 2 and Compound 3 with the nucleos(t)ide analogues ETV or TFV was assessed in a 6-day HBV antiviral assay using qPCR for the detection of HBV DNA in the cell culture supernatant as a read-out. The combination effect was analyzed using Mac Synergy II software. The anti-HBV activity of ETV and TFV when tested as single agents in HepG2.2.15 cells as well (Table 14).

During the antiviral testing, HepG2.2.15 cells were cultured in RPMI1640 medium and the FBS was reduced to 2%. Cells were plated at a density of 50.000 cells per well into a 96-well plate.

One day after seeding of the HepG2.2.15 cells, the supernatant was removed and 200 μL medium with test compounds, diluted in a checkerboard fashion, was added to the cells. After three days the medium with test compound was refreshed and the cells were incubated in the presence of compound for three additional days. At the end of the compound treatment, 150 μL cell culture supernatant and 50 μL PBS were added to a 96-well block for DNA extraction using the MagNA Pure 96 DNA and Viral NA Small Volume Kit. HBV DNA was detected by quantitative real time PCR (qPCR). HBV DNA was quantified by a real-time PCR assay using a LightCycler480 Probes Master kit (Roche) with primers 5'-GTGTCTGCGGCGTTTTATCA-3' (sense) and 5'-GACAAACGGGCAACATACCT-3' (antisense, SEQ ID NO: 7). HBV probe 5'-CCTCTKCATCCTGCTGCTATGC-CTCATC-3' (SEQ ID NO: 8) contains a fluorescent reporter dye (FAM) at the 5'end of the probe and a quencher dye (TAMRA) at the 3'end. The PCR was carried out as follows: denaturing at 95° C. for 10 minutes, followed by 40 cycles of amplification at 95° C. for 15 seconds and at 60° C. for 1 minute. Cytotoxicity testing of compounds was performed on HepG2.2.15 in parallel using the same experimental design as in the antiviral assay. The ATP lite kit from Perkin Elmer was used to detect ATP as a marker for cytotoxicity of compound treatment.

The percentage inhibition values obtained for each combination of compound concentration was calculated as the average of 3 to 5 replicate plates of the same combination per experiment. To robustly identify outliers, the distance from the average of the other 4 replicates was calculated for every data point. The distribution of these distances, over all data points, was found to be approximately normal and centered on zero, as expected, but with long tails, suggesting the presence of significant outliers. To determine a cut-off to exclude these, Tukey's outlier criterion was used, which sets the limits at the first quartile minus 1.5 times the inter-quartile range (Q1−1.5*(Q3−Q1)) and at the third quartile plus 1.5 times the inter-quartile range (Q3+1.5*(Q3−Q1)). To make the outlier filtering symmetric, the maximum of the absolute values of these limits as cut-off was taken. Marked as an outlier, and excluded from calculations, was any data point for which the absolute distance from the average of the other 4 replicates exceeded this cut-off. Removal of outliers was only performed in experiments 2 and 3. The anti-HBV activity of different combinations of anti-HBV agents was assessed using the Bliss-Independence model based on the algorithm developed by Prichard and Shipman (Prichard M N, Shipman C Jr. A three-dimensional model to analyze drug-drug interactions. Antiviral Res. 1990; 14(4-5):181-205) using the MacSynergy™ II software. In this model, the theoretical additive effect is calculated from the dose-response curves of the individual compounds by the equation $Z=X+Y\times(1-X)$, where X and Y represent the inhibition produced by drug 1 alone and drug 2 alone, respectively, and Z represents the effect produced by the combination of drug 1 and drug 2. The theoretical additive surface is subtracted from the actual experimental surface, resulting in a surface that appears as a horizontal plane at 0% inhibition if the combination was additive. Any peak above this plane indicates synergy, whereas any depression below this plane indicates antagonism. The lower limits of the 95% confidence intervals (CI) for the experimental dose-response surface were used to evaluate the data statistically. The volume of the peak or depression was calculated to quantify the overall synergy or antagonism produced. Values of synergy and antagonism at the 95% CI were considered to determine combination effect according to the Mac Synergy II handbook (which can be accessed via http://www.uab.edu/images/pediatrics/ID/MacSynergy.pdf).

TABLE 13

Concentration ranges of the various compounds used for each experiment

| | Concentration Range (nM) | | | |
|---|---|---|---|---|
| Experiment # | Compound 2 | Compound 3 | ETV | TFV |
| 1 | 1000-0.24 | 1000-0.24 | 25-0.024 | 250-0.24 |
| 2 | 250-3.9 | N/A | 25-0.10 | 250-1.0 |
| 3 | 250-3.9 | N/A | 25-0.10 | 250-1.0 |

Example 4.2

Results

TABLE 14

Synergy results summary for the combination of Compound 2 or Compound 3 with compounds ETV or TFV

| Formula and Anti-HBV agent combinations | Repeat measurements per experiment [a] | Synergy volumes (95% CI lower limit) ($\mu M^2$ %)[b] | Antagonism volumes (95% CI lower limit) ($\mu M^2$ %)[b] | Combination effect[c] |
|---|---|---|---|---|
| Compound 2 + ETV (Experiment 1) | 3 | 0 | −21.92 | Insignificant synergism/ antagonism (additivity) |
| Compound 2 + TFV (Experiment 1) | 3 | 1.13 | −10.98 | Insignificant synergism/ antagonism (additivity) |

TABLE 14-continued

Synergy results summary for the combination of Compound 2 or Compound 3 with compounds ETV or TFV

| Formula and Anti-HBV agent combinations | Repeat measure-ments per experiment [a] | Synergy volumes (95% CI lower limit) (µM² %)[b] | Antagonism volumes (95% CI lower limit) (µM² %)[b] | Combination effect[c] |
|---|---|---|---|---|
| Compound 2 + ETV (Experiment 2) | 5 | 14.66 | −2.7 | Insignificant synergism/antagonism (additivity) |
| Compound 2 + TFV (Experiment 2) | 5 | 273.83 | −0.55 | Strong synergism |
| Compound 2 + ETV (Experiment 3) | 5 | 332.45 | −15.1 | Strong synergism |
| Compound 2 + TFV (Experiment 3) | 5 | 413.62 | −6.19 | Strong synergism |
| Compound 3 + ETV (Experiment 1) | 3 | 79.1 | −13.75 | Moderate synergism |
| Compound 3 + TFV (Experiment 1) | 3 | 144.51 | −2.61 | Strong synergism |

TABLE 15

Anti-HBV activity of ETV and TFV when tested as single agents in HepG2.2.15 cells

| Compound | Median EC$_{50}$, nM | Experimental repeat # | Inhibitor Class |
|---|---|---|---|
| ETV | 0.07 | 2 | Nucleoside analogue |
| TFV | 15 | 1 | Nucleoside analogue |

The ATP cytotoxicity assay described above was performed in Experiment 1. Based on the raw data (not shown), the compounds do not show toxicity in any combination.

FIGS. 11A-C and FIGS. 12A-C show the effect of Compound 2 in combination with nucleoside analogs ETV and TFV. Synergy plots at 95% confidence from MacSynergy using three different assay plates of HepG2.2.15 cells treated with Compound 2 in combination with ETV (FIGS. 11A-C) and TFV (FIGS. 12A-C) are shown.

FIG. 13 and FIG. 14 show the effect of Compound 3 in combination with nucleoside analogs ETV and TFV. Synergy plots at 95% confidence from MacSynergy using three different assay plates of HepG2.2.15 cells treated with Compound 3 in combination with ETV (FIG. 13) and TFV (FIG. 14) are shown.

Figure 15A:
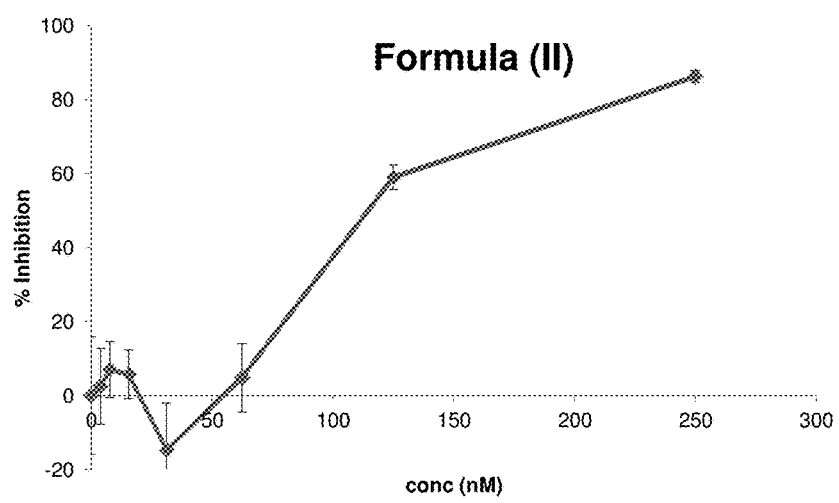
Figure 15B:
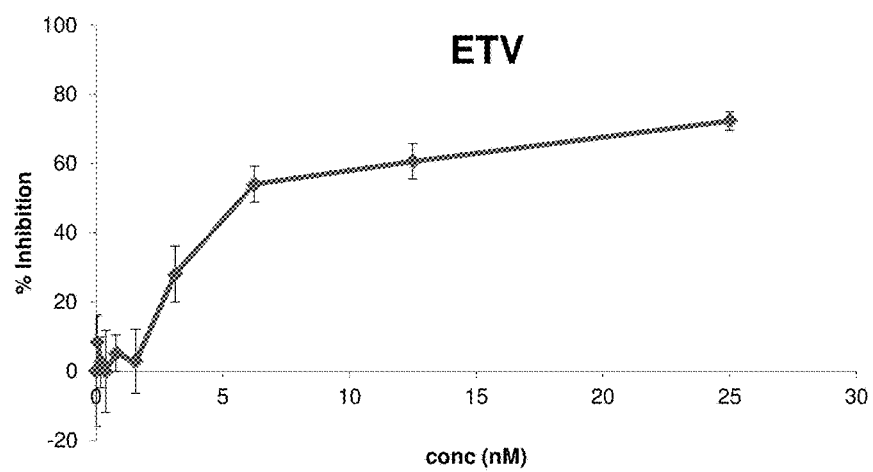
Figure 15C:
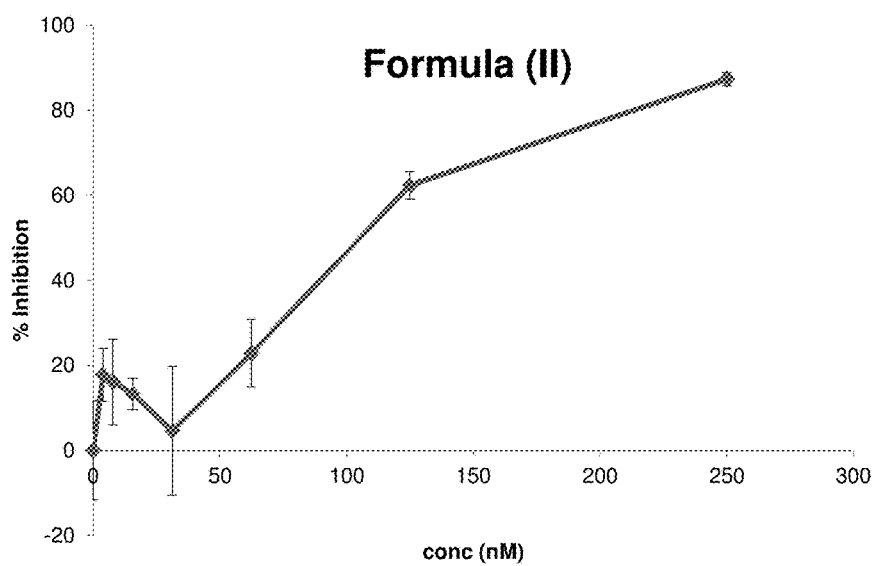
Figure 15D:
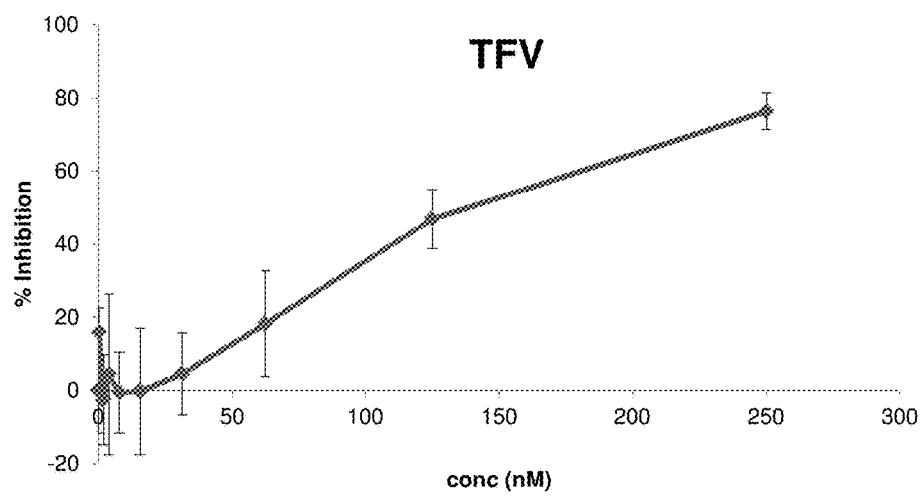

FIGS. 15A-D shows the % Inhibition of HBV with Compound 2 in combination with nucleoside analogs ETV and TFV. The plot of FIG. 15A shows % inhibition of HBV at the disclosed concentrations ranges of Compound 2 when the concentration of ETV was set to zero. The plot of FIG. 15B shows % inhibition of HBV at the disclosed concentrations ranges of ETV when the concentration of Compound 2 was set to zero. The plot of FIG. 15C shows % inhibition of HBV at the disclosed concentrations ranges of Compound 2 when the concentration of TFV was set to zero. The plot of FIG. 15D shows % inhibition of HBV at the disclosed concentrations ranges of TFV when the concentration of Compound 2 was set to zero.

The invention is not to be limited in scope by the specific embodiments and examples described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

The invention claimed is:

1. A combination product comprising a therapeutically effective amount of a core protein allosteric modulator (CpAM) and a therapeutically effective amount of reverse transcriptase inhibitor, wherein the core protein allosteric modulator is a core protein allosteric modulator that causes assembly of capsids that are essentially empty with respect to their viral contents, wherein the core protein allosteric modulator is compound 2:

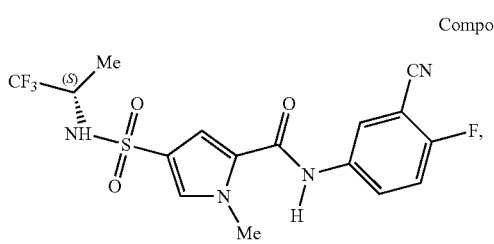

Compound 2 or a pharmaceutically acceptable salt thereof, a hydrate thereof, a solvate thereof, or a crystalline form thereof; and the reverse transcriptase inhibitor is entecavir.

2. A combination product comprising a therapeutically effective amount of a core protein allosteric modulator (CpAM) and a therapeutically effective amount of reverse transcriptase inhibitor, wherein the core protein allosteric modulator is a core protein allosteric modulator that causes assembly of capsids that are essentially empty with respect to their viral contents, wherein the core protein allosteric modulator is compound 2:

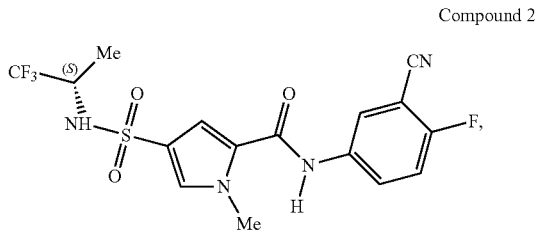

Compound 2 or a pharmaceutically acceptable salt thereof, a hydrate thereof, a solvate thereof, or a crystalline form thereof; and the reverse transcriptase inhibitor is tenofovir.

3. A combination product comprising a therapeutically effective amount of a core protein allosteric modulator (CpAM) and a therapeutically effective amount of reverse transcriptase inhibitor, wherein the core protein allosteric modulator is a core protein allosteric modulator that causes assembly of capsids that are essentially empty with respect to their viral contents, wherein the core protein allosteric modulator is compound 3:

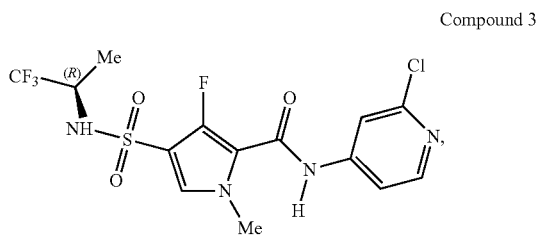

Compound 3 or a pharmaceutically acceptable salt thereof, a hydrate thereof, a solvate thereof, or a crystalline form thereof; and the reverse transcriptase inhibitor is entecavir.

4. A combination product comprising a therapeutically effective amount of a core protein allosteric modulator (CpAM) and a therapeutically effective amount of reverse transcriptase inhibitor, wherein the core protein allosteric modulator is a core protein allosteric modulator that causes assembly of capsids that are essentially empty with respect to their viral contents, wherein the core protein allosteric modulator is compound 3:

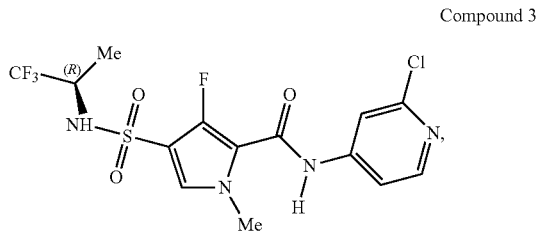

Compound 3 or a pharmaceutically acceptable salt thereof, a hydrate thereof, a solvate thereof, or a crystalline form thereof; and the reverse transcriptase inhibitor is tenofovir.

* * * * *